United States Patent
Alaniz et al.

(10) Patent No.: US 11,612,586 B2
(45) Date of Patent: Mar. 28, 2023

(54) INDOLE REGULATION OF ANTIGEN PRESENTING CELLS

(71) Applicants: THE TEXAS A&M UNIVERSITY SYSTEM, College Station, TX (US); TRUSTEES OF TUFTS COLLEGE, Medford, MA (US)

(72) Inventors: Robert C. Alaniz, College Station, TX (US); Arul Jayaraman, College Station, TX (US); Kyongbum Lee, Winchester, MA (US)

(73) Assignees: The Texas A&M University System, College Station, TX (US); Trustees of Tufts College, Medford, MA (US)

( * ) Notice: Subject to any disclaimer, the term of this patent is extended or adjusted under 35 U.S.C. 154(b) by 0 days.

(21) Appl. No.: 16/085,912

(22) PCT Filed: Mar. 17, 2017

(86) PCT No.: PCT/US2017/023024
§ 371 (c)(1),
(2) Date: Sep. 17, 2018

(87) PCT Pub. No.: WO2017/161307
PCT Pub. Date: Sep. 21, 2017

(65) Prior Publication Data
US 2020/0123498 A1   Apr. 23, 2020

Related U.S. Application Data

(60) Provisional application No. 62/310,630, filed on Mar. 18, 2016, provisional application No. 62/310,606, filed on Mar. 18, 2016, provisional application No. 62/310,643, filed on Mar. 18, 2016, provisional application No. 62/310,648, filed on Mar. 18, 2016.

(51) Int. Cl.
| | | |
|---|---|---|
| *A61K 31/405* | (2006.01) | |
| *A61K 31/404* | (2006.01) | |
| *A61K 31/475* | (2006.01) | |
| *A61K 35/17* | (2015.01) | |
| *A61K 45/06* | (2006.01) | |
| *A61P 1/00* | (2006.01) | |
| *A61P 29/00* | (2006.01) | |
| *C12N 5/0783* | (2010.01) | |
| *C12N 5/0784* | (2010.01) | |
| *A61K 35/12* | (2015.01) | |
| *A61K 31/7004* | (2006.01) | |

(52) U.S. Cl.
CPC .......... *A61K 31/405* (2013.01); *A61K 31/404* (2013.01); *A61K 31/475* (2013.01); *A61K 35/17* (2013.01); *A61K 45/06* (2013.01); *A61P 1/00* (2018.01); *A61P 29/00* (2018.01); *C12N 5/064* (2013.01); *C12N 5/0636* (2013.01); *C12N 5/0637* (2013.01); *A61K 31/7004* (2013.01); *A61K 2035/122* (2013.01); *C12N 2501/15* (2013.01); *C12N 2501/2301* (2013.01); *C12N 2501/2304* (2013.01); *C12N 2501/2306* (2013.01); *C12N 2501/2312* (2013.01); *C12N 2501/2321* (2013.01); *C12N 2501/2323* (2013.01); *C12N 2501/24* (2013.01); *C12N 2501/51* (2013.01); *C12N 2501/515* (2013.01); *C12N 2501/999* (2013.01); *C12N 2502/1121* (2013.01); *C12N 2502/1157* (2013.01)

(58) Field of Classification Search
CPC combination set(s) only.
See application file for complete search history.

(56) References Cited

U.S. PATENT DOCUMENTS

| | | | |
|---|---|---|---|
| 2007/0031441 A1* | 2/2007 | Collins | ..................... A61P 9/10 424/184.1 |
| 2010/0035848 A1 | 2/2010 | Donahue et al. | |
| 2011/0045071 A1 | 2/2011 | Hematti et al. | |
| 2011/0268752 A1 | 11/2011 | Riley et al. | |
| 2013/0197051 A1 | 8/2013 | Muller et al. | |
| 2013/0197052 A1 | 8/2013 | Bandyopadhyay et al. | |

(Continued)

FOREIGN PATENT DOCUMENTS

| | | | |
|---|---|---|---|
| WO | 2013/181746 A1 | 12/2013 | |
| WO | WO-2016141108 A1 * | 9/2016 | .............. A61P 29/00 |

OTHER PUBLICATIONS

Hajam et al., "Bacterial Ghosts of *Escherichia coli* Drive Efficient Maturation of Bovine Monocyte-Derived Dendritic Cells," Dec. 15, 2015.*

(Continued)

*Primary Examiner* — Jared Barsky
(74) *Attorney, Agent, or Firm* — Christensen O'Connor Johnson Kindness PLLC

(57) ABSTRACT

The disclosure provides methods and compositions for affecting the development of antigen presenting cell (APC, e.g., a macrophage or dendritic cell). The methods include maturing an APC, promoting anti-inflammatory phenotype, promoting development of a T regulatory cell (Treg) from a naive T cell. The methods generally include exposing an APC to a tryptophan derived microbiota metabolite (TDMM), such as an anti-inflammatory or pro-mucosal TDMM, and permitting the APC to mature. In some embodiments, the conditioned APC is exposed to a naive T cell to further promote development of a T regulatory cell (Treg). In some embodiments, the TDMM is selected from the group consisting of indole, indole-3-acetate, 5-hydroxyindole, and indole-3-pyruvate.

21 Claims, 20 Drawing Sheets
Specification includes a Sequence Listing.

(56) References Cited

U.S. PATENT DOCUMENTS

| | | |
|---|---|---|
| 2014/0017313 A1 | 1/2014 | Coulter et al. |
| 2015/0258151 A1 | 9/2015 | Mani et al. |
| 2015/0361397 A1 | 12/2015 | Lee et al. |

OTHER PUBLICATIONS

Berstad, "Indole—the scent of a health 'inner soil'," Microb Ecol Health Dis. 2015;26.*
Vossenkämper et al., "Always one step ahead: How pathogenic bacteria use the type III secretion system to manipulate the intestinal mucosal immune system," Journal of Inflammation vol. 8, Article No. 11 (2011).*
Hubbard et al., "Adaption of the human aryl hydrocarbon receptor to sense microbiota-derived indoles," Mar. 19, 2015.*
Wei et al., "An aryl hydrocarbon receptor ligand acts on dendritic cells and T cells to suppress the Th17 response in allergic rhinitis patients," Laboratory Investigation (2014) 94, 528-535.*
Nguyen et al., "The roles of aryl hydrocarbon receptor in immune responses," International Immunology, vol. 25, No. 6, pp. 335-343 (Apr. 11, 2013).*
Bansal, T., et al., "The Bacterial Signal Indole Increases Epithelial-Cell Tight-Junction Resistance and Attenuates Indicators of Inflammation," Proceedings of the National Academy of Sciences of the USA (PNAS) 107(1):228-233, Jan. 2010.
Extended European Search Report dated Oct. 23, 2019, issued in European Application No. 17767652.5, filed Mar. 17, 2017, 6 pages.
Syer, S.D., and J.L. Wallace, "Environmental and NSAID-Enteropathy: Dysbiosis as a Common Factor," Current Gastroenterology Reports 16:377, 2014, 6 pages.
Zelante, T., et al., "Tryptophan Catabolites From Microbiota Engage Aryl Hydrocarbon Receptor and Balance Mucosal Reactivity via Interleukin-22," Immunity 39:372-385, Aug. 2013.
Extended European Search Report dated Apr. 9, 2020, in corresponding European Patent Application No. 17767631.9, filed Mar. 17, 2017, 8 pages.
Riley, J.L., et al., "Human T Regulatory Cell Therapy: Take a Billion or So and Call Me in the Morning," Immunity 30(5):656-665, May 2009.
Rouse, M., et al., "Indoles Mitigate the Development of Experimental Autoimmune Encephalomyelitis by Induction of Reciprocal Differentiation of Regulatory T Cells and Th17 Cells," British Journal of Pharmacology 169(6):1305-1321, 2013.
Singh, N.P., et al., "Dietary Indoles Suppress Delayed-Type Hypersensitivity by Inducing a Switch From Proinflammatory Th17 Cells to Anti-Inflammatory Regulatory T Cells Through Regulation of MicroRNA," The Journal of Immunology 196(3):1108-1122, Dec. 2015.
Steinmeyer, S., et al., "Empirical Modeling of T Cell Activation Predicts Interplay of Host Cytokines and Bacterial Indole," Biotechnology and Bioengineering 114(11):2660-2667, Nov. 2017.
Benson, J.M., and D.M. Shepherd, "Dietary Ligands of the Aryl Hydrocarbon Receptor Induce Anti-Inflammatory and Immunoregulatory Effects on Murine Dendritic Cells," Toxicological Sciences 124(2):327-338, 2011.
Extended European Search Report dated Dec. 4, 2019, issued in corresponding European Application No. 17767656.6, filed Mar. 17, 2017, 9 pages.
Sridharan, G.V., et al., "Prediction and Quantification of Bioactive Microbiota Metabolites in the Mouse Gut," Nature Communications 5(5492), Nov. 2014, 14 pages.
Sridharan, G.V., et al., "Prediction and Quantification of Bioactive Microbiota Metabolites in the Mouse Gut," Supplementary Information: Nature Communications 5(5492), Nov. 2014, 12 pages.
Wang, C., et al., "Activation of the Aryl Hydrocarbon Receptor Affects Activation and Function of Human Monocyte-Derived Dendritic Cells," Clinical and Experimental Immunology 177:521-530, 2014.
Yeste, A., et al., "Nanoparticle-Mediated Codelivery of Myelin Antigen and a Tolerogenic Small Molecule Suppresses Experimental Autoimmune Encephalomyelitis," Proceedings of the National Academy of Sciences of the USA (PNAS) 109(28):11270-11275, Jul. 2012.
First Examination Report dated Jun. 29, 2020, in corresponding Indian Patent Application No. 201817035033, filed Sep. 17, 2018, 12 pages.
Aliberti, J., "Immunity and Tolerance Induced by Intestinal Mucosal Dendritic Cells," Mediators of Inflammation 2016, Epub Feb. 2016, pp. 1-8.
Barbi, J., et al., "Treg Functional Stability and Its Responsiveness to the Microenvironment," Immunol. Rev. 259(1):115-139, May 2014.
Jin, U.-U., et al., "Microbiome-Derived Tryptophan Metabolites and Their Aryl Hydrocarbon Receptor-Dependent Agonist and Antagonist Activities," Mol Pharmacol. 85(5):777-788, May 2014.
Katepalli, M., et al., "The Microbiota-Derived Signal Indole Regulates T-Cell Fate by Reciprocal Control of Th17 and Treg Development (P3178)," J Immunol 190 (1 Supplement) 61.14, May 2013, 2 pages.
Lebeaux, D., et al., Biofilm-Related Infections: Bridging the Gap Between Clinical Management and Fundamental Aspects of Recalcitrance Toward Antibiotics, MMBR Reviews 78(3):510-543, Sep. 2014.
Lee, J.-H., and J. Lee, "Indole as an Intercellular Signal in Microbial Communities," FEMS Microbiol Rev 34 (4):426-444, Dec. 2009.
Mani, et al., "Understanding and Modulating Mammalian-Microbial Communication for Improved Human Health," Annu Rev Pharmacol Toxicol. 54:559-580, 2014.
Mellor, A.L., and D.H. Munn, "IDO Expression by Dendritic Cells: Tolerance and Tryptophan Catabolism," Nature Rev Immnology 4(10):762-774, Oct. 2004.
Owen, J.L., et al., "Microbial Activation of Gut Dendritic Cells and the Control of Mucosal Immunity," Journal of Interferon & Cytokine Research 33(11):619-631, Nov. 2013.
Watanabe, N., et al., "Induced Treg Cells Augment the Th17-Mediated Intestinal Inflammatory Response in a CTLA4-Dependent Manner," PLoS One 11(3):e0150244, Mar. 2016, 18 pages.
Whitfield-Cargile, et al., "The Microbiota-Derived Metabolite Indole Decreases Mucosal Inflammation and Injury in a Murine Model of NSAID Enteropathy," Gut Microbes 7(3):246-261, Jul. 2016.
Yang, T.-H., et al., "Supplement of 5-hydroxytrptophan Before Induction Suppresses Inflammation and Collagen-Induced Arthritis," Arthritis Research & Therapy:17:364, 2015.
International Search Report and Written Opinion dated Aug. 28, 2017, in International Application No. PCT/US2017/022968, filed Mar. 17, 2017, 14 pages.
International Preliminary Report on Patentability dated Sep. 18, 2018, in International Application No. PCT/US2017/022968, filed Mar. 17, 2017, 11 pages.
International Search Report and Written Opinion dated Jul. 17, 2017, in International Application No. PCT/US2017/023024, filed Mar. 17, 2017, 20 pages.
International Preliminary Report on Patentability dated Sep. 18, 2018, in International Application No. PCT/US2017/023024, filed Mar. 17, 2017, 13 pages.
International Search Report and Written Opinion dated Jun. 21, 2017, in International Application No. PCT/US2017/023011, filed Mar. 17, 2017, 8 pages.
International Preliminary Report on Patentability dated Sep. 18, 2018, in International Application No. PCT/US2017/023011, filed Mar. 17, 2017, 7 pages.
Sasaki-Imamura, T., et al., "Production of Indole From I-Tryptophan and Effects of These Compounds on Biofilm Formation by *Fusobaterium nucleatum* ATCC 25586," Applied and Environmental Microbiology 76(13):4260-4268, Jul. 2010.
Communication Pursuant to Article 94(3) EPC, dated Feb. 22, 2021, issued in EP Application No. 17767656.6, filed Mar. 17, 2017, 4 pages.
Arpaia, N., et al., "Metabolites Produced by Commensal Bacteria Promote Peripheral Regulatory T Cell Generation," Nature 504(7480), Dec. 2013, 14 pages.

(56) References Cited

OTHER PUBLICATIONS

Atarashi, K., et al., "Induction of Colonic Regulatory T Cells by Indigenous *Clostridium* Species," Science 331(6015):337-341, Jan. 2011.

Coombes, J.L., et al., "A Functionally Specialized Population of Mucosal CD103+ DCs Induces Foxp3+ Regulatory T Cells Via a TGF-β and Retinoic Acid-Dependent Mechanism," The Journal of Experimental Medicine 204(8):1757-1764, Aug. 2007.

Coombes, J.L., et al., "Dendritic Cells in Intestinal Immune Regulation," Nature Reviews Immunology 8(6):435-446, Jun. 2008.

Frei, R., et al., "Microbiota and Dietary Interactions—An Update to the Hygiene Hypothesis?" European Journal of Allergy and Clinical Immunology 67(4):451-461, Apr. 2012.

Furusawa, Y., et al., "Commensal Microbe-Derived Butyrate Induces the Differentiation of Colonic Regulatory T Cells," Nature 504(7480):446-450, Dec. 2013.

Himmel, M.E., et al., "Regulatory T-Cell Therapy for Inflammatory Bowel Disease: More Questions Than Answers," Immunology 136(2):115-122, Jun. 2012.

Huttenhower, C. et al., "Structure, Function and Diversity of the Healthy Human Microbiome," Nature 486(7402):207-214, Jun. 2012.

Ishikawa, H., et al., "Effect of Intestinal Microbiota in the Induction of Regulatory CD25+ CD4+ Cells," Clinical and Experimental Immunology 153(1):127-135, May 2008.

Kau, A.L., et al., "Human Nutrition, the Gut Microbiome and the Immune System," Nature 474(7351):327-336, Jun. 2011.

Kim, H-P. and W.J. Leonard, "CREB/ATF-Dependent T Cell Receptor-Induced FoxP3 Gene Expression: A Role for DNA Methylation," The Journal of Experimental Medicine 204(7):1543-1551, Jul. 2007.

Methe, B.A., et al., "A Framework for Human Microbiome Research," Nature 486(7402):215-221, Jun. 2012.

Ohkura, N., et al., "T Cell Receptor Stimulation-Induced Epigenetic Changes and Foxp3 Expression Are Independent and Complementary Events Required for Treg Cell Development," Immunity 37(5)785-799, Nov. 2012.

Piñero-Fernandez, S., et al., "Indole Transport Across *Escherichia coli* Membranes," Journal Of Bacteriology 193(8):1793-1798, Apr. 2011.

Polansky, J.K., et al., "DNA Methylation Controls Foxp3 Gene Expression," European Journal of Immunology 38(6):1654-1663, Jun. 2008.

Sakaguchi, S., et al., "Regulatory T Cells and Immune Tolerance," Cell 133(5):775-787, May 2008.

Yamane, H., et al., "Early Signaling Events That Underlie Fate Decisions of Naive CD4+ T Cells Towards Distinct T-Helper Subsets," Immunological Reviews 252(1):12-23, Mar. 2013.

Zheng, Y., et al., "Role of Conserved Non-Coding DNA Elements in the Foxp3 Gene in Regulatory T-Cell Fate," Mature 463(7282):808-812, Feb. 2010.

\* cited by examiner

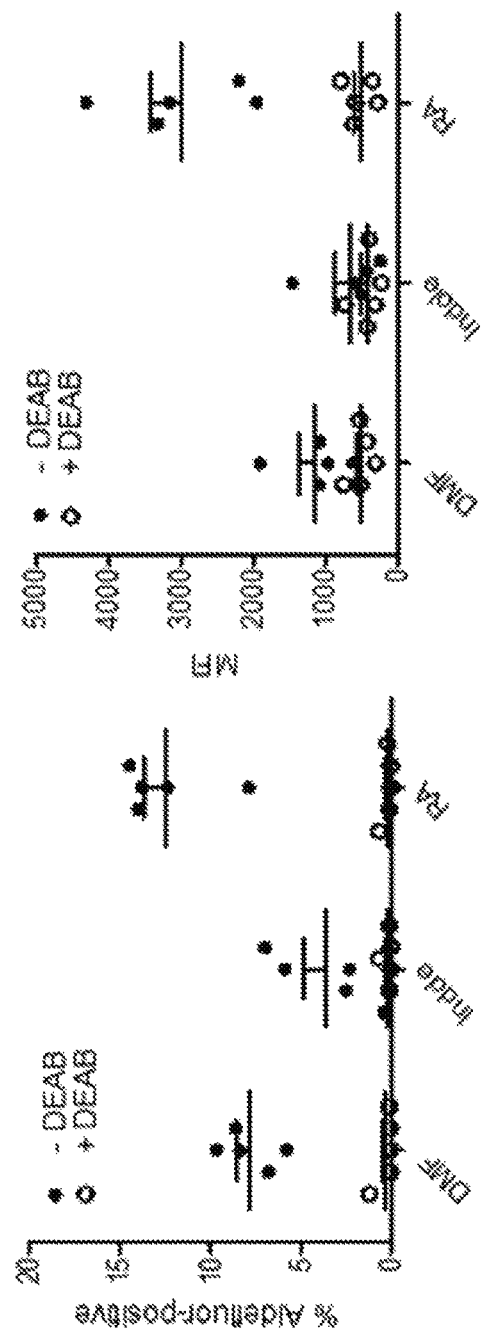
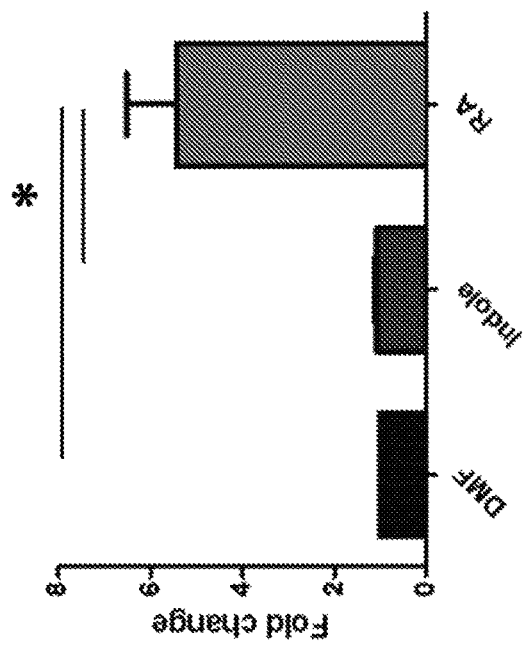
FIG. 13A
FIG. 13B

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial sequence
<220> FEATURE:
<223> OTHER INFORMATION: Synthetic

<400> SEQUENCE: 1
catggtatcc tccgcaatg                                                    19

<210> SEQ ID NO 2
<211> LENGTH: 21
<212> TYPE: DNA
<213> ORGANISM: Artificial sequence
<220> FEATURE:
<223> OTHER INFORMATION: Synthetic

<400> SEQUENCE: 2 gcgcattta ggcattgtaa c                                                  21

<210> SEQ ID NO 3
<211> LENGTH: 24
<212> TYPE: DNA
<213> ORGANISM: Artificial sequence
<220> FEATURE:
<223> OTHER INFORMATION: Synthetic

<400> SEQUENCE: 3
tcaactttcg atggtagtcg ccgt                                              24
```

```
<210> SEQ ID NO 4
<211> LENGTH: 24
<212> TYPE: DNA
<213> ORGANISM: Artificial sequence
<220> FEATURE:
<223> OTHER INFORMATION: Synthetic

<400> SEQUENCE: 4
tccttggatg tggtagccgt ttct                                            24
```

INDOLE REGULATION OF ANTIGEN PRESENTING CELLS

CROSS-REFERENCE(S) TO RELATED APPLICATION(S)

This application claims the benefit of Provisional Application No. 62/310,648, filed Mar. 18, 2016, Provisional Application No. 62/310,606, filed Mar. 18, 2016, Provisional Application No. 62/310,643, filed Mar. 18, 2016, and Provisional Application No. 62/310,630, filed Mar. 18, 2016, each of which is expressly incorporated herein by reference in its entirety.

STATEMENT OF GOVERNMENT LICENSE RIGHTS

This invention was made with Government support under GM106251 awarded by The National Institutes of Health, National Institute of General Medical Sciences; AI110642 awarded by The National Institutes of Health, National Institute of Allergy and Infectious Disease; A095788 awarded by The National Institutes of Health, National Institute of Allergy and Infectious Disease; and MCB-1120827, awarded by the National Science Foundation. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 57976_SEQ_Raw.txt. The text file is 2 KB; was created on Mar. 10, 2017; and is being submitted via EFS-Web with the filing of the specification.

BACKGROUND

The gastro-intestinal (GI) tract is a major interface between the body's immune system and the environment. Healthy function of the GI tract requires a proper balance of the immune system between tolerance to innocuous or beneficial non-self antigens and appropriate response to antigens that signal the presence of harmful pathogens. When the balance of tolerance and reactivity is upset, the subject can be susceptible to inappropriate inflammation and autoimmune disorders or to colonization and infection with pathogens.

Among the cell types present in the GI tract, antigen-presenting cells (APCs) are fundamental regulators of immunity which integrate signals from their local environment to direct immune responses in the context of antigen presentation to naïve T cells. APCs of the intestinal mononuclear phagocyte system have a unique role in maintaining homeostasis by promoting peripheral tolerance, a state of immune hyporesponsiveness towards harmless commensal microorganisms and nominal dietary components, which protects the host from aberrant inflammation. Mucosal dendritic cells (DCs) possess unique properties including preferential induction of regulatory T cells, antigen sampling across the intestinal epithelium, and promotion of gut-homing properties on lymphocytes. While tolerogenic APCs appear crucial for gut homeostasis and most evidence points to a local conditioning on DC and macrophage precursors after arrival from circulation into the mucosa, the gut-specific signals that mediate the acquisition of these properties remain incompletely understood.

Accordingly, despite advances and current understanding in the art, a need remains to decipher the mechanisms that drive immune-tolerance in the GI tract, and the provide compositions and methods to influence the tolerance of an individual to prevent inappropriate immune responses. The present disclosure addresses these and related needs.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the disclosure provides a method of maturing an antigen presenting cell (APC). The method comprises conditioning an immature APC with an effective amount of a tryptophan derived microbiota metabolite (TDMM), or a precursor, prodrug, or acceptable salt thereof, and permitting maturation of the APC. In one embodiment, the TDMM is selected from indole, indole-3-acetate, 5-hydroxyindole, and indole-3-pyruvate. In one embodiment, the APC is a dendritic cell. In one embodiment, the APC is a gut-associated lymphoid tissue (GALT) dendritic cell. In one embodiment, the APC is a macrophage. In one embodiment, the method further comprises exposing the immature APC to an antigen to which tolerance is desired. In one embodiment, the immature APC is conditioned with the TDMM in vitro. In one embodiment, the immature APC is conditioned with TDMM in vivo in a subject, and wherein the method further comprises administering an effective amount of TDMM, or a precursor or prodrug thereof, to the subject. In one embodiment, the administering an effective amount of the TDMM to the subject comprises increasing the production of the TDMM by the gut microbiota. In one embodiment, the mature APC exhibits an anti-inflammatory phenotype. In one embodiment, the method further comprises exposing the mature APC to a naïve T cell, in vivo or ex vivo.

In another aspect, the disclosure provides a method of promoting anti-inflammatory phenotype, comprising exposing an immature antigen presenting cell (APC) to a tryptophan derived microbiota metabolite (TDMM), or a precursor or prodrug thereof. In one embodiment, the TDMM is selected from indole, indole-3-acetate, 5-hydroxyindole, and indole-3-pyruvate. In one embodiment, the promoting anti-inflammatory phenotype comprises promoting peripheral tolerance of antigens in the gut of a subject. In one embodiment, the APC is a dendritic cell. In one embodiment, the APC is a mucosal dendritic cell. In one embodiment, the APC is a gut-associated lymphoid tissue (GALT) dendritic cell. In one embodiment, the APC is a macrophage. In one embodiment, the exposing an immature APC to the TDMM occurs in vitro. In one embodiment, the method further comprises administering the exposed APC to the subject. In one embodiment, the method further comprises exposing the mature APC to a naïve T cell in vivo. In one embodiment, the exposing an immature APC to the TDMM occurs in vivo in a subject and the method further comprises administering an effective amount of TDMM, or a precursor or prodrug thereof, to the subject. In one embodiment, the administering an effective amount of TDMM to the subject comprises increasing the production of the TDMM by the gut microbiota.

In another aspect, the disclosure provides a method of promoting development of a T regulatory cell (Treg) from a naïve T cell, comprising exposing the naïve T cell to an antigen presenting cell (APC) that has been conditioned with a tryptophan derived microbiota metabolite (TDMM), or a precursor or prodrug thereof. In one embodiment, the the TDMM is selected from indole, indole-3-acetate, 5-hydroxyindole, and indole-3-pyruvate. In one embodiment, the Treg has an increased FoxP3 expression as compared to the naïve T cell. In one embodiment, the APC is conditioned with the TDMM in vitro or ex vivo. In one embodiment, the TDMM-conditioned APC is produced by exposing an immature APC to the TDMM and permitted to mature. In one embodiment, the APC is a dendritic cell or macrophage. In one embodiment, the dendritic cell is a gut-associated lymphoid tissue (GALT) dendritic cell. In one embodiment, the Treg is produced in vitro and is administered to a subject in need.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 6A shows representative MFIs from one experiment of three. FIG. 6B shows mean percentage of phospho-Stat3-positive DCs from four independent experiments. *$p<0.05$ by Student's t test comparing indole-treated DCs to solvent control (DMF) at indicated timepoints.

FIG. 12A shows data reported as percentage of surface marker-expressing DCs and FIG. 12B shows data corresponding MFI values. Mean of three independent experiments. * indicates $p<0.05$ for one-way ANOVA followed by Dunnett's post-test.

FIGS. 13A and 13B graphically illustrate that indole does not induce aldehyde dehydrogenase activity in DCs. FIG. 13A: BMDCs were cultured from day 3 with indole (1 mM), retinoic acid (1 uM), or DMF control were assayed for aldehyde dehydrogenase (ALDH) activity using the Aldefluor commercial kit. The ALDH inhibitor, DEAB reagent, was included to control for background fluorescence. Aldefluor fluorescence as a measure of ALDH activity was analyzed by flow cytometry. Data is reported as percentage of Aldefluor positive DCs (left panel) and corresponding MFI values (right panel). Individual dots represent data from five independent experiments. FIG. 13B: Gene expression of aldh1a2 was assayed by real-time qPCR in day 7 BMDCs cultured with indole from day 3. Gene expression was normalized to 18 s ribosomal RNA. Mean of three independent experiments. *$p<0.05$ by Student's t test.

DETAILED DESCRIPTION

Figure 1:
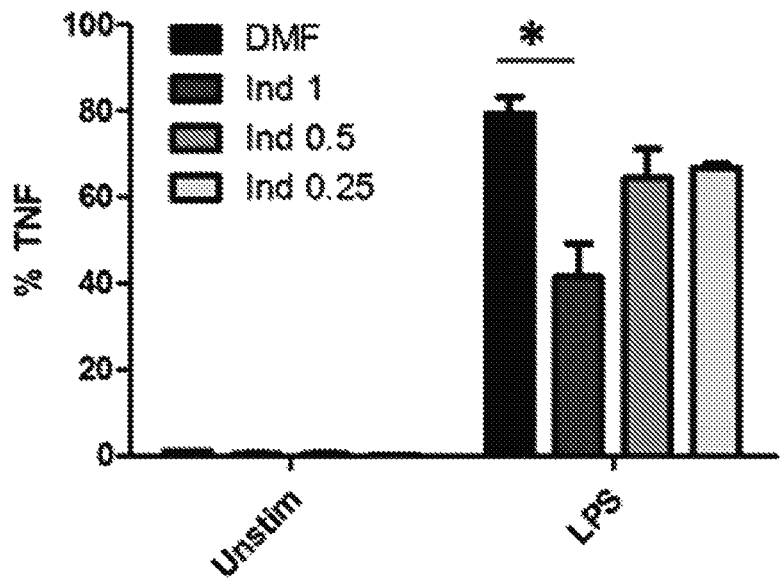
FIG. 1 graphically illustrates that overnight indole treatment inhibits TNF production in DC2.4 cell line. Flow cytometric analysis was performed on DC2.4 cells treated with indole for 24 hours and stimulated with LPS (1 ug/ml) or HK-STM ($2\times10^5$ CFU) for 4 hours in the presence of Golgiplug protein transport inhibitor. Intracellular staining was performed to assess TNF production. The mean of three independent experiments is shown. *$p<0.05$ by Student's t test comparing indole-treated DCs to solvent control (DMF).

More than $10^{14}$ microorganisms, collectively known as the microbiota, co-exist with the host and colonize the human gastrointestinal tract. The microbiota has profound effects on host immune development and function; however, the discrete mechanisms which mediate these effects are unclear. Extensive research has revealed the necessity of the microbiota for developing a fully functional intestinal and systemic immune system. While definitive crosstalk between host microbiota and immune system exists, the discrete compounds responsible for altering immune cell function remain to be fully characterized. Indeed the best characterized gut-tropic immune modulators, retinoic acid (RA) and TGFβ, are derived from the host. Few microbiota-derived signals have been reported to regulate the host's antigen presenting cells (APCs). Thus, the identification of additional microbiota-derived factors affecting APC phenotype and function in the gut would indeed be novel and of great utility. Primary roles of APCs include antigen presentation to naïve T cells, tissue integrity maintenance, and cytokine secretion to instruct activity of other immune cells. APCs residing at mucosal sites have a unique role in maintaining homeostasis by promoting peripheral tolerance to harmless commensal microorganisms. The dysregulation of this phenomenon promotes chronic inflammation in the intestinal tract, which predisposes the host to numerous cancers and metabolic disorders. Identifying and manipulating the specific microbiota components that drive tolerance in the gastrointestinal tract is a primary goal of current immunological research.

The present inventors have embarked on a study of microbiota metabolites to determine what microbiota-derived signaling factors might mediate immune responses or tolerance through the host APCs. As described in more detail below, the inventors first assessed the effect of a tryptophan derived microbiota metabolite (TDMM), indole, on the host APC development and function. As described throughout the project description, indole is able to suppress pro-inflammatory responses and promote mucosal phenotype and function in APCs. Remarkably, indole-conditioned dendritic cells (DCs) imprinted naïve T cells with gut-homing markers and preferentially induced regulatory T (Treg) cells. These findings reveal that indole conditions DCs towards a mucosal phenotype in a manner mechanistically distinct from the canonical GI signal, retinoic acid. In addition, indole-conditioned DCs are shown to be capable of promoting a regulatory phenotype in naïve T cells. These observations reveal a novel mechanism by which an endogenous microbiota metabolite conditions APCs for optimal function in mucosal tissues, thus providing evidence for a single metabolite promoting properties associated with peripheral tolerance. This revelation also paves the way for manipulating the microbiota for therapeutic potential in autoimmune and inflammatory disorders of the GI tract. In view of the effects of indole on APC development and its capacity to suppress pro-inflammatory responses, the inventors tested additional TDMM's for similar properties.

In accordance with the foregoing, in one aspect the present disclosure provides a method of maturing an antigen presenting cell (APC). The method comprises conditioning an immature APC with an effective amount of a tryptophan derived microbiota metabolite (TDMM), or a precursor or prodrug thereof, and permitting maturation of the APC.

As used herein, the term "tryptophan derived microbiota metabolite" ("TDMM") refers to metabolites produced by microorganisms of the commensal microbiota that resides in the intestinal tract. In some contexts, the TDMM inhibits or suppresses pro-inflammatory responses or, alternatively, promote mucosal function, and thus can be referred to as "anti-inflammatory" or "pro-mucosal" TDMM so as to distinguish from TDMMs that do not exhibit the same properties on APCs. This functional capacity can be readily established according to the exemplary approaches and protocols described in more detail below. The individuals of the microbiota inhabit the space of the intestines and exist in homeostasis with the healthy vertebrate host. Thus, presumably, the metabolite products produced by the individuals of the microbiota have been selected over time to avoid triggering inflammatory immune responses in the mucosa. The specific metabolites referred to by the term TDMM are derivatives of tryptophan and include compounds such as indole, hydroxyindole (e.g., 2-hydroxyindole, 3-hydroxyindole, 5-hydroxyindole, 7-hydroxyindole), 1-(2-carboxyphenylamino)-1-deoxy-D-ribulose-5-phosphate, 5-Hydroxy-L-tryptophan, Indoleglycerol phosphate, indolepyruvate, N-(5-Phospho-D-ribosyl)anthranilate, tryptamine, indole-3-acetate, L-formylkynurenine, L-Tryptophanyl-tRNA(Trp), indole-3-acetamide, indole-3-pyruvate, indole-3-lactic acid, tryptophan, indole-3-acetaldehyde, indole-3-aldehyde, isatin (indole-2,3-dione), isoindigo, indirubin, indoxyl-sulfate, and 2-oxyindole. Many of these are being shown to be AhR ligands, which as demonstrated in the present disclosure relating to indole, has a role in Treg/Th17 differentiation. The TDMM encompasses such molecules that have been directly obtained from microbiota individuals. Such TDMMs can be isolated, purified, or partially purified through well-established methods. However, the term TDMM, while referring to the feature of a "microbiota metabolite," is not necessarily limited to the specific source as one or more individual organisms of the commensal microbiota. Instead, it merely refers to the fact that the commensal microbiota are known to produce such a compound. Thus, the TDMM used as part of this disclosure can also be obtained from an organism that is not typically considered to be a member of a commensal microbiota of a vertebrate organism (whether the vertebrate individual is the source of the naïve T cell or not). Instead, the TDMM can be produced by known methods, such as typical recombinant approaches, in preferred laboratory strains of bacteria, and the like. Furthermore, the TDMM can be produced synthetically, as appropriate through known methods of synthetic chemistry.

In one embodiment, the TDMM is selected from indole, indole-3-acetate (I3AT), 5-hydroxyindole (5HI), and indole-3-pyruvate (I3P). In a specific embodiment, the TDMM is indole. In one embodiment, the TDMM is indole, which is typically represented with the following structure:

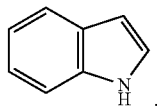

In any of the above embodiments, the antigen presenting cell (APC) can be conditioned with a TDMM composition that is a precursor to or prodrug of any of the above listed compound embodiments such that the precursor will eventually lead to exposure of the APC to the listed compound.

For any embodiment, it can be readily determined the minimal or sufficient amount of TDMM required to affect maturation of the APC. For example, as described in more detail below, illustrative assays can run to determine the effect of TDMMs on the activation of APCs using 0.01 to 5.0 mM of the TDMM in the culture medium. For example, illustrative, non-limiting amounts of TDMM to affect maturation of the APC can be 0.01, 0.025, 0.5, 0.075, 0.1, 0.25, 0.5, 0.75, 1.0, 1.25, 1.5, 1.75, 2.0, 2.25, 2.5, 2.75, 3.0, 3.25, 3.5, 3.75, 4.0, 4.25, 4.5, 4.75, 5.0 and more, or any value in between.

The APC can be a dendritic cell (DC) or macrophage. In some embodiments, the dendritic cell is a mucosal or gut-associated lymphoid tissue (GALT)

In some embodiments, the method also comprises exposing the APC to an antigen. The antigen can be one to which immune tolerance is desired.

The conditioning step can be performed in vitro or in vivo. In vitro methodologies for maintaining and manipulating live APCs are known. See below for exemplary methods.

Embodiments where the conditioning is performed in vivo further comprise a step of administering TDMM or TDMM precursor (e.g., indole or an indole precursor such as tryptophan) to the subject. Administration can be through any known and acceptable route, such as by intra-peritoneal (IP), intravenous (IV), topical, parenteral, intradermal, transdermal, oral (e.g., via liquid or pill), rectal, or respiratory (e.g., intranasal mist) routes. In preferred embodiments, the TDMM is ingested, e.g., via liquid or pill, etc., to facilitate delivery of the TDMM to the intestinal tract where the microbiota reside. In other embodiments, the microbiota of the subject is induced to produce elevated levels of the indole. In this regard, additional microbiota organisms that are known to produce high levels of the TDMM can be administered to the subject. In some embodiments, the administered microbiota organisms can be artificially selected or genetically engineered to produce higher levels of the TDMM when residing in the GI tract of the subject. For example, in some embodiments, the genetically engineered microorganisms are engineered to express, stably or transiently, higher levels of a tnaA gene, which encodes the enzyme responsible for tryptophan metabolism and production of indole. Alternatively or additionally, the subject can be provided with elevated levels of tryptophan, such as in dietary supplements, so as to allow the microbiota to produce higher levels of the TDMM, such as indole.

As described below in more detail, mature APCs that have been conditioned with TDMMs (e.g., indole) exhibit anti-inflammatory functionality, inhibition (i.e., reduced expression) of pro-inflammatory cytokines such as TNF, IL-6, and IL-12. Furthermore, the mature APCs promote the development of Treg (FoxP3+) cells from naïve T cells while inhibiting development of naïve T cells into other, pro-inflammatory lineages of mature T cells.

In another aspect, the disclosure provides a method of promoting anti-inflammatory phenotype. The method comprises exposing an immature antigen presenting cell (APC) to an anti-inflammatory (or pro-mucosal) TDMM, or a precursor thereof. In this regard, "promoting anti-inflammatory phenotype" can include promoting peripheral tolerance of antigens in the gut of a subject and/or avoiding or reducing the likelihood of an inflammatory response, in general or to an antigen of interest.

TDMMs are described above. In specific embodiments, the anti-inflammatory or pro-mucosal TDMM is selected from indole, indole-3-acetate (I3AT), 5-hydroxyindole (5HI), and indole-3-pyruvate (I3P). In a specific embodiment, the TDMM is indole.

APCs are described above. Elements relating to the exposure or conditioning of the immature APC with indole are also described above. APCs that have been exposed to indole can be administered to a subject for therapeutic effect (i.e., to inhibit an anti-inflammatory environment or phenotype). Alternatively, the indole-conditioned APCs can be exposed to naïve T cells in vitro to promote the development into Fox3P+ Treg cells. The Treg cells can be administered to the subject in need to promote immunotolerance and inhibit inflammatory conditions.

In another aspect, the disclosure provides a method of promoting development of a T regulatory cell (Treg) from a naïve T cell. In one embodiment, the method comprises exposing the naïve T cell to an antigen presenting cell (APC) that has been conditioned with indole. Tregs and the indole-conditioning of APCs is described in more detail above and illustrated below.

Any aspect described above can be applied in a method to treat diseases or conditions that exhibit excessive or inappropriate immune responses, such as excessive or inappropriate inflammation. Such diseases or conditions include, but are not limited to allergies, inflammatory bowel disease (IBD), colitis, NSAID-enteropathy/ulceration, psoriasis, rheumatoid arthritis, graft-versus-host disease, lupus, multiple sclerosis, and the like.

The inventors have also shown that TDMMs, such as indole, attenuate *Salmonella Typhimurium* (*Salmonella*) virulence and invasion, as well as increases the colonization resistance of host cells to *Salmonella* colonization. Briefly, *Salmonella* exposed to indole was less competitive in colonizing mice compared to solvent-treated controls. In agreement with the reduced in vivo competitiveness, indole decreased *Salmonella* invasion of HeLa epithelial cells by 160-fold and that of J774.A1 macrophages by 2-fold. However, the intracellular survival of *Salmonella* in J774.A1 macrophages was not significantly affected by indole. The observed decrease in invasion was corroborated by a decrease in expression of four *Salmonella* Pathogenicity Island-1 (SPI-1) genes studied that are involved in invasion. Isogenic mutant studies also showed that the effect of indole was not dependent on sdiA and partially mediated through the phoPQ regulon. *Salmonella* invasion of indole-treated HeLa cells was also reduced by 70%, suggesting that indole also increases colonization resistance of epithelial cells. Lastly, indole synergistically enhanced the effect of short chain fatty acids on attenuation of SPI-1 gene expression. Together, these results demonstrate that indole is an important microbiota metabolite that has direct anti-infective effects on *Salmonella* and host cells.

Thus, in some embodiments, the disclosure provides a method of inhibiting infectivity of gut epithelia by *Salmonella* in a subject in need thereof, comprising administering to the subject an effective amount of a tryptophan derived microbiota metabolite (TDMM). In other embodiments, the disclosure provides a method of enhancing resistance of gut epithelia to *Salmonella* infection in a subject in need thereof, comprising administering to the subject an effective amount of a tryptophan derived microbiota metabolite (TDMM).

In one embodiment, the subject has been exposed to, or is at risk of being exposed to, *Salmonella*. In one embodiment, the TDMM is indole, tryptamine, indole acetate, or indole pyruvate. In one embodiment, the TDMM is administered by intra peritoneal (IP), intravenous (IV), topical, parenteral, intradermal, transdermal, oral (e.g., via liquid or pill), or respiratory (e.g., intranasal mist) routes. In one embodiment, the subject is a mammal, such as a human or rodent. In one embodiment, the inhibited infectivity of the *Salmonella* can be characterized by a reduced expression of hilA in the *Salmonella*. In one embodiment, the method further comprising administering to the subject an effective amount of one or more short chain fatty acids (SCFAs). In one embodiment, the SCFA is acetate, or propionate. In one embodiment, the TDMM and SCFA are co-administered to the subject.

As used herein, the term "treating" means preventing, reducing, slowing, or ameliorating symptoms associated with the indicated condition. For example, the present methods preventing, reducing, inhibiting, or ameliorating inflammation that may be experienced by a subject. The conditioning of endogenous DC's and/or administration of DC's conditioned in vitro/ex vivo, as described herein, can be applied to mediate such a treatment for the prevention, reduction, inhibition, or amelioration of inflammation that characterizes a particular disorder or disease.

In another aspect, the disclosure provides a pharmaceutical composition comprising at least one TDMM, or precursor or prodrug thereof, as described above. If derived from microbiota or a bacterial source, the TDMM is preferably isolated or substantially isolated from the bacterial source. Alternatively, the TDMM may be synthesized using appropriate biochemistry where appropriate, and combined with excipients or other additives to enhance stability, function, or tolerability (reduced toxicity).

In some embodiments, the pharmaceutical composition also comprises at least one SCFA. Exemplary SCFA's include acetate and propionate.

The pharmaceutical composition can be formulated appropriately using routine and conventional aspects of the art for appropriate routes of administration. Exemplary routes of administration appropriate for the contemplated applications include intra peritoneal (IP), intravenous (IV), topical, parenteral, intradermal, transdermal, oral (e.g., via liquid or pill), and respiratory (e.g., intranasal mist) routes.

Formulations include encapsulation technologies including incorporation into liposomes, nanoparticles, microparticles, and other standard formulations for delivery including targeted delivery, according to known techniques.

Alternatively, the disclosure provides kits comprising at least one TDMM, or precursor or prodrug thereof, as described herein, useful for in vitro applications of maturing APCs, as described above. The kits can further comprise written indicia for instructing proper APC culture and maturation, relevant media, and the like, to further facilitate culture and maturation of APCs and related applications.

In the kits or composition, the TDMM, and potentially other active agents, can be formulated as pharmaceutically acceptable compositions or preparations. Such compositions or preparations can routinely contain pharmaceutically acceptable carriers, concentrations of salt, buffering agents, preservatives, other immune modulators, and optionally other therapeutic ingredients. The term "pharmaceutically-acceptable carrier" as used herein, means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions also are capable of being comingled with active agents of the present invention, in a manner such that there is no interaction which would substantially impair the desired pharmaceutical efficacy.

Unless specifically defined herein, all terms used herein have the same meaning as they would to one skilled in the art of the present invention. Practitioners are particularly directed to Sambrook J., et al. (eds.) *Molecular Cloning: A Laboratory Manual*, 3rd ed., Cold Spring Harbor Press, Plainsview, N.Y. (2001); Ausubel F. M., et al. (eds.), *Current Protocols in Molecular Biology*, John Wiley & Sons, New York (2010); and Coligan J. E., et al. (eds.), *Current Protocols in Immunology*, John Wiley & Sons, New York (2010) for definitions and terms of art.

The use of the term "or" in the claims is used to mean "and/or" unless explicitly indicated to refer to alternatives only or the alternatives are mutually exclusive, although the disclosure supports a definition that refers to only alternatives and "and/or."

Following long-standing patent law, the words "a" and "an," when used in conjunction with the word "comprising" in the claims or specification, denotes one or more, unless specifically noted.

Unless the context clearly requires otherwise, throughout the description and the claims, the words "comprise," "comprising," and the like, are to be construed in an inclusive sense as opposed to an exclusive or exhaustive sense; that is to indicate, in the sense of "including, but not limited to." Words using the singular or plural number also include the plural and singular number, respectively. Additionally, the words "herein," "above," and "below," and words of similar import, when used in this application, shall refer to this application as a whole and not to any particular portions of the application.

Disclosed are materials, compositions, and components that can be used for, can be used in conjunction with, can be used in preparation for, or are products of the disclosed methods and compositions. It is understood that, when combinations, subsets, interactions, groups, etc., of these materials are disclosed, each of various individual and collective combinations is specifically contemplated, even though specific reference to each and every single combination and permutation of these compounds may not be explicitly disclosed. This concept applies to all aspects of this disclosure including, but not limited to, steps in the described methods. Thus, specific elements of any foregoing embodiments can be combined or substituted for elements in other embodiments. For example, if there are a variety of additional steps that can be performed, it is understood that each of these additional steps can be performed with any specific method steps or combination of method steps of the disclosed methods, and that each such combination or subset of combinations is specifically contemplated and should be considered disclosed. Additionally, it is understood that the embodiments described herein can be implemented using any suitable material such as those described elsewhere herein or as known in the art.

Publications cited herein and the subject matter for which they are cited are hereby specifically incorporated by reference in their entireties.

The following is a description of a comprehensive study to assess the role of the tryptophan derived microbiota metabolite (TDMM), indole, on the host APC development and function. Presented in three sections, indole was shown in this study to suppress pro-inflammatory responses and promote mucosal phenotype and function in APCs. Moreover, it was shown that indole conditions dendritic cells (DCs) towards a mucosal phenotype in a manner mechanistically distinct from the canonical GI signal, retinoic acid, thus revealing a novel mechanism by which an endogenous microbiota metabolite conditions APCs for optimal function in mucosal tissues.

I. Indole Directly Confers Mucosal Properties Upon Dendritic Cells (DCs)

Overview

The factors responsible for conferring mucosal properties upon dendritic cells (DCs) in the GALT remain incompletely characterized. The role of indole as a potential signal for DCs activity and development was investigated. This study begins by addressing the direct influence of indole conditioning on DC phenotype and function. The following findings emerged: 1) indole selectively inhibits pro-inflammatory cytokine and signaling pathways in dendritic cells in an AhR-independent manner; 2) indole does not alter antigen-presenting cell properties of dendritic cells; and 3) indole induces homing markers on dendritic cells.

Rationale

The majority of gut-tropic immune modulators that have been reported are derived from the host. Retinoic acid and TGF-β have distinct roles in shaping antigen-presenting cells for mucosal function; however, neither of these signals is responsible for imprinting dendritic cells with all of the tolerogenic properties observed in the gut. Intestinal inflammation results in a loss of tolerogenic properties of mucosal DCs that cannot be rescued by adding endogenous RA to the system. This observation implicates additional mechanisms responsible for local conditioning of mucosal dendritic cells.

Results

Indole Selectively Inhibits Pro-Inflammatory Cytokine and Signaling Pathways in Dendritic Cells in an AhR-Independent Manner Pro-Inflammatory Cytokines One important way that DCs shape local immune responses is through the production of cytokines. Cytokine production was addressed in indole-conditioned dendritic cells, first using the murine dendritic cell line, DC2.4. Cells pre-treated with physiologically relevant doses of indole produced less TNF upon stimulation with the bacterial surface component and TLR4 ligand, LPS. Production of TNF was reduced by 50% following treatment with 1 mM indole (FIG. 1). This response is biologically important as LPS serves as the prototypical endotoxin, present on the surface of virtually all gram-negative bacteria including gut-resident commensal strains. Thus, these results demonstrate the ability of indole to tolerize DCs against a relevant, inflammatory bacterial signal.

Figure 2:
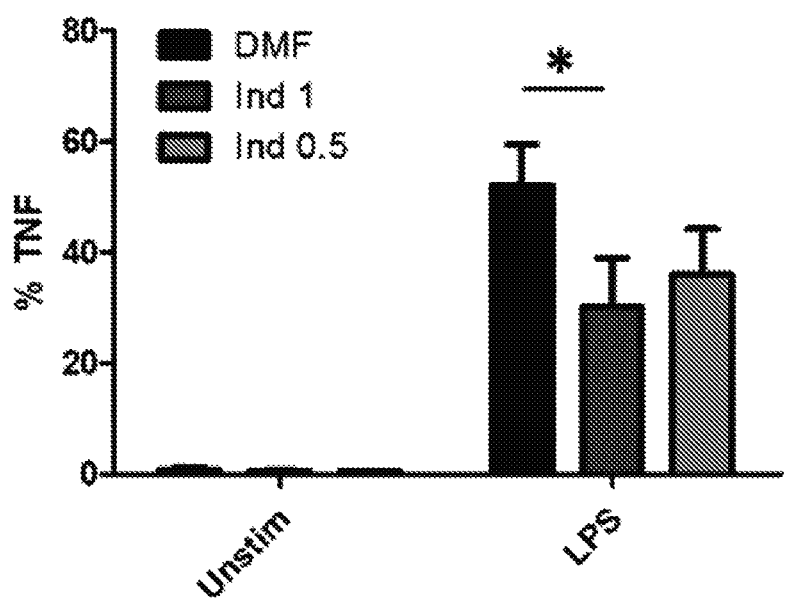
FIG. 2 graphically illustrates that overnight indole treatment inhibits TNF production in BMDCs. Flow cytometric analysis was performed on BMDCs treated with indole for 24 hours and stimulated with LPS (1 ug/ml) or HK-STM ($10^7$ CFU) for 4 hours in the presence of Golgiplug protein transport inhibitor. Intracellular staining was performed to assess TNF production. The mean of three independent experiments is shown. *$p<0.05$ by Student's t test comparing indole-treated DCs to solvent control (DMF).
Figure 3A:
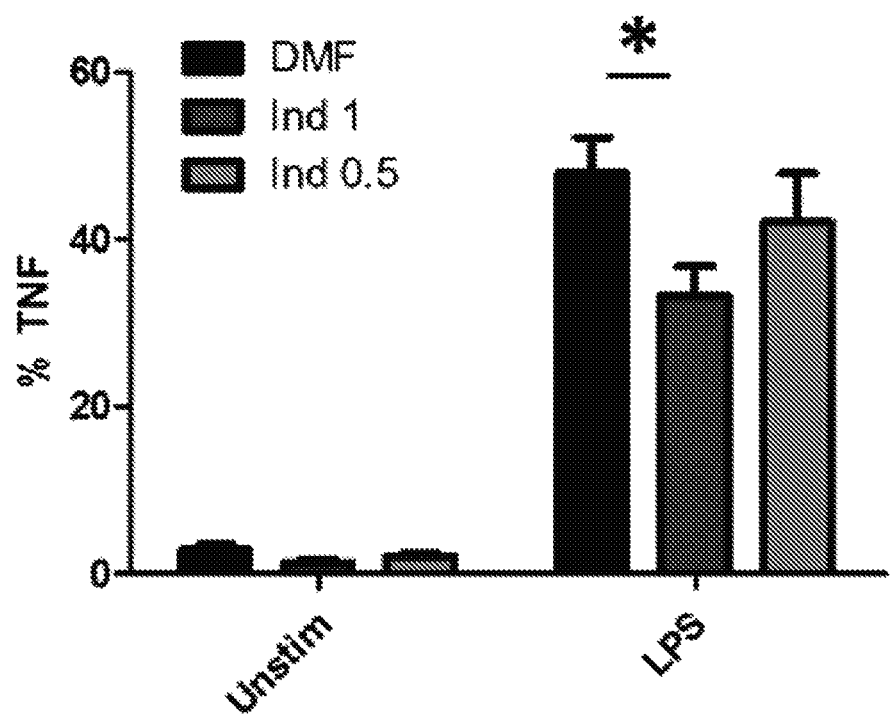
FIGS. 3A and 3B graphically illustrate that conditioning with indole during differentiation inhibits TNF and IL-12 production in BMDCs. Flow cytometric analysis was performed on BMDCs differentiated in the presence of indole from day 3 and then stimulated with LPS (1 ug/ml) for 4 hours in the presence of Golgiplug protein transport inhibitor. Intracellular staining was performed to assess TNF (FIG. 3A) and IL-12 (FIG. 3B) production. The mean of three independent experiments is shown. *$p<0.05$ by Student's t test comparing indole-treated DCs to solvent control (DMF).
Figure 3B:
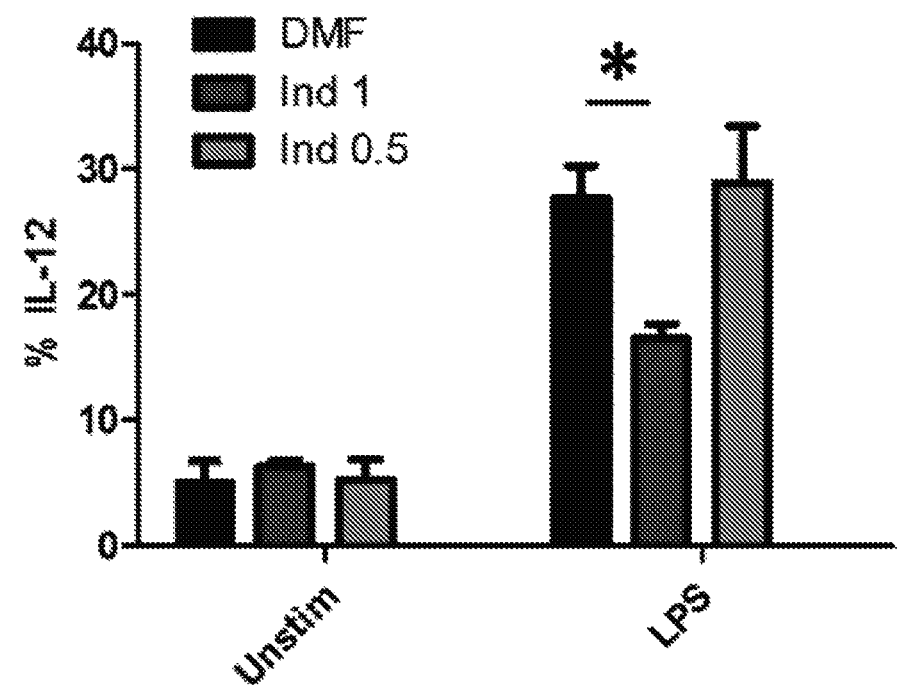

Next, bone marrow-derived DCs (BMDCs) were generated as described previously (Inaba K, et al. (1992) Generation of large numbers of dendritic cells from mouse bone marrow cultures supplemented with granulocyte/macrophage colony-stimulating factor. *The Journal of Experimental Medicine* 176(6):1693-1702). Briefly, bone marrow was harvested from femurs of mice and cultured for 7 days in the presence of DC-skewing cytokines, GM-CSF and IL-4. Treatment of these cultures with indole for 18 hours followed by TLR stimulation resulted in a similar inhibition of TNF production, reaching a magnitude of nearly 2-fold inhibition (FIG. 2). The pro-inflammatory cytokines, IL-6 and IL-12, were specifically queried. Flow cytometric analysis was performed on BMDCs treated with indole for 24 hours and stimulated with LPS (1 ug/ml) for 4 hours in the presence of Golgiplug protein transport inhibitor and the percentage of IL-12 and IL-6-producing DCs indicated, as determined by intracellular staining. The analysis revealed a 2-fold or greater inhibition of cytokine production with overnight indole treatment (not shown). Immune cells communicate largely through the production of soluble factors including cytokines, and DCs detect these signals and determine their effector functions accordingly. Thus, the inhibition of pro-inflammatory cytokine production induced by indole conditioning suggests that indole dampens DC responses to immunogenic signals, providing a potential mechanism by which mucosal DCs "ignore" harmless commensal bacteria in the gut.

The effect of indole on BMDC generation was investigated next. BMDCs exposed to indole from the third day of their 7 day culture also exhibited a statistically significant inhibition of pro-inflammatory cytokine production upon LPS stimulation (FIG. 9: 30% reduction in TNF and 40% reduction in IL-12, p<0.05). To confirm the relevance of these observations in primary cells, indole conditioning was investigated in splenic DCs ex vivo. Because indole is undetectable by mass spectrometry in peripheral tissues outside the gut, it is likely that splenic DCs are indole-naïve. Splenocytes isolated from C57BL6/J mice were treated with indole overnight, followed by stimulation with LPS or heat-killed *Salmonella typhimurium*.

Figure 4:
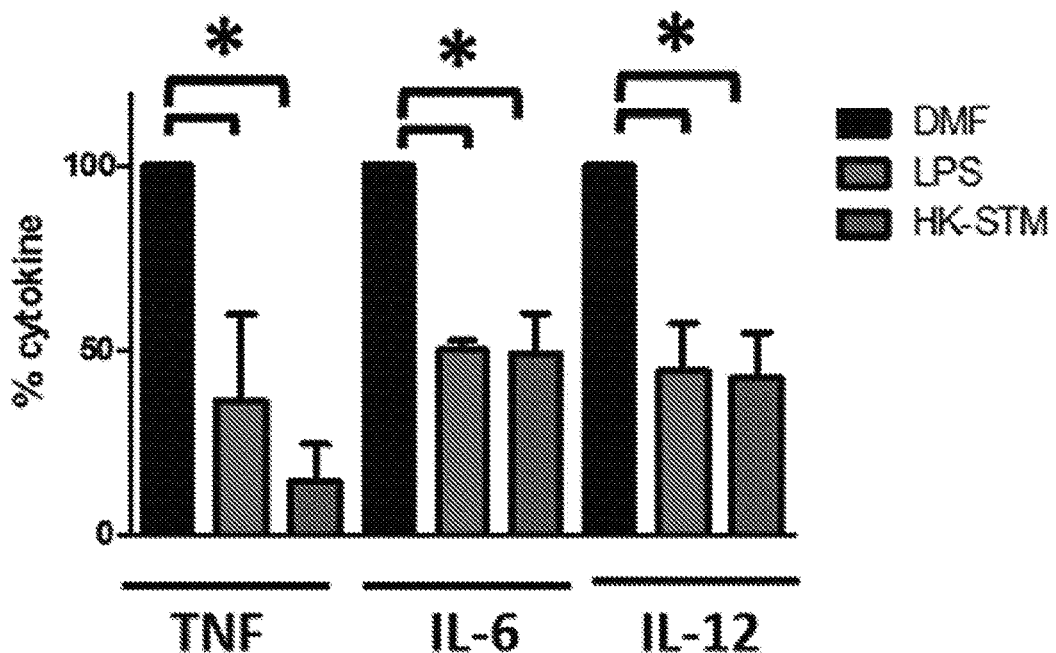
FIG. 4 graphically illustrates that indole conditioning inhibits pro-inflammatory cytokine production in splenic DCs ex vivo. Flow cytometric analysis were performed to detect cytokine production by indole-conditioned splenic DCs. Splenocytes were cultured for 24 hours with indole, then stimulated with LPS (5 ug/ml) or HK-STM ($4\times10^7$ CFU) for 6 hours in the presence of Golgiplug protein transport inhibitor. Cultures were then stained for CD11c and intracellular TNF, IL-6, and IL-12. Analysis was confined to CD11c+ DCs and maximal cytokine production was normalized to solvent control (DMF). The mean of three independent experiments is shown. *$p<0.05$ by Student's t test comparing indole-treated DCs to solvent control (DMF).

Production of pro-inflammatory cytokines in CD11c+ DCs was assessed via flow cytometry. A robust inhibition of 2-fold or greater magnitude in production of the cytokines TNF, IL-6, and IL-12 by indole-conditioned ex vivo splenic DCs was observed (FIG. 4). This confirmed the in vitro observations that indole inhibits pro-inflammatory cytokine production in DCs.

NF-kB

Figure 5:
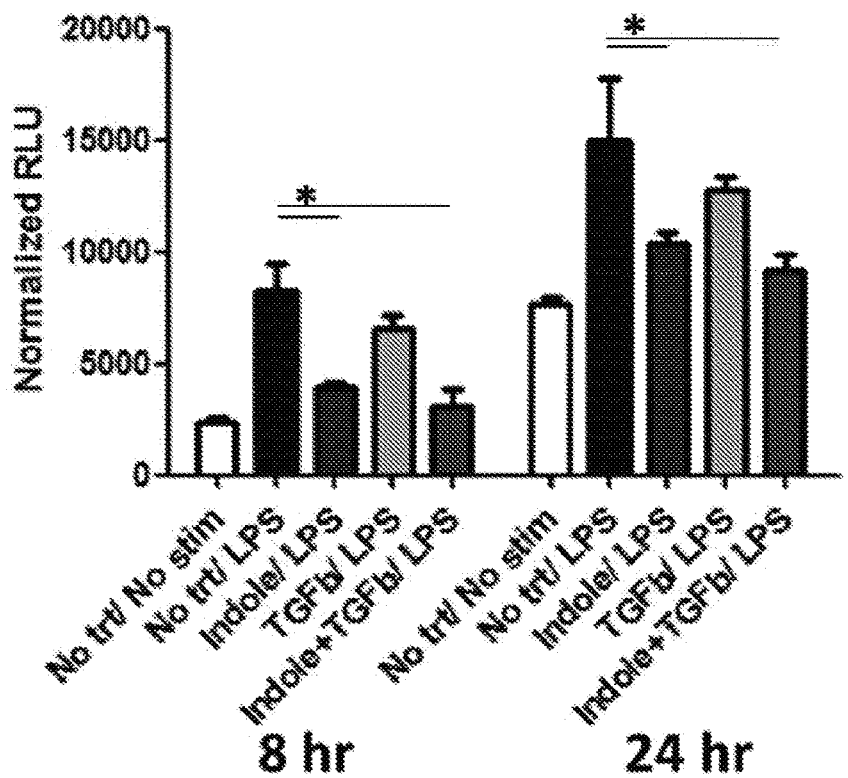
FIG. 5 graphically illustrates that indole inhibits NF-kB activity in DC2.4 cell line. DC2.4-NFkB-GLuc cells were treated with indole +/- TGF-β for 24 hours followed by LPS stimulation (10 ug/ml) for 8 or 24 hours. Supernatants were collected and assayed for GLuc concentration in terms of relative luminescence units (RLU). *$p<0.05$ by Student's t test comparing treated samples to untreated, LPS-stimulated sample.

The ubiquitous transcription factor NF-kB is a predominant upstream effector mediating numerous inflammatory signaling pathways (O'Mahony C, et al. (2008) Commensal-induced regulatory T cells mediate protection against pathogen-stimulated NF-κB activation. *PLoS Pathog* 4(8): e1000112). Thus, indole was investigated for any effect on this signaling pathway. Using a DC2.4 cell line transduced with a dual NF-kB reporter plasmid and a GLuc reporter, NF-kB activity was assayed subsequent to overnight treatment with indole. Many ligands can activate NF-kB including growth factors, cytokines, and certain viral and bacterial products. To maintain consistency with the cytokine studies, the bacterial surface molecule LPS were utilized to induce NF-kB activity. Indeed, NF-kB signaling was inhibited in indole-conditioned cells by approximately one-third (FIG. 5). This level of suppression was greater than that achieved with the positive control, TGFβ, and similar to concurrent treatment with both indole and TGF-β. The nuclear factor NF-kB pathway lies upstream and mediates transcription of many pro-inflammatory genes, including cytokines. Thus, the observed inhibitory effects of indole on pro-inflammatory cytokine production might be mediated at the level of NF-kB signaling.

Stat3

Based on the accumulating evidence that indole exerts a suppressive effect on inflammatory signaling in DCs, the potential effect of indole on host-derived pro-inflammatory signals was investigated via the Signal Transducer and Activator of Transcription 3 (Stat3) pathway. To date, seven Stat proteins have been identified, having dual roles as signaling proteins in the cytoplasm as well as nuclear transcription factors. The Stat family activates a diverse set of genes including those involved with growth, survival, and inflammatory processes. The biological importance of Stat3 is evidenced by the observation that it is the only Stat whose deficiency results in embryonic lethality. Persistent activation of Stats occurs frequently when an upstream receptor-associated Janus kinase (JAK) becomes overactive due to genetic or epigenetic factors. It is common for Stat3 to be overexpressed in a variety of human cancers, and a role for Stat3 hyperactivity in driving DCs towards a cancerous phenotype has been established. In addition, Stat3 is a necessary transcription factor for pro-inflammatory Th17 differentiation. The inventors have observed that indole inhibits the Th17 lineage. Thus, a reasonable hypothesis would be that suppression of Stat3 signaling by indole is a mechanism by which Th17 differentiation is suppressed.

Figure 6A:
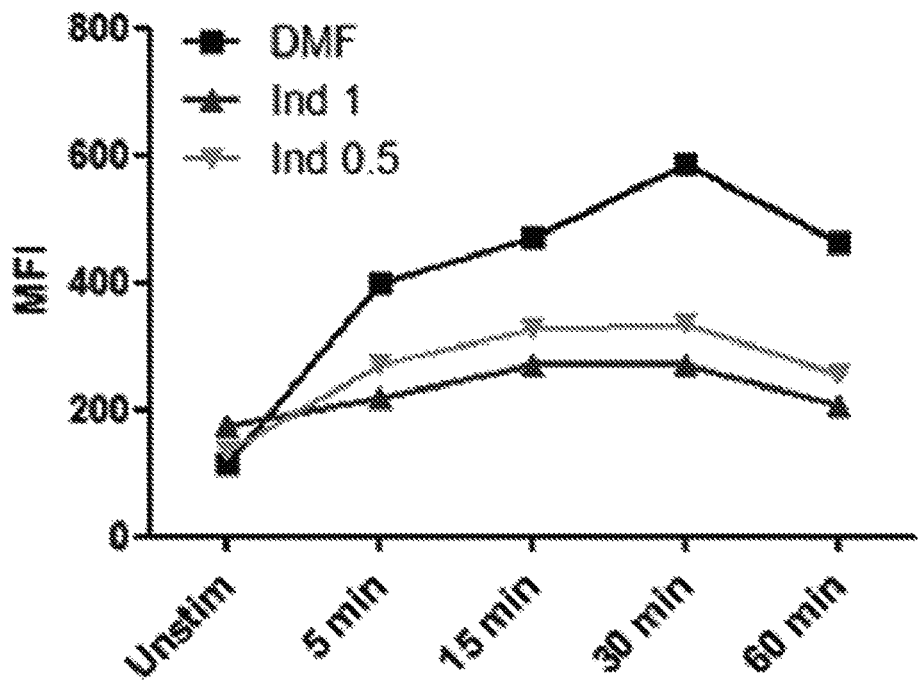
FIGS. 6A and 6B graphically illustrate that indole inhibits IL-6-induced pStat3 signaling in BMDCs. Flow cytometric analysis was performed on BMDCs conditioned with indole from day 3 of culture and subsequently stimulated with IL-6 (10 ng/ml) for the given times. Cells were stained for phospho-Stat3 and analyzed by flow cytometry.
Figure 6B:
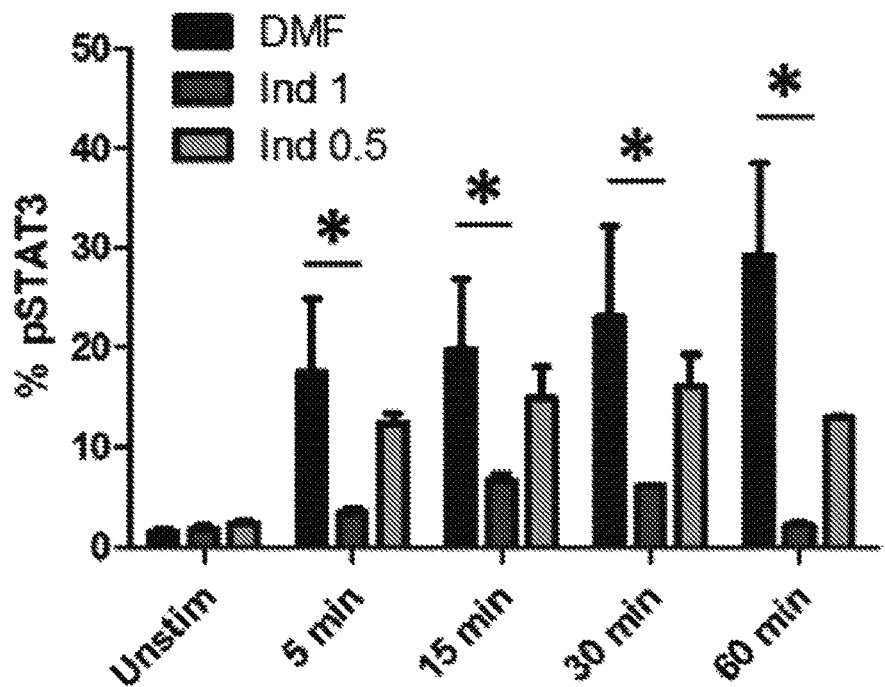

BMDCs were conditioned with indole from day 3 and then induced Stat3 signaling by stimulation with IL-6 (FIGS. 6A and 6B). While Stat3 has both a tyrosine (Y705) and serine (S727) activation site, tyrosine phosphorylation is mediated by Janus kinases and required for Stat3 nuclear localization and subsequent DNA binding. Thus, the phosphorylation site was queried for this study. In the absence of an external stimulus, phosphorylation of Stat3 was nearly undetectable across all conditions. Stat3 signaling was induced by the addition of IL-6, and substantial Stat3 phosphorylation (~18%) was observed in control DCs within 5 minutes of stimulation, lasting at least 60 minutes post-stimulation (peak of ~30% phosphorylated Stat3). The physiological concentration of 1 mM indole strongly inhibited Stat3 phosphorylation, with indole-treated DCs reaching peak phosphorylation of 8% at 15 minutes post-stimulation. Inhibition of Stat3 was observed not only in the percentage of DCs bearing phosphorylated Stat3 but also in the magnitude of phosphorylation on a per cell basis. The MFI values were similar between indole-treated DCs and controls in the absence of stimulation, but a 2-fold or greater suppression was observed in indole-DCs throughout the 60 minute timecourse under IL-6 stimulation. This finding is in agreement with the observation that indole inhibits the Th17 lineage and indicates that indole inhibits Stat3 signaling across multiple immune cell types. One intriguing possibility is that indole might be capable of discriminating between pro-inflammatory (i.e., IL-6) and anti-inflammatory (i.e., IL-10)-mediated Stat3 activation.

Akt

Figure 7:
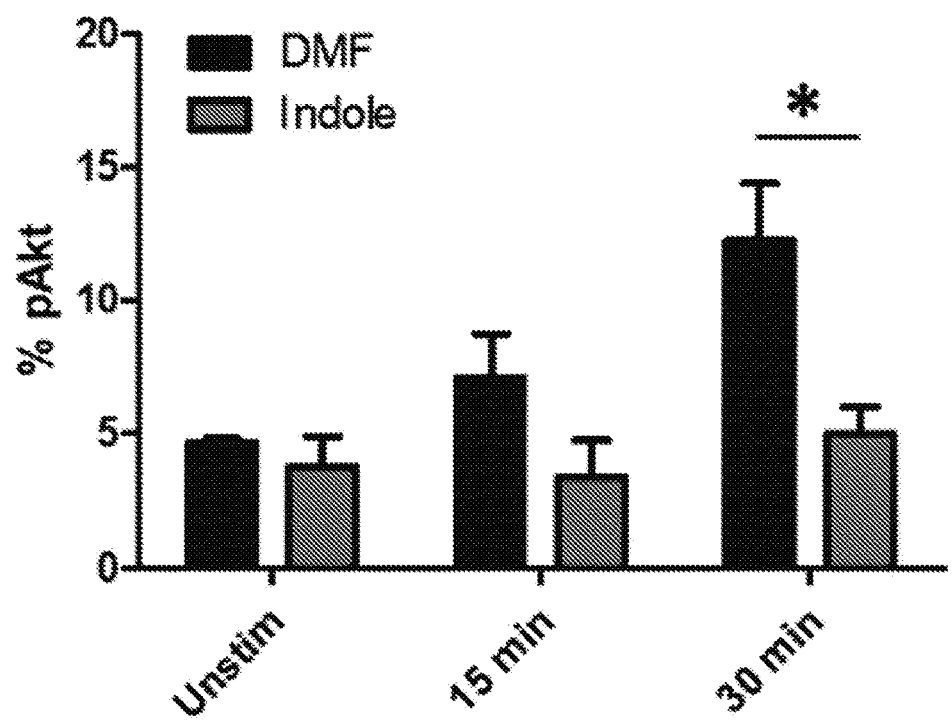
FIG. 7 graphically illustrates that indole inhibits pAkt signaling in BMDCs. Flow cytometric analysis was performed on BMDCs conditioned with indole from day 3 of culture and subsequently stimulated with LPS (5 ug/ml) for the given times. Cells were stained for phospho-Akt and analyzed by flow cytometry. The mean percentage of phospho-Akt-positive DCs from three independent experiments is shown. *$p<0.05$ by Student's t test comparing indole-treated DCs to solvent control (DMF) at indicated timepoints.

Another central mediator of cellular signaling is the serine/threonine kinase, Akt (also referred to as protein kinase B), which regulates cellular processes including metabolism, growth, proliferation, and survival. The Akt pathway is activated by numerous receptor tyrosine kinases, cytokine receptors, G-protein-coupled receptors, and other molecules which activate the lipid kinase PI3K and result in production of phosphatidylinositol (3,4,5)-trisphosphate (PIP5). This second messenger acts as a docking site at the plasma membrane for Akt where phosphorylation and activation occurs. Akt is located upstream of NF-kB and can induce NF-kB signaling via phosphorylation of IKKα and Tp12. The effect of indole on Akt phosphorylation was assessed to determine whether indole's inhibition of NF-kB might be a secondary effect due to modulation of an upstream target. The investigation revealed that treatment with 1 mM indole inhibited LPS-induced Akt phosphorylation in DCs (FIG. 7). This difference was observed at 30 minutes post-LPS stimulation, where phospho-Akt was reduced by over 50% with indole pre-treatment. No difference was observed between indole-DCs and controls in the absence of external stimulation, which indicates that basal Akt signaling is unaffected by indole. Instead, an inflammatory insult appears necessary for indole to dampen Akt phosphorylation. This is important as Akt is ubiquitously expressed in DCs and mediates many essential cellular processes, so a complete ablation of Akt signaling would be detrimental. Whether downstream inhibition of NF-kB is a direct result of indole's effects on Akt or mediated through a distinct pathway remains to be determined. Either way, a robust inhibitory effect of indole on multiple pro-inflammatory signaling pathways in DCs has been revealed.

Anti-Inflammatory Cytokines

Figure 8:
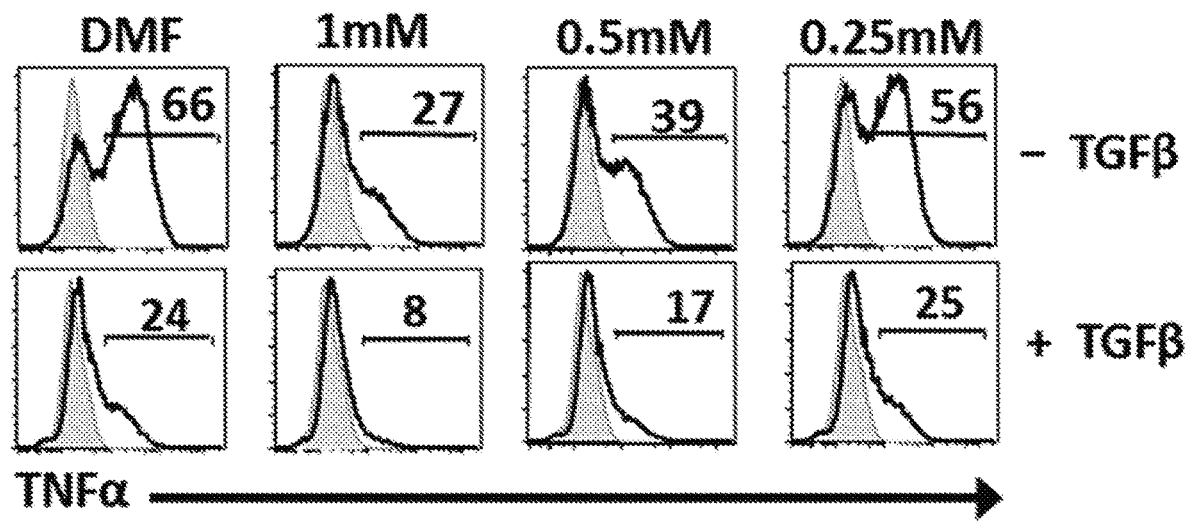
FIG. 8 illustrates that indole synergizes with TGF-β to inhibit TNF production in DCs. Flow cytometric analysis was performed on DC2.4 cells treated with indole or DMF control for 24 hours in the presence or absence of TGF-β (10 ng/ml). DCs were then stimulated with LPS (1 ug/ml) for 4 hours in the presence of Golgiplug protein transport inhibitor and stained for intracellular TNF. Shaded gray areas represent unstimulated samples. Representative histograms from one of three independent experiments.

Based on the close proximity of mucosal DCs to indole in the lower GI tract, the ability of indole to affect specific mucosal DC properties was addressed. A well-known regulator of immune function abundantly present in the GI tract is TGF-β. This cytokine possesses potent anti-inflammatory properties, evidenced by TGF-β-null mice undergoing severe inflammation, autoimmunity, and premature death within 2 weeks of birth. When added to this research platform, a marked synergistic effect of concurrent indole and TGF-β treatment was observed in DCs (FIG. 8). This finding is striking as it demonstrates synergistic effect of two highly-abundant intestinal metabolites, one host-derived and one microbiota-derived.

To determine whether this was a specific downregulation of pro-inflammatory cytokines, production of the canonical DC-produced anti-inflammatory cytokines, IL-10 and TGF-β, was also examined. Neither IL-10 nor TGF-β production were affected by indole conditioning (not shown). Overall these results indicate that indole selectively suppresses pro-inflammatory cytokines and signaling in DCs, resulting in a net anti-inflammatory effect.

Aryl Hydrocarbon Receptor (AhR)

As described above, novel relationships have been revealed that involve the direct effect of indole on DC signaling and cytokine production. In view of the inventors' identification of indole as an AhR ligand, the observed effects of indole on DCs might be mediated through this pathway. Consistent with hypothesis, others have reported that activation of the AhR pathway by treatment with the canonical AhR ligand TCDD lessened pro-inflammatory signs of colitis in a murine DSS model.

Figure 9:
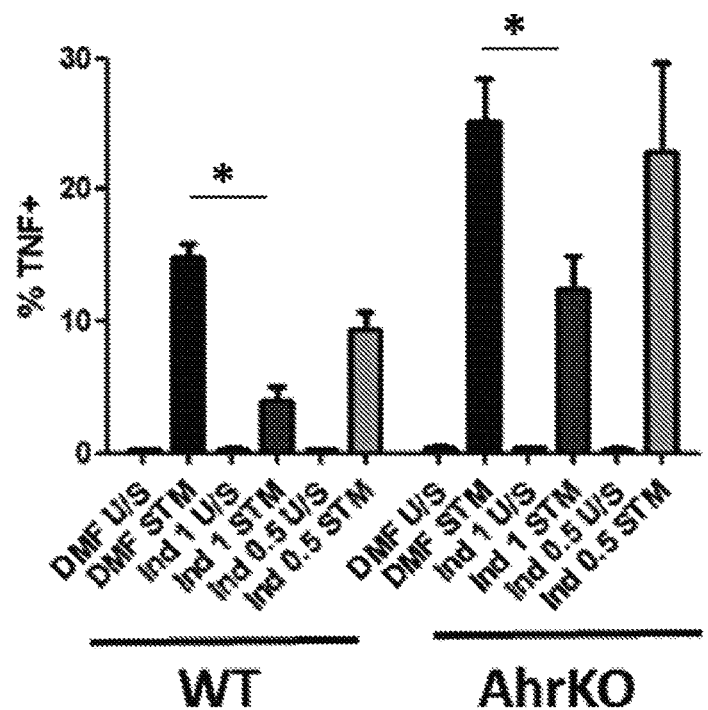
FIG. 9 graphically illustrates that the indole-mediated inhibition of TNF production in DCs is AhR-independent. Splenocytes from WT or AhrKO mice were treated with indole or DMF overnight, followed by stimulation for 6 hours with HK-STM ($4\times10^7$ CFU) in the presence of Golgiplug protein transport inhibitor. Cells were surface stained for CD11c to distinguish DCs followed by intracellular staining for TNF production. Flow cytometric analysis was confined to CD11c+ cells. *$p<0.05$ by Student's t test comparing indole-treated DCs to solvent control (DMF).
Figure 10A:
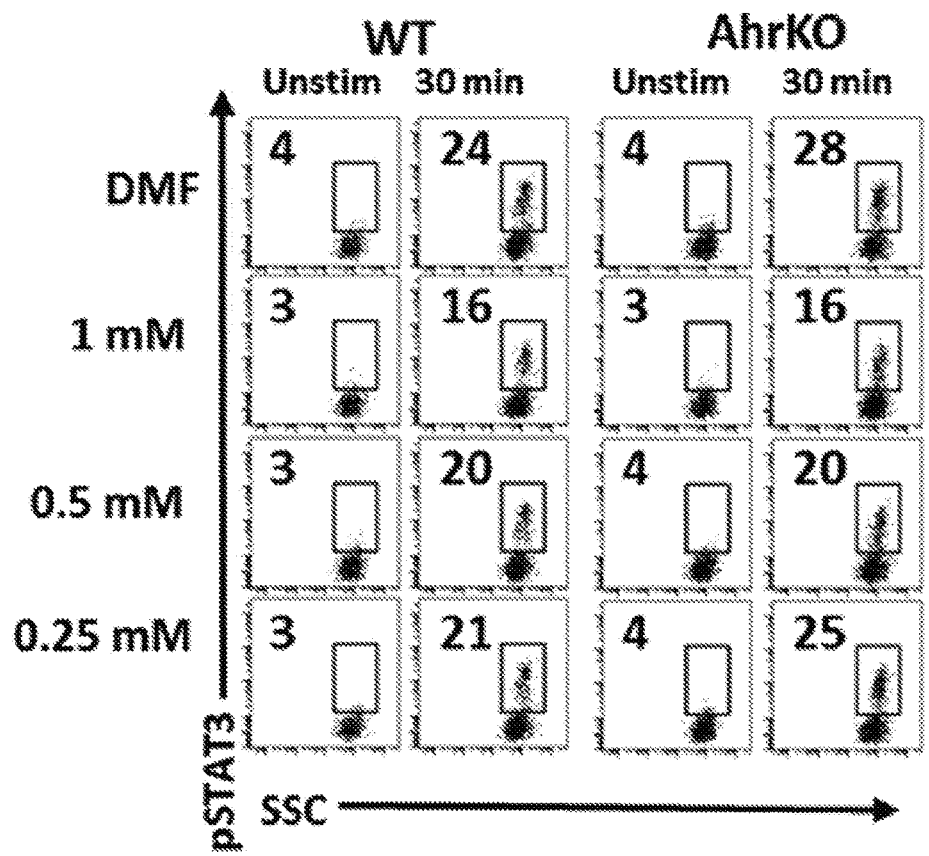
FIGS. 10A-10C graphically illustrate that the indole-mediated inhibition of pStat3 signaling in DCs is AhR-independent. Flow cytometric analysis of BMDCs from WT or AhrKO mice cultured in the presence of indole or DMF from day 3. DCs were stimulated with IL-6 (10 ng/ml) for the given times and stained for phospho-Stat3, which was detected by flow cytometry. Stat3 signaling is shown as percent of phosphorylated cells (FIG. 10A), and MFI of the Stat3 positive population (FIGS. 10B and 10C). The specific Stat3 inhibitor, cucurbitacin I, was included as a negative control. Representative data is shown from one of four independent experiments.
Figure 10B:
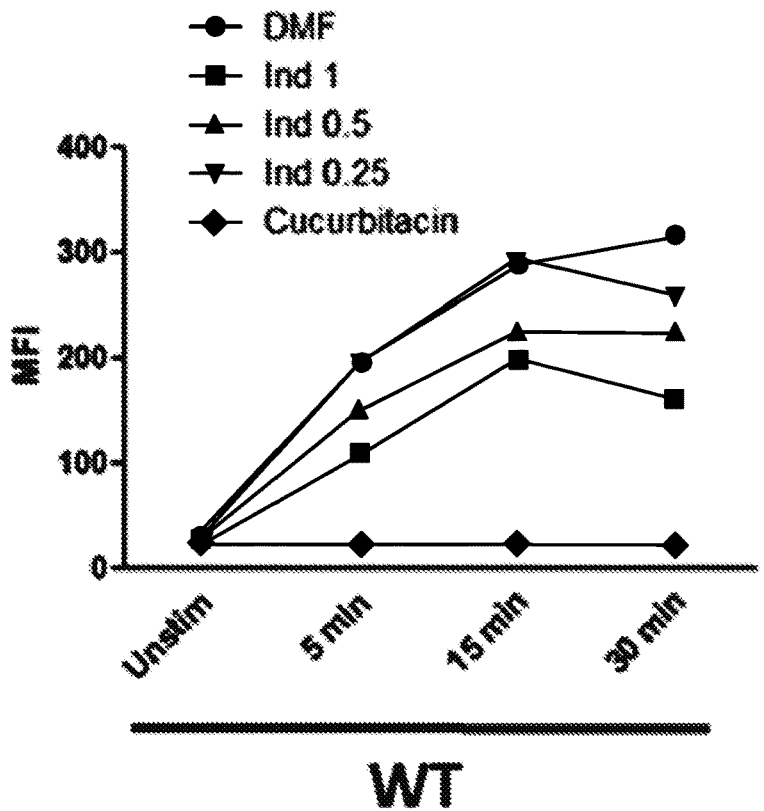
Figure 10C:
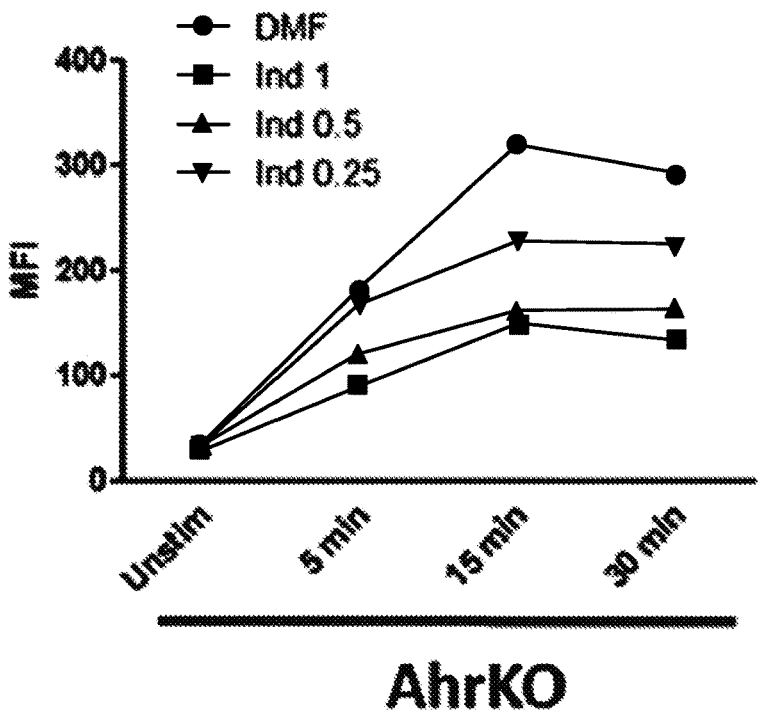
Figure 11:
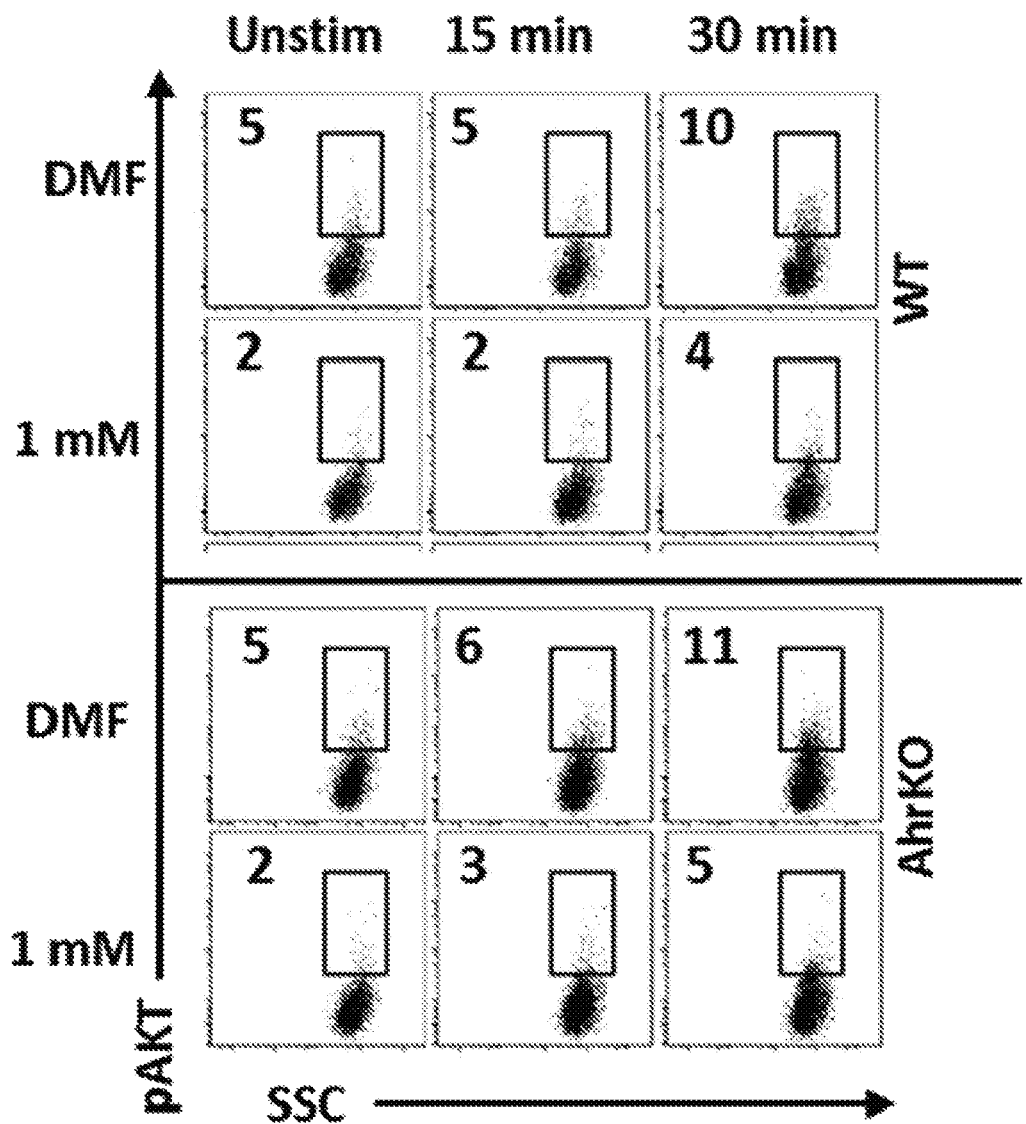
FIG. 11 illustrates that the indole-mediated inhibition of pAkt signaling in DCs is AhR-independent. Flow cytometric analysis was performed on BMDCs from WT or AhrKO mice cultured in the presence of indole (1 mM) from day 3. DCs were stimulated with LPS (5 ug/ml) for the given times and stained for phospho-Akt, which was detected by flow cytometry. Percentage of pAkt-positive DCs indicated. Representative data is from one of three independent experiments.

To evaluate the possible role of AhR in mediating the anti-inflammatory effects of indole on DCs, AhR-deficient mice were acquired and analyzed splenic and bone marrow-derived DCs. Splenocytes from AhR-deficient and WT mice were first treated overnight with indole, followed by stimulation with heat-killed *S. typhimurium*. Consistent with earlier reports, an overall increase in TNF production (~40%) by TLR-stimulated APCs from AhR-deficient mice was observed. Nonetheless, a 2-fold inhibition of TNF production was observed in indole-treated DCs derived from both WT and AhR−/− mice, indicating that the effect was independent of AhR (FIG. 9). Similarly, nearly equivalent inhibition of phospho-signaling was observed in indole-DCs generated from WT or AhR−/− bone marrow in both our Stat3 (FIGS. 10A-10C) and Akt (FIG. 11) experiments. Collectively, these experiments establish that indole's inhibition of pro-inflammatory signaling in DCs is entirely independent of AhR.

Indole does not Alter Antigen-Presenting Cell Properties of Dendritic Cells

To ensure that the observations were not due to indole-induced alteration of the inherent functional capacity of DCs, a series of assays were performed addressing the general functions of DCs. DCs were first treated with indole and assessed for viability by measuring lactate dehydrogenase release as well as propidium iodide uptake. Results from both assays indicated a low level of cellular death, which did not differ from solvent controls, confirming that indole did not induce cytotoxicity in DCs (not shown). The ability of antigen-presenting cells to respond to bacterial LPS is dependent upon the expression of TLR4 on their surface. TLR4 expression levels were compared in DC2.4 and BMDC treated for 18 hours with indole as well as BMDC cultured with indole from day 3. It was observed that indole does not alter surface TLR4 expression on DCs (not shown). In the periphery, DCs exist in an immature state with a high phagocytic capacity. Upon encountering and engulfing antigen, DCs upregulate their expression of maturation markers including MHC-II and the co-stimulatory molecule, CD86. This stimulation triggers the migration of DCs to local lymphoid organs and prepares them for presentation of peptide fragments to naïve T cells. BMDC were treated with indole from day 0, 3, or 6 in culture prior to LPS stimulation. Flow cytometric analysis of MHC-II and CD86 expression revealed that the presence of indole did not alter DC maturation compared to solvent controls (not shown).

Production of reactive oxygen species (ROS) by DCs is an established component of DC-T cell interactions. The secretion of reactive oxygen species (ROS) and nitric oxide (NO) was investigated in DC2.4 and BMDC. The results confirmed that these properties of DCs were also intact regardless of indole treatment (not shown). The phagocytic ability of DCs was examined by incubating DCs with FITC-labeled OVA particles, then analyzing via flow cytometry. Indole did not alter particle uptake by DCs (not shown). Together, these results indicate that indole does not interfere with general APC functions of DCs but is instead selectively dampening inflammation through some alternative mechanism.

Indole Induces Homing Markers on Dendritic Cells

Figure 12A:
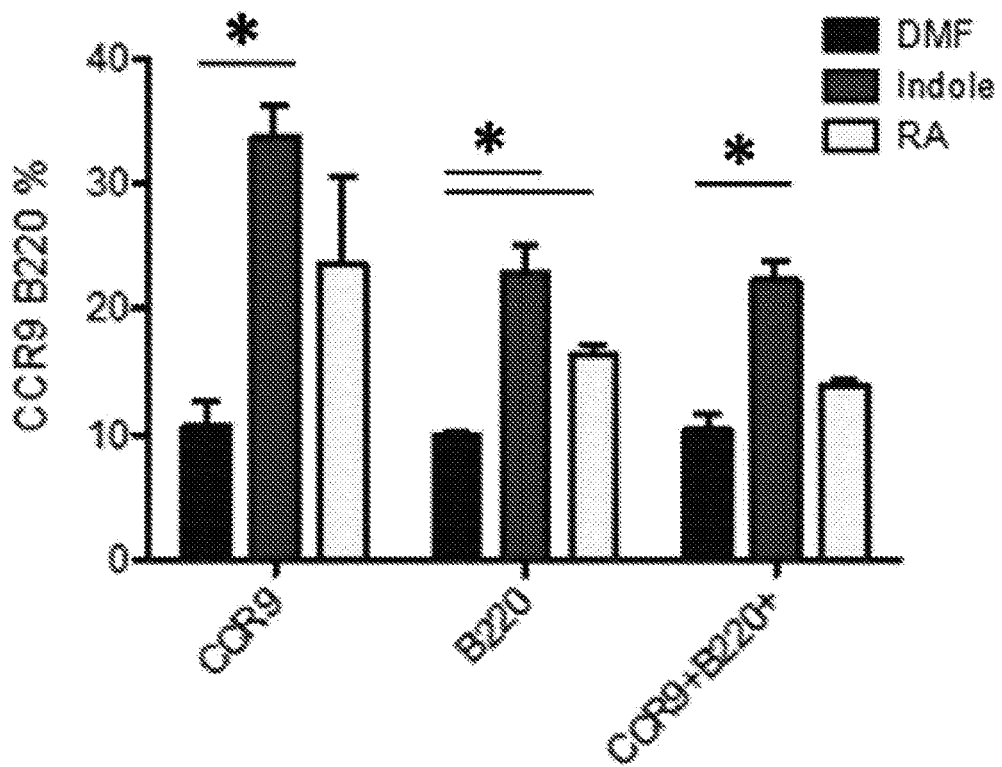
FIGS. 12A and 12B graphically illustrate that indole induces CCR9 and B220 on DCs. BMDCs were cultured in the presence of indole (1 mM), retinoic acid (1 µM), or DMF solvent control from day 3. On day 7, DCs were surface stained for expression of CCR9 and B220 and analyzed by flow cytometry.
Figure 12B:
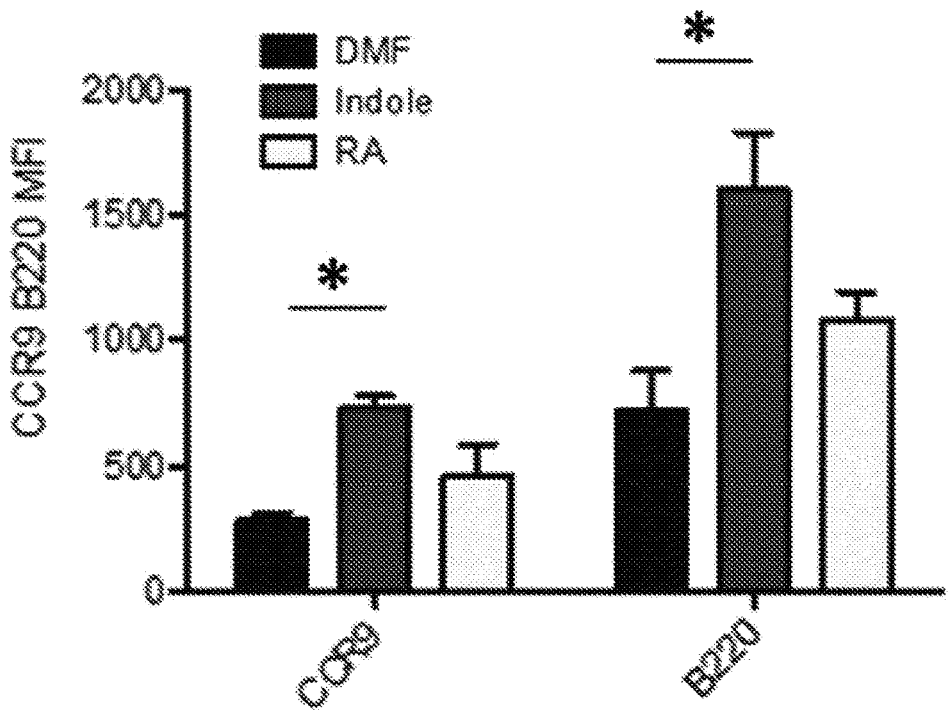

Dendritic cell subsets bear numerous surface antigens that regulate their migration and localization. Because indole is produced in the gut and appears to induce anti-inflammatory properties in DCs (as described above), it was hypothesized that indole might affect migration and retention in mucosal tissues. Thus, expression of the gut homing marker, chemokine receptor CCR9 was investigated. Remarkably, it was observed that indole strongly induced CCR9 on BMDC, indicating that indole imprints DCs with gut-homing specificity (FIGS. 12A and 12B). Retinoic acid (RA) was included as a positive control. RA is present in murine plasma at approximately 1 uM and is predicted to exist at higher concentrations in tissue microenvironments in vivo. Thus, 1 uM was used as a conservative estimate of relevant physiological concentration. Indole's effect was even more profound than that of retinoic acid, a known inducer of mucosal homing markers on T cells (see, e.g., Iwata M, et al. (2004) Retinoic Acid Imprints Gut-Homing Specificity on T Cells. *Immunity* 21(4):527-538). Surface expression of CCR9 on indole-conditioned DCs reached 34%, compared to 22% on RA-conditioned DCs and 10% on solvent controls. Upregulation of this gut homing marker suggests that. in addition to suppressing pro-inflammatory signaling, indole imparts gut homing signals upon DCs to preferentially maintain them within the intestinal environment.

One possible explanation for these observations is that indole promotes retinoic acid availability to the DCs, thus inducing gut homing markers indirectly by providing substrate for a previously identified mechanism. To investigate this possibility, aldehyde dehydrogenase (ALDH) activity was analyzed via flow cytometry using the fluorescent ALDH substrate, Aldefluor. Surprisingly, it was found that indole does not affect ALDH activity in DCs (FIG. 13A). This observation was confirmed by assessing gene expression of aldehyde dehydrogenase family 1 subfamily A2, a rate-limiting enzyme for retinal metabolism in DCs (FIG. 13B). Thus, indole utilizes a novel mechanism for inducing gut-homing markers on DCs, apparently independent of retinoic acid availability.

An indole-induced upregulation of the B220 (CD45R) antigen was also observed (FIGS. 12A and 12B), which is widely used to distinguish the plasmacytoid DC lineage and is believed to contribute to gut homing. However, more recently B220 has been reported to distinguish a DC subset more closely developmentally related to conventional rather than plasmacytoid DCs and a precursor to resident CD8+ and CD8− conventional DCs. This upregulation denotes a differential conditioning effect between RA and indole, as RA does not induce B220 on BMDCs.

Figure 14:
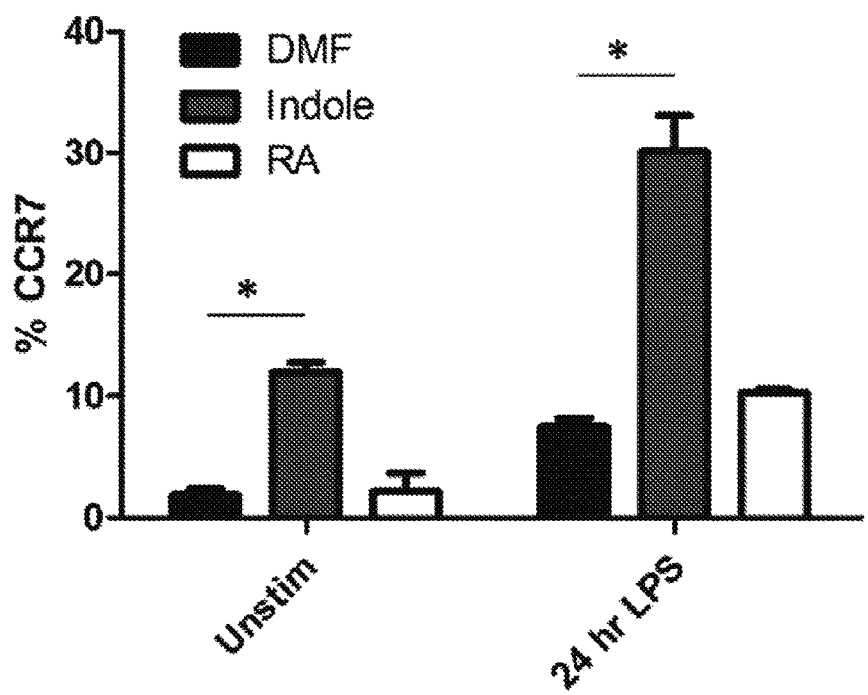
FIG. 14 graphically illustrates that indole upregulates CCR7 expression in DCs. Flow cytometric analysis were performed on BMDCs cultured from day 3 in the presence of indole (1 mM), RA (1 uM), or DMF control and either surface stained for CCR7 expression directly or treated with LPS (1 ug/ml) for 24 hours prior to CCR7 staining. The mean of three independent experiments is shown. * indicates $p<0.05$ for one-way ANOVA followed by Dunnett's post-test.

Encountering maturation-inducing stimuli induces an upregulation of the chemokine receptor CCR7 in DCs. This shift promotes DC migration from peripheral tissues to the lymph nodes to present captured antigen. CCR7 expression facilitates this migration by rendering DCs sensitive to the chemoattractants, CCL19 and CCL21, which direct DCs to T cell areas of lymphoid tissues. Indole conditioning during BMDC development was observed to result in a pronounced increase in expression of CCR7 in day 7 freshly harvested DCs, approximately 5-fold greater than RA or solvent controls (FIG. 14). Exposure to LPS is a DC-activating signal known to upregulate CCR7 expression in order to prime DCs for lymph node entry. Consistent with the literature, exposure to LPS for 24 hours further induced CCR7 expression in our BMDC cultures overall. Here, indole-conditioned DCs once again expressed a higher level of CCR7 expression compared to controls by over 3-fold in magnitude (FIG. 14). This enhancement in CCR7 expression shows a superior capacity for lymph node homing and entry by indole-conditioned DCs.

Discussion

In this section, a novel and previously unappreciated modulation of DC phenotype and function by a single endogenous microbiota metabolite is revealed. Previous investigations by the inventors and others have focused on the immune modulatory effects of indole on intestinal epithelial cells and naïve T cells. However, in this study, dendritic cells, which play a critical role in mediating peripheral tolerance in the lower GI tract, are now interrogated. Surprisingly, conditioning with indole appears to suppress subsequent pro-inflammatory responses by DCs in response to TLR stimuli. Indole-mediated inhibition of the additional pro-inflammatory pathways, Stat3 and Akt, was also observed.

The finding that the effects of indole on DCs are AhR-independent was unexpected as evidence from the interaction of AhR with host-derived endogenous tryptophan metabolites supports a regulatory role for AhR ligands in DCs. The presence of AhR is required for induction of the host-derived enzyme, indoleamine-2,3-dioxygenase (IDO). This enzyme catalyzes the degradation of tryptophan into kynurenine along with other metabolites. Kynurenine is an endogenous AhR ligand and its addition to DC-T cell co-cultures results in enhanced Treg induction and corresponding inhibition of Th17 differentiation. Early exposure of immature DCs to environmental signals determines whether they will express IDO, and IDO– DCs are characterized by immunogenicity whereas IDO+ DCs appear regulatory in nature. These IDO+ DCs produce high levels of TGF-β and IL-10, both of which are immunosuppressive and associated with Treg induction. Thus, AhR-dependent tryptophan metabolism by the host-enzyme IDO produces kynurenine, an AhR ligand which imparts tolerogenic properties upon DCs. Studies using host-derived tryptophan metabolites contrasted with the present work with a microbiota-derived metabolite, suggesting that AhR activities might be differentially regulated based on origin of the AhR ligand.

In addition, it is likely that the ligation and downstream effects of AhR signaling are highly context dependent. Previously the inventors found indole to exhibit antagonist AhR activity in CaC-2 intestinal cells, while both agonistic and antagonistic AhR effects have been previously reported for indole in yeast and a liver cancer cell line, respectively. Indeed, both agonistic and antagonistic activities have been identified in numerous AhR ligands as well as tissue/cell-specific activities. Indole is a small (MW=117.15), hydrophobic molecule shown to be freely diffusible across membranes (Pinero-Fernandez S, Chimerel C, Keyser U F, & Summers D K (2011) Indole Transport across *Escherichia coli* Membranes. *Journal of Bacteriology* 193(8):1793-1798, incorporated herein by reference in its entirety). Therefore, indole might bind to either extracellular or intracellular receptors.

Due to the largely suppressive nature of the effects of indole on DCs, it is possible that the present observations are a result of a general dampening of DC function. Importantly, evidence is provided here that indole does not modify any general antigen-presenting cell functions in DCs. This is important, as inhibition of DC maturation is a mechanism by which factors including IL-10 and TGF-β promote tolerogenic DCs. In fact, the long held paradigm has been that immature and semi-mature DCs drive T cell anergy and Treg formation, whereas fully matured DCs promote immunogenic responses. Evidence in recent years has demonstrated unequivocally that fully mature, antigen-loaded DCs are capable of possessing tolerogenic properties; thus, factors independent of maturation status are involved in mediating DC tolerance versus immunogenicity. The present findings suggest that indole may be one of these previously unidentified factors. An intriguing finding in the present study is the observation that indole upregulates homing markers on DCs. Indole-conditioned DCs exhibited enhanced CCR7 expression (FIG. 14), which indicates a superior capacity to traffic to and enter the lymph nodes. As CCR7 ligands are secreted in T cell areas of lymph nodes, it is proposed that indole-mediated CCR7 upregulation augments interactions between DCs and naïve T cells in situ.

Similarly, indole conditioning appears to upregulate CCR9 on DCs. Cells expressing CCR9 selectively migrate to its specific ligand, CCL25, produced in the small intestine. The identification of indole as a suppressor of inflammatory signaling coupled with CCR9 induction support the result that indole promotes tolerogenic characteristics in DCs. Outside of the mucosa, tissues are largely sterile and, thus, DCs are highly immunogenic in order to prime a rapid and effective adaptive immune response against invading pathogens. Therefore, it would be logical to confine indole-instructed, tolerogenic DCs to the GI tract where anti-inflammatory properties are essential. This finding is particularly novel as the current notion is that RA is indispensable for CCR9 upregulation in DCs. Here, the inventors have identified that a single microbiota metabolite is similarly capable of this action. It is shown that the molecular mechanism of action is not enhanced metabolism of RA, hence indole modulates DC properties through a novel mechanism that remains to be defined.

II. Indole-Conditioned Dendritic Cells Modulate Naïve T Cell Activation

Overview

As described above, indole is shown to be a novel microbiota signal that imparts direct modulation of dendritic cell phenotype (homing markers) and function (cytokine production). Dendritic cells are classified as professional antigen presenting cells, with their predominant function being naïve T cell activation. Thus, the next focus was investigating whether indole conditioning of DCs could modify their interactions with naïve T cells and ultimately modify T cell lineage skew. To this end, DC-T cell interactions were studied providing the following observations: 1) indole-conditioned DCs preferentially induce Tregs under both monoclonal and polyclonal stimulation in a manner that appears to be AhR-independent and cell contact-dependent; 2) indole-conditioned DCs induce gut homing CCR9 on naïve T cells; and 3) indole-conditioned DCs inhibit Th1, Th2, and Th17 lineage differentiation.

Rationale

The predominant general function of DCs is their activation of naïve T cells. In addition to providing the MHC-peptide complex and co-stimulatory factors, DCs also secrete cytokines that aid in the lineage determination of the naïve T cell. This phenotype of the newly activated T cell determines its functional capacity, thus DCs are largely responsible for immune activation versus tolerance. Intestinal DCs play a crucial role in mediating homeostasis in the gut, allowing for the activation of inflammatory responses against pathogens while promoting local immunological tolerance to prevent aberrant inflammation. A major functional feature of gut mucosal DCs is their propensity to induce anti-inflammatory regulatory T-cells rather than pro-inflammatory effector T-cells (Coombes J L, et al. (2007) A functionally specialized population of mucosal CD103+ DCs induces Foxp3+ regulatory T cells via a TGF-β- and retinoic acid-dependent mechanism. *The Journal of Experimental Medicine* 204(8):1757-1764, incorporated herein by reference in its entirety). Based on the inventors' observations in intestinal epithelial cells and the current observations in DCs, described above, indole appears to suppress pro-inflammatory signals. Thus, the investigators studies whether indole conditions DCs to mimic primary mucosal DCs by promoting regulatory T cells. While few host-derived factors such as retinoic acid and TGF-β have been identified as signals that induce Tregs, other potential signals responsible for conferring mucosal properties to DCs remain to be characterized. Determining whether the microbiota-derived metabolite, indole, can modify DC interactions with T cells in a manner consistent with gut DCs would be a novel finding with enormous therapeutic potential.

Results

Figure 15:
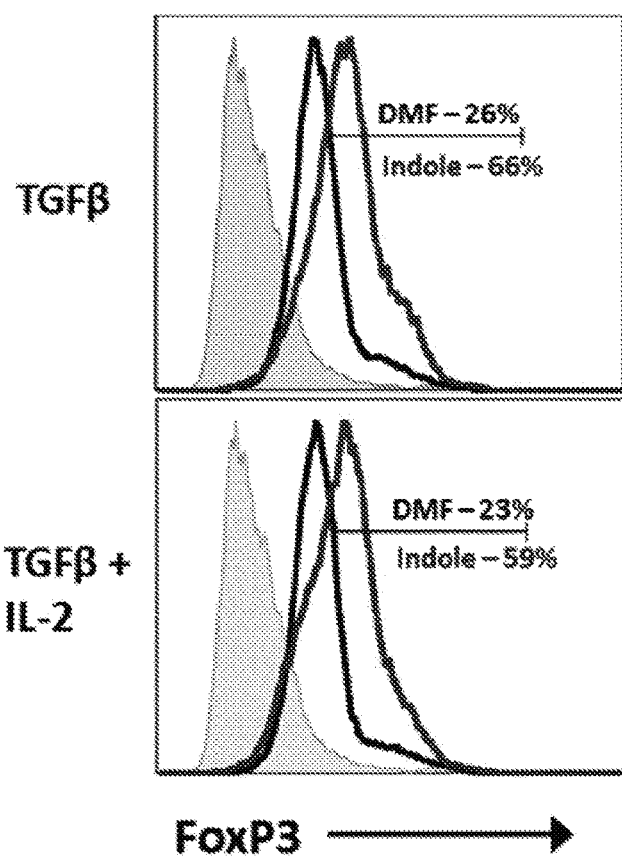
FIG. 15 is a set of FACS plots showing that indole-conditioned DCs preferentially induce Foxp3+ Tregs (polyclonal stimulation). Naïve wild-type CD4+CD25− T cells were sorted and co-cultured with indole- or DMF-conditioned BMDCs. Cells were cultured together for 72 hours in the presence of soluble α-CD3 (5 ug/ml) as well as TGF-β (2 ng/ml) with or without IL-2 (100 U/ml). Subsequently, cells were stained for the transcription factor Foxp3 and analyzed by flow cytometry. Shaded gray histograms represent unstained controls. Representative data from one of four experiments is shown.
Figure 16:
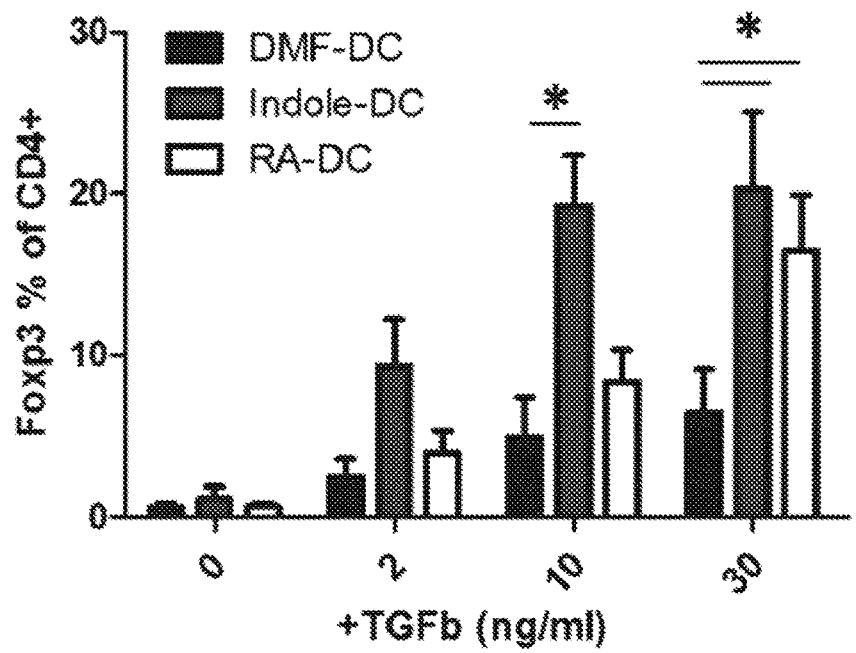
FIG. 16 graphically illustrates that indole-conditioned DCs preferentially induce Foxp3+ Tregs (monoclonal stimulation). Naïve CD4+CD25− T cells from OT-II TCR transgenic mice were isolated and labeled with cell proliferation dye. Naïve T cells were then co-cultured with OVA323-339 peptide-loaded BMDCs for 72 hours in the presence of TGF-β as indicated. BMDCs were previously treated with indole, RA, or DMF from day 3. Following 3 days of co-culture, surface and intracellular staining was performed for flow cytometric analysis. The mean percentage of Foxp3-positive DCs from four independent experiments is shown. * indicates $p<0.05$ for one-way ANOVA followed by Dunnett's post-test.

Indole-Conditioned DCs Preferentially Induce Tregs Under Both Monoclonal and Polyclonal Stimulation To investigate whether indole-conditioned DCs preferentially induce Tregs, a co-culture system using FACS-sorted wild-type naïve CD4+CD25− T cells was employed. These naïve T cells were activated by antibodies against CD3 and CD28 in the presence of indole-conditioned BMDCs and cultured for 72 hours. Under this platform for polyclonal stimulation, a 2-fold increase in Treg induction in indole-DC cultures compared to controls was observed (FIG. 15). Additionally, the inventors pursued the same question in a more physiologically relevant model; i.e., under monoclonal T cell stimulation. To this end, the inventors performed similar experiments using an in vitro antigen-presentation assay with naïve CD4+CD25− T cells from OT-II transgenic mice that express a T cell receptor specific for the peptide sequence 323-339 of chicken ovalbumin (OVA) protein in the context of MHC Class II molecules. Purified naïve CD4+ T cells were co-cultured with OVA323-339 peptide-pulsed BMDCs that were conditioned with indole or retinoic acid from day 3 of development. BMDC preparations were washed extensively to remove any residual conditioning agents. Consistent with other findings described herein, indole-conditioned BMDCs preferentially induced Foxp3+ Tregs, an effect dependent upon exogenous TGF-β being added to the cultures (FIG. 16).

Significant Treg induction by indole-DCs above solvent controls was observed when TGF-β was added at 10 and 30 ng/ml, achieving 3.5-fold greater Treg induction under these conditions. Significance was not reached when exogenous TGF-β was absent or added at a low concentration (2 ng/ml), which leads us to the conclusion that TGF-β is a necessary co-factor for preferential Treg induction by indole-conditioned DCs.

In order to confirm that the differences observed were due to newly activated T cells, the naïve T cells were labeled with cell proliferation dye prior to co-culturing and tracked its dilution. Specifically, naïve CD4+CD25− T cells were labeled with Cell Proliferation Dye prior to DC co-culturing experiments. After 3 days, dilution of dye was assessed by flow cytometry to determine extent of proliferation. A co-culture with DCs lacking OVA peptide (DCs with no peptide) was included as a negative control of T cell activation. Similar proliferation was observed across all co-culture conditions with approximately 60% of the initial T cell population undergoing proliferation (not shown), thus indicating a similar capacity of antigen presentation by DCs in all groups. This result verifies the above conclusion that indole-conditioned DCs enhance Treg induction ex vivo.

Induction of Tregs by Indole-DCs is not Mediated by Soluble Factors

In order to gain insight into the mechanism of indole-mediated Treg skew, it was queried whether these effects were mediated via soluble factors. Naïve CD4+ T cells were polyclonally activated by anti-CD3 in the presence of supernatant from indole-treated BMDC cultures. Specifically, naïve CD4+CD25− T cells were FACS-sorted and plated in 96-well, α-CD3 and α-CD28-coated tissue culture plates in a volume of 100 ul cell culture media. An equal volume of spent DC supernatant from indole, RA, or DMF-conditioned BMDC cultures was added. T cells with DC supernatant were cultured for 72 hours in the presence or absence of exogenous TGF-β. Subsequently, cells were stained for the transcription factor Foxp3 and analyzed by flow cytometry. The BMDC supernatants were generated by growing indole-treated BMDCs for seven days, then washing and culturing for an additional 24 hours to generate indole-free supernatant. Retinoic acid-treated BMDC supernatants were included as a positive control and induced Tregs at approximately 2-fold the magnitude of solvent control DCs. No significant induction of Tregs was observed with indole-DC supernatants beyond solvent controls, suggesting that soluble factors are not responsible for indole-DC Treg skew (not shown).

To validate this observation, an additional culturing method we employed. Transwell tissue culture plates were used to perform co-cultures with a physical barrier between the two cell types. Naïve CD4+CD25− T cells were FACS-sorted and placed in the bottom of a 24-well Transwell cell culture plate with 0.4 uM polycarbonate membranes that had been coated with α-CD3 (5 ug/ml) and α-CD28 (2 ug/ml). TGF-β was added at the indicated concentrations. The insert was placed in the well and indole-, RA-, or DMF-conditioned BMDCs were added to the top chamber such that culture media was shared, but the cell types were kept physically separate. The T cell to DC ratio was 2:1, as in other co-culture experiments. After 3 days, T cells were stained for Foxp3 and analyzed by flow cytometry. Once again, indole-conditioned DCs did not enhance Treg skew despite the addition of exogenous TGF-β, while positive control RA-DCs enhanced Treg induction 3-fold over solvent controls (not shown). These results confirm the supposition that RA-exposed DCs preferentially induce Tregs via soluble factors. In addition, the results confirm that the increased induction of Tregs by indole-DCs is not driven by soluble factors but is instead likely mediated by a cell contact-dependent mechanism.

Indole-Conditioned BMDCs Induce Tregs in the Spleen In Vivo

To address the functionality of indole DC-induced Tregs, an in vivo T cell activation system was employed. The pan T cell surface antigen, Thy1, has congenic alleles, Thy1.1 and Thy1.2, which can be used to differentiate donor and recipient T cells. Naïve CD4+CD25− T cells were purified from OT-II (Thy1.2) mice, then transferred them to recipient Thy1.1 mice. Indole-treated, $OVA_{323-339}$ peptide-loaded BMDCs (Thy1.2) was subsequently transferred to the same recipient Thy1.1 mice. After five days, the recipient mice were sacrificed to assess activation of the transferred naïve T cells, which could only be activated by the transferred, peptide-loaded DCs and are identifiable by the Thy1.2 T cell surface antigen. Cellular populations from the spleen, mesenteric lymph nodes, and pooled distal lymph nodes (axial and inguinal), were examined limiting the analysis to CD4+ T cells bearing the Thy1.2 allele (donor-derived). Importantly, the DCs transferred without OVA peptide loading (negative control) induced virtually undetectable T cell activation. This confirms the specificity of the present model, ensuring that T cell activation in Thy1.2 T cells was solely due to interaction with our experimental BMDCs.

Figure 17A:
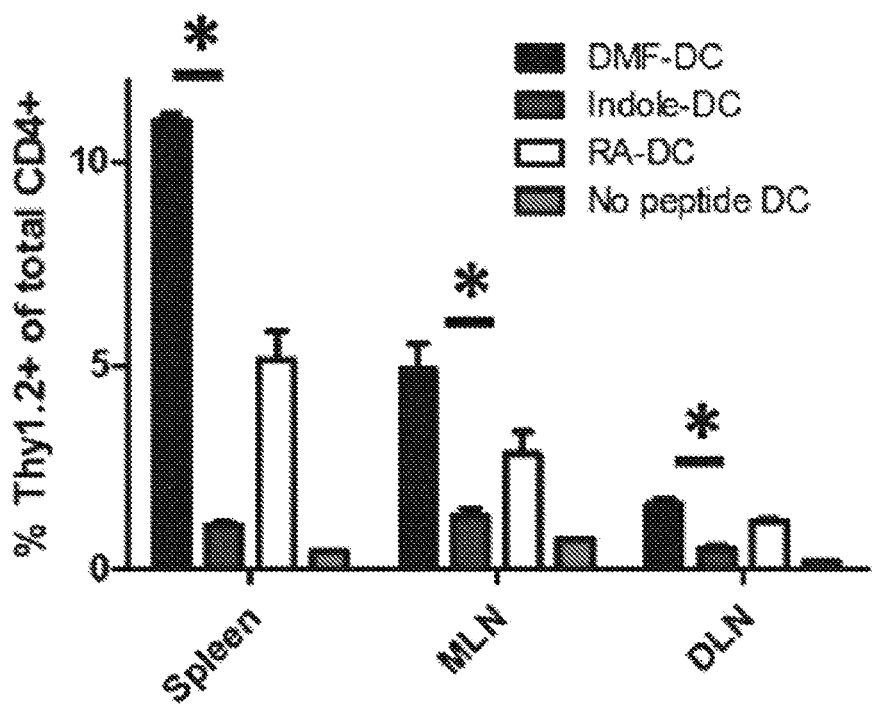
FIGS. 17A-17C graphically illustrate that indole-conditioned DCs induce lower T cell activation overall but a greater proportion of Tregs in spleen compared to control. Naïve CD4+CD25− T cells from OT-II (Thy1.2) mice and OVA323-339-loaded BMDCs conditioned with indole, RA, or DMF were transferred to B6-Thy1.1 mice. After 7 days, tissues were harvested and stained for flow cytometric analysis. Data includes total expansion of Thy1.2+CD4+ T cells (FIG. 17A), percentage of Foxp3+CD4+ T cells of expanded T cells (FIG. 17B), and MFI of Foxp3+CD4+ T cells of expanded T cells (FIG. 17C). n=4 mice/group. One representative experiment of two is shown. *$p<0.05$ by Student's t test.
Figure 17B:
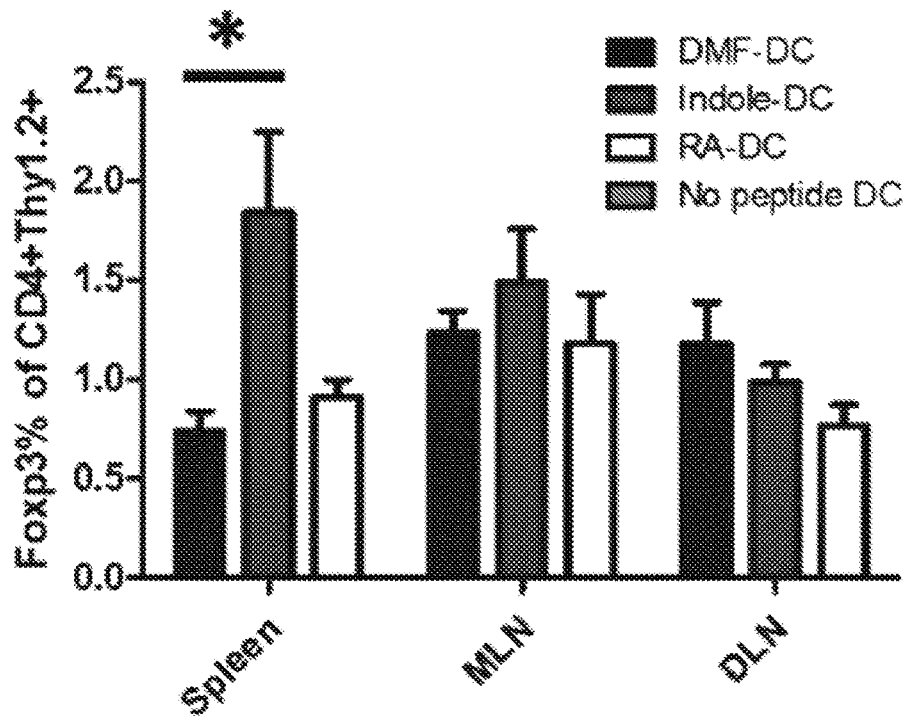
Figure 17C:
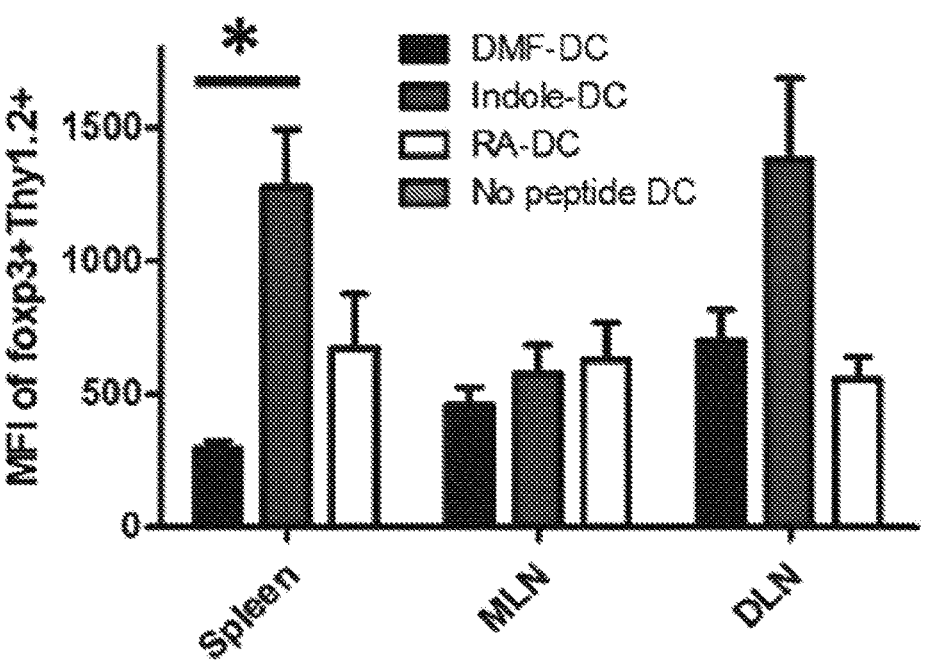

All three tissues demonstrated a substantially lower amount of T cell activation in mice receiving indole-DCs, more than 2-fold less expansion than controls (FIGS. 17A-17C). In fact, T cell expansion induced by indole-DCs was similar to the negative control mice which received DCs lacking OVA peptide. This result was in contrast to our ex vivo co-culture work where the extent of T cell activation was unaffected by indole-DCs, indicating that additional physiological factors might modify T cell activation by indole-DCs in vivo.

Strikingly, of the newly activated T cell population, indole-DCs induced two times more Tregs in the spleen compared to either RA-DCs or DMF-DCs. In addition to a greater proportion of Tregs, these splenic Tregs had a higher mean fluorescence intensity for the Foxp3 transcription factor, indicative of greater Treg stability and suppressive function (126). This enhancement of Treg induction supports the conclusion that indole-conditioned DCs promote tolerance in vivo.

Indole-Conditioned DCs Induce Gut Homing CCR9 on Naïve T Cells

Figure 18:
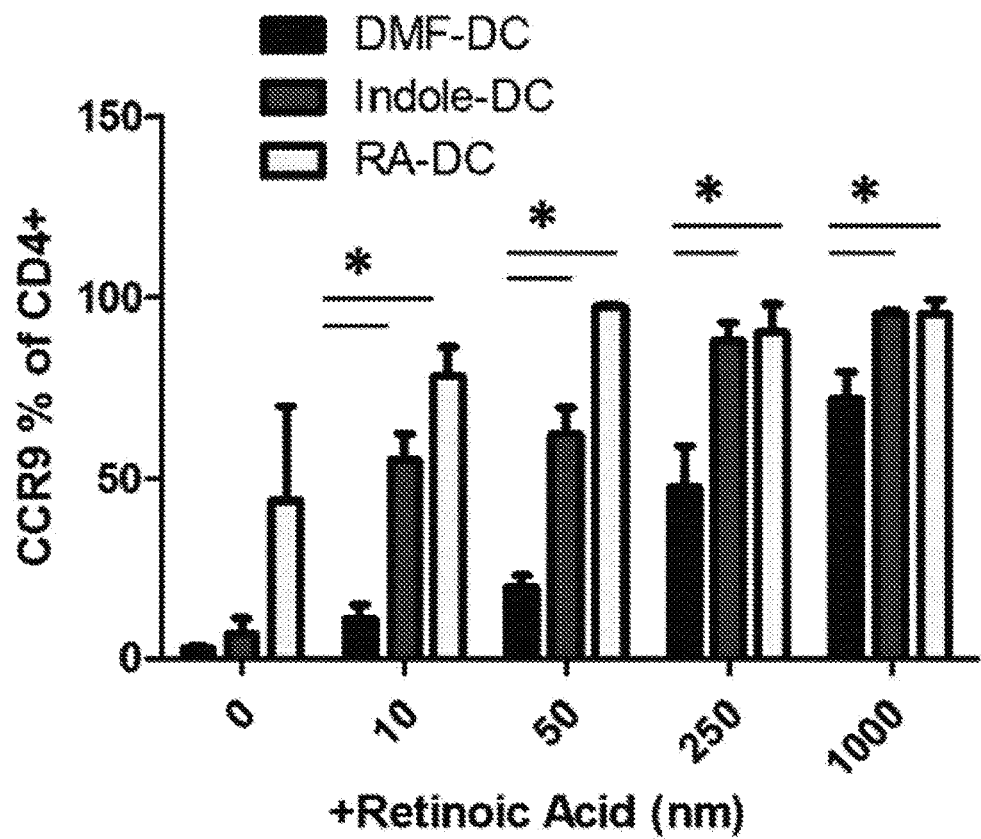
FIG. 18 graphically illustrates that indole-conditioned DCs induce CCR9 on naïve T cells upon activation. Naïve CD4+CD25− T cells from OT-II mice were co-cultured with OVA323-339 peptide-loaded BMDCs for 72 hours in the presence of RA as indicated. BMDCs were previously treated with indole, RA, or DMF from day 3. Following 3 days of co-culture, surface staining was performed for flow cytometric analysis. The mean of three independent experiments is shown. * indicates $p<0.05$ for one-way ANOVA followed by Dunnett's post-test.

Based on the observation that indole induces gut homing markers on developing DCs, it was queried whether indole-conditioned DCs could also confer gut homing markers upon naïve CD4+ T cells. The antigen-specific T cell activation model was used to address this question, and a titration of RA was included as a positive control to induce CCR9. While indole-conditioned BMDCs alone were insufficient to induce CCR9 on naïve T cells, the addition of RA to these cultures resulted in significant CCR9 induction above solvent controls (FIG. 18). Just 10 nM of RA enabled indole-DC co-cultures to achieve over 50% of T cells expressing CCR9 which was similar to RA-DC positive controls, whereas DMF-DC co-cultures with the same concentration of RA added achieved only 10% of CCR9+ T cells. Throughout the titration of RA concentrations ranging 10-1000 nM, indole-DCs consistently induced a similar level of CCR9 expression on T cells compared to RA-DCs and a greater level than was achieved in DMF-DC controls. This data permits the conclusion that RA is an essential co-factor for preferential induction of gut-homing CCR9 on naïve T cells by indole-conditioned DCs. The functional significance of this upregulation has been demonstrated in vivo, with newly activated T cells bearing CCR9 effectively migrating to the small intestine.

Indole-Conditioned DCs Inhibit Th1, Th2, and Th17 Lineage Differentiation

In order to determine whether the indole-conditioned DC induction of Tregs was specific to this lineage, additional T cell fates were quieried. Activated CD4+T helper cells are typically divided into the subsets Th1, Th2, Th17, and Treg, based on their expression of transcription factors and pattern of cytokine secretion. The antigen-specific co-culture system was used to investigate these remaining traditional T cell lineages with the addition of an endpoint PMA/Ionomycin stimulation to induce cytokine secretion. Th17 induction was first examined, as concurrent work by the inventors has suggested that conditioning of naïve T cells directly with indole in the absence of antigen-presenting cells inhibits Th17 differentiation.

Figure 19A:
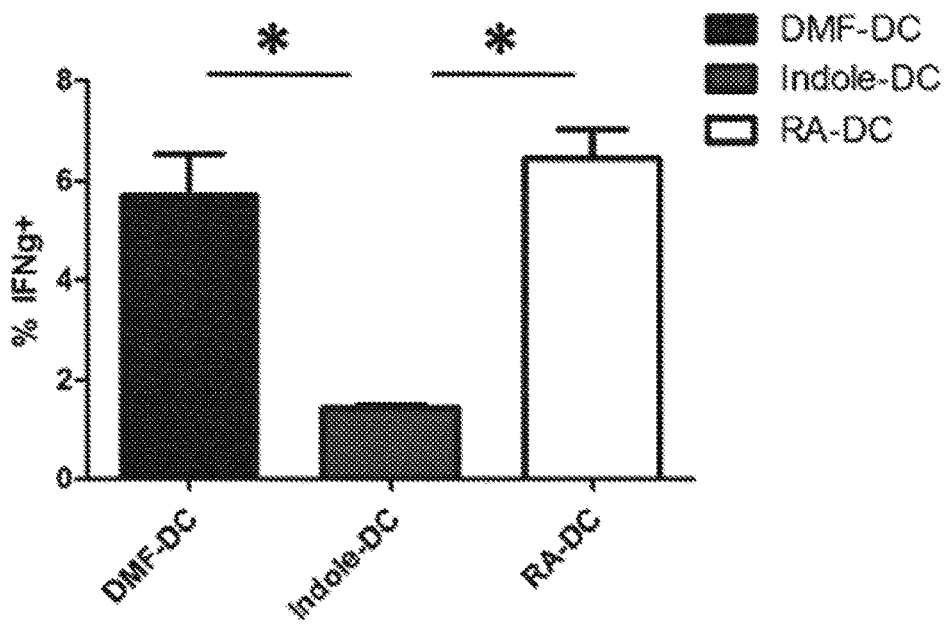
FIGS. 19A-19C graphically illustrate that indole-conditioned DCs inhibit Th1, Th2, and Th17 differentiation. Naïve CD4+CD25-T cells from OT-II TCR transgenic mice were isolated by column purification. Naïve T cells were then co-cultured with OVA323-339 peptide-loaded BMDCs for 72 hours in the presence or absence of lineage-skewing cytokines (described in methods). BMDCs were previously treated with indole, RA, or DMF from day 3. For the last 5 hours of culture, T cells were restimulated with PMA and ionomycin in the presence of Golgiplug, followed by intracellular staining. Cytokine production was determined to assess differentiation of Th1 (FIG. 19A), Th2 (FIG. 19B), and Th17 CD4+T (FIG. 19C) cells. Mean of three independent experiments. * indicates $p<0.05$ for one-way ANOVA followed by Dunnett's post-test.
Figure 19B:
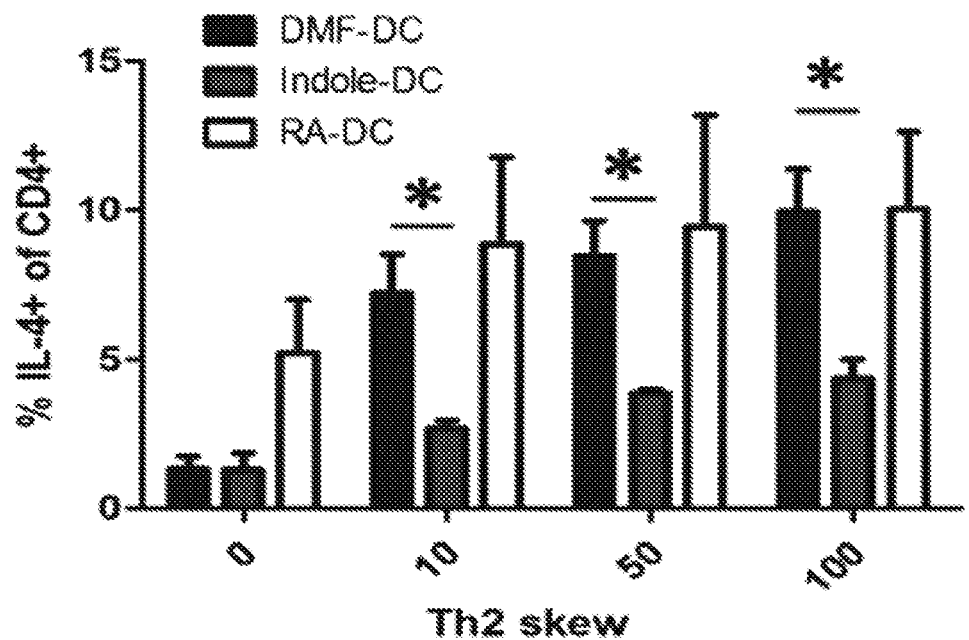
Figure 19C:
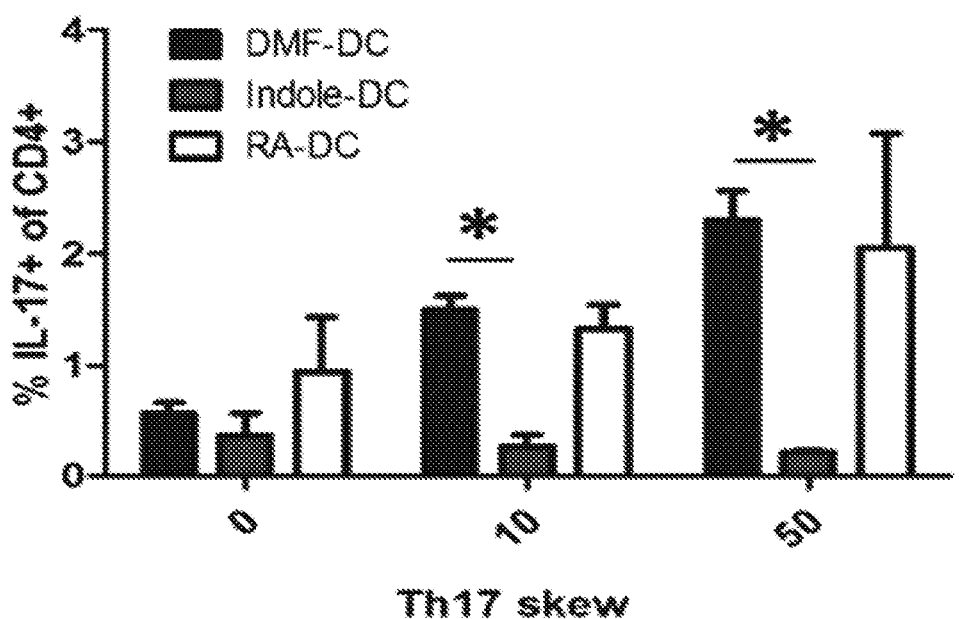

In agreement with these observations, indole-conditioned DCs was also found to inhibit Th17 differentiation, despite the presence of Th17-skewing cytokines added to the culture (FIGS. 19A-19C). The presence of indole-DCs maintained Th17 differentiation at a rate of less than 0.5% of T cells, compared to 2.5% Th17 in DMF-DC control cultures. Importantly, this indicates that indole conditioning of DCs is able to overcome physiological skewing factors which drive Th17 induction. Next, the Th1 and Th2 lineages that largely mediate cell-mediated and humoral immune responses, respectively, were interrogated. Once again, a stark inhibition of the development of these lineages was observed (FIGS. 19A-19C). These findings indicate that indole conditions DCs to preferentially induce regulatory T cells while suppressing the differentiation of other, largely pro-inflammatory, helper T cell lineages.

T Cell Lineage Skewing by Indole-DCs is AhR-Independent

Using a similar co-culture system, others have reported that AhR-deficient BMDCs skew naïve T cell differential away from Tregs. Considering the observation of skewing towards Tregs by indole and the identification of indole as an AhR ligand, as described herein, it was queried whether Treg skew by indole might be mediated via the AhR pathway. Antigen-specific T cell activation was performed using naïve T cells from OT-II mice co-cultured with indole-treated BMDCs derived from wild-type or AhR−/− mice. Consistent with the prior findings, an overall decrease in Treg induction (~30%) when naïve T cells were activated with AhR−/− BMDCs was observed.

Figure 20A:
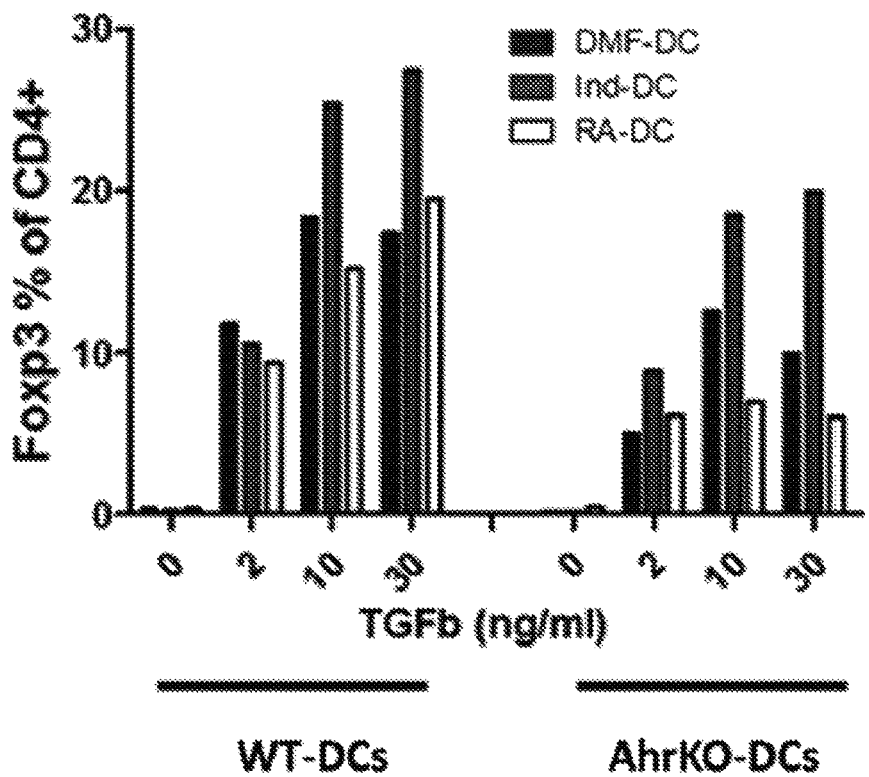
FIGS. 20A and 20B graphically illustrate that T cell skewing mediated by indole-conditioned DCs is AhR-independent. BMDCs were differentiated from WT or AhR-KO mice and conditioned with indole, RA, or DMF from day 3. DCs were then loaded with OVA323-339 and co-cultured with naïve CD4+CD25− T cells from OT-II transgenic mice for 72 hours. For Th1 cultures, T cells were restimulated with PMA and ionomycin in the presence of golgiplug for the last 5 hours of culture. Subsequently, all cultures were stained and analyzed by flow cytometry for Foxp3 to identify Tregs or (B) IFNγ to identify Th1 cells.
Figure 20B:
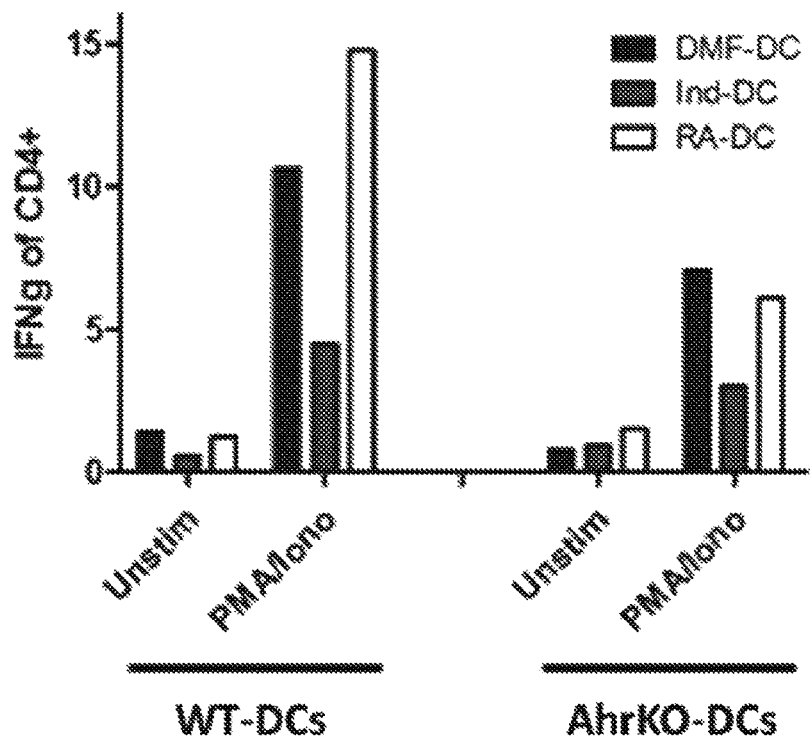

However, similar to the results in Section I (above), it was found that the Treg skewing induced by indole-conditioned BMDCs was entirely independent of AhR (FIGS. 20A and 20B). Similarly, the inhibition of the Th1 lineage by indole-conditioned BMDCs was apparent in co-cultures using DCs derived from both wild-type and AhR-deficient mice, resulting in our conclusion that this effect of indole is also AhR-independent (FIGS. 20A and 20B).

Transfer of Indole-Conditioned DCs Prevents Shortening of the Colon

Figure 21A:
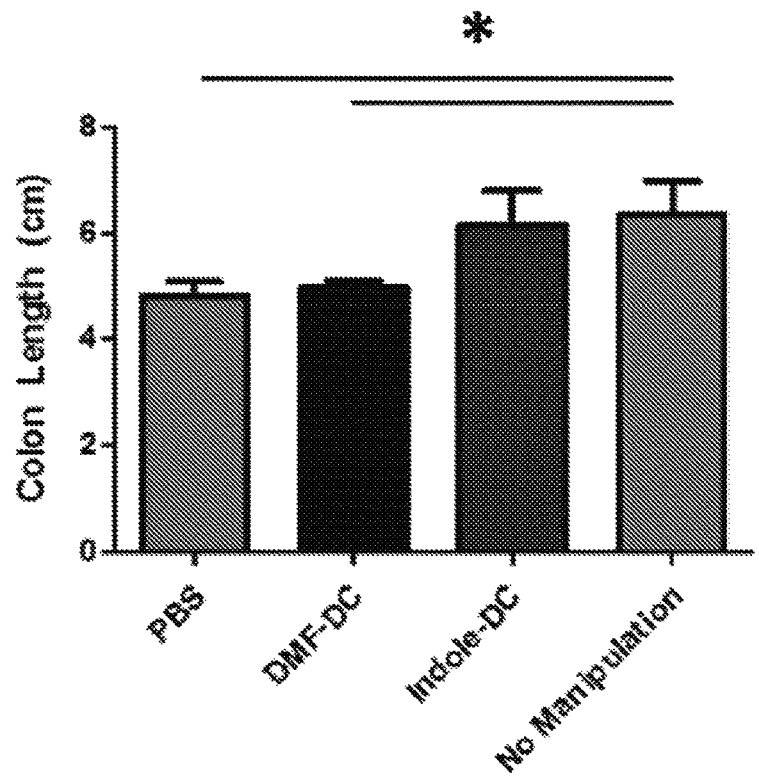
FIGS. 21A and 21B graphically illustrate that the in vivo transfer of indole-conditioned DCs prevented shortening of colon in a murine DSS colitis model. BMDCs were cultured with indole, RA, or DMF from day 3. Two million BMDCs were transferred via i.p. injection to WT C57BL/6 mice on days 0, 6, and 9 of the experiment. Mice received 5% dextran sulfate sodium (DSS) ad libitum in their drinking water from day 7 through day 14. Mice were euthanized on day 20 and colons were immediately removed and measured for length (FIG. 21A) and weight (FIG. 21B). n=4 mice/group. *$p<0.05$ by one-way ANOVA followed by Dunnett's post-test, comparing to unmanipulated control colons.
Figure 21B:
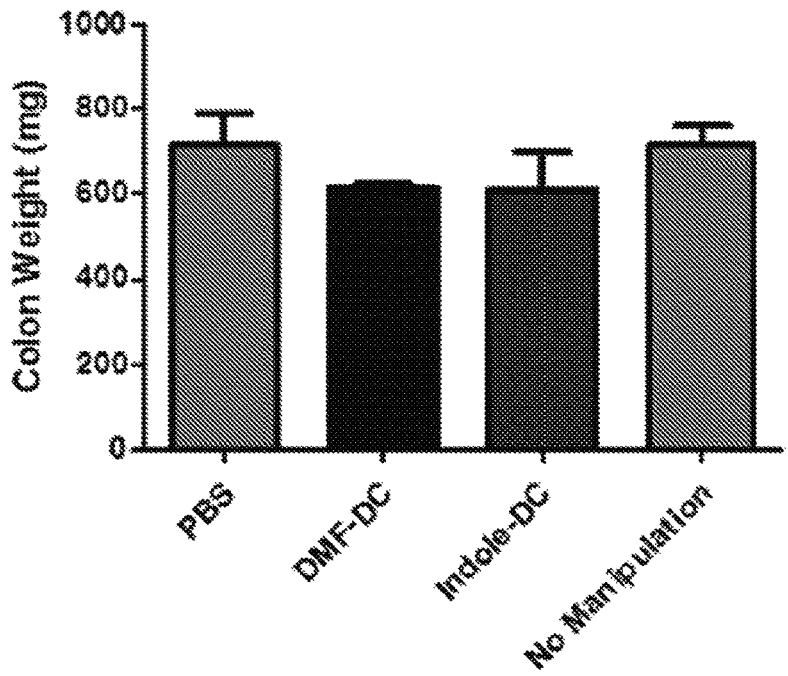

A hallmark pathological sign of colitis is shortening of the colon, mediated by abscesses forming in the intestinal crypts that disrupt the mucosal architecture and are later replaced by scar tissue. An intriguing finding in our study was that the average colon length of indole-DC-transferred mice was similar to unmanipulated control mice (~6 cm), while DMF-DC-transferred and no DC-transferred mice exhibited shorter colons (~4.5 cm) at endpoint analysis (FIGS. 21A and 21B). Shortening of the colon is an established indicator of colitis pathology in the murine model of DSS colitis. Thus, the observation indicates that indole-DCs play a role in mediating recovery from colitis.

Discussion

Figure 22:
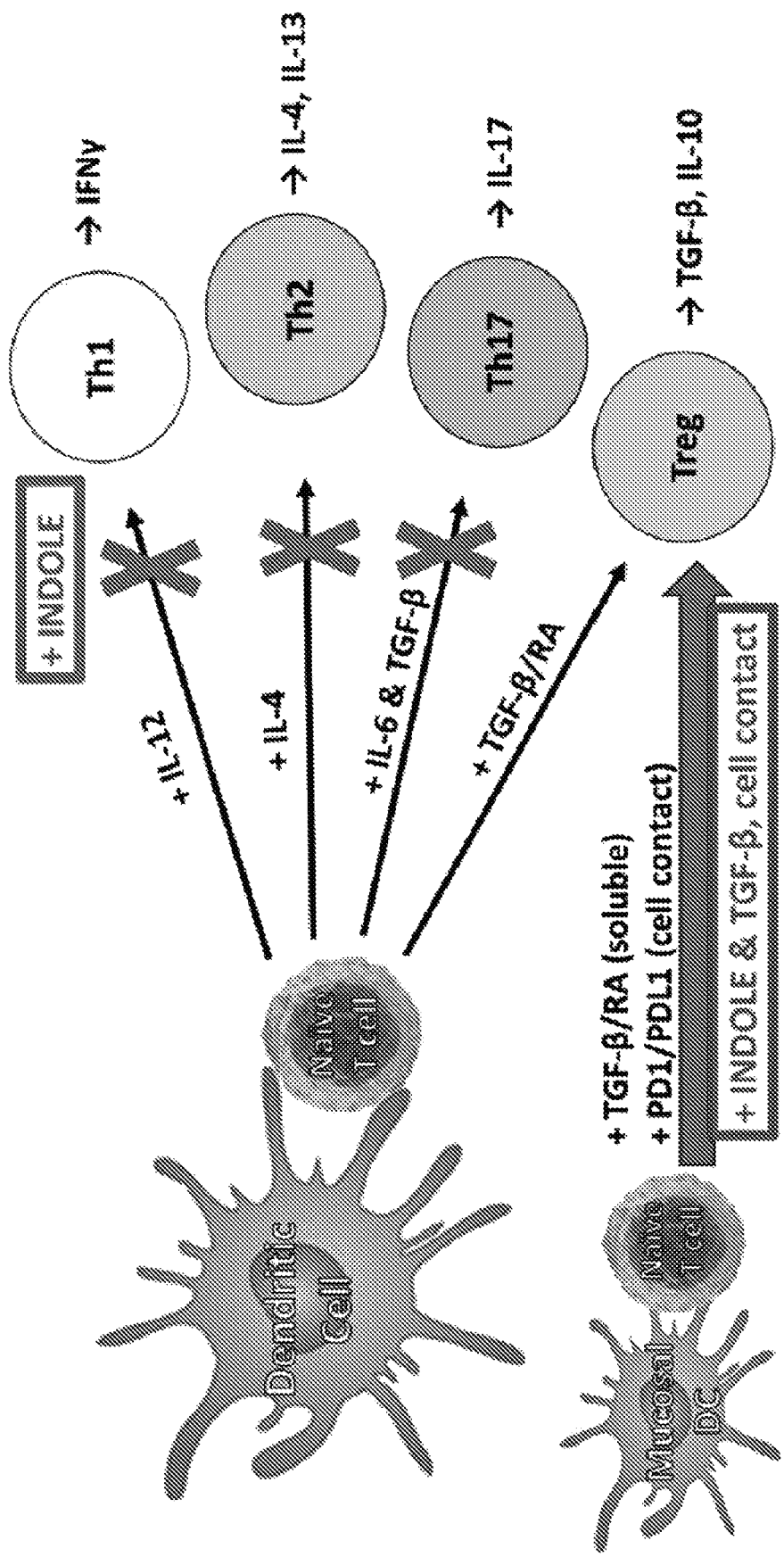
FIG. 22 is a cartoon illustration showing that indole-conditioned DCs preferentially induce Tregs and inhibit Th1, Th2, and Th17 lineages. Antigen-loaded dendritic cells (DC) activate naïve T cells by presenting antigenic peptide and interacting with co-stimulatory molecules, along with a third signal mediated by soluble factors or cell contact. This signal from the DC, such as cytokine production, determines the effector lineage and resulting downstream function of the newly activated T cell. Mucosal DCs preferentially induce regulatory T cells (Treg) by soluble or cell contact-mediated mechanisms. The current study provides evidence that indole-conditioned DCs preferentially induce Tregs in a TGF-β-dependent manner and requires cell contact between the DC and naïve T cell. In addition, indole-treated DCs inhibited differentiation of Th1, Th2, and Th17 cells.

In this Section, previously unappreciated biology is identified in which conditioning of dendritic cells with a single microbiota-derived metabolite is sufficient to modulate its T cell activating functions in a tolerance-promoting manner (FIG. 22). It is demonstrated herein that indole-conditioned DCs preferentially induce Foxp3+ Tregs in a TGF-β-dependent manner, further suggesting a synergistic effect of indole and TGF-β as observed in chapter two. This effect was validated in multiple models of naïve T cell activation—under both polyclonal (anti-CD3) and monoclonal (antigen-specific OT-II) stimulation. The monoclonal stimulation conditions are particularly relevant as this mimics true physiological interaction between a naïve T cell and antigen-presenting cell. Two signals are essential for a naïve CD4+ T cell to become activated by an antigen-presenting cell: First is engagement of the T cell receptor (TCR) by MHC-II on the APC, and second is co-stimulation, typically ligation of T cell CD28 by CD80 or CD86 on the surface of the APC. It is demonstrated in Section I that indole does not modify general DC function, nor expression of the DC surface molecules MHC-II, CD80, or CD86. This evidence demonstrates that conditioning of DCs with indole leaves the TCR-APC complex intact and does not account for observed differences in T cell activation.

The inventors have described the identification of indole as a ligand of the aryl hydrocarbon receptor. In addition, the inventors have shown that the presence of indole during anti-CD3-mediated naïve T cell activation also preferentially induces Foxp3+ Tregs. However, studies comparing naïve T cells derived from wild-type versus AhR−/− mice indicated that this effect was at least partially mediated through the aryl hydrocarbon receptor. Therefore it was somewhat surprising in this study to observe that indole-DC conditioning effects on T cells were entirely AhR-independent, despite having observed AhR-independent effects of indole directly on DCs in chapter two.

Based on these seemingly contradictory observations, it is likely that indole interacts with different immune cell subsets by distinct mechanisms. As discussed in Section I, both agonistic and antagonistic activities have been identified in numerous AhR ligands as well as tissue/cell-specific activities. Further work is warranted to determine the molecular mechanism responsible for indole's specific effects on DCs.

It was demonstrated herein using multiple methods that the observed preferential Treg skew by indole-DCs requires contact between DCs and naïve T cells. This was an unexpected finding, given that the known Treg-skewing elements are soluble factors secreted by host immune and epithelial cells. The host-derived cytokine, TGF-β, is present at high concentrations in the GALT and is produced by gut epithelial cells as well as various immune cell subsets. This cytokine is well appreciated for its crucial role in intestinal homeostasis; TGF-β-deficient mice develop lethal gut and systemic inflammation and murine models of colitis are alleviated by TGF-β treatment. TGF-β is a crucial factor for Foxp3+ Treg induction. In a co-culture system similar to that described herein using naïve T cells and CD103+ DCs isolated from murine MLNs, the addition of a blocking monoclonal antibody against TGF-β completely abrogated Foxp3+ Treg induction. Interestingly, it was reported that the addition of exogenous TGF-β to these co-cultures induced a strong enhancement of Treg conversion in cultures with CD103+ DCs but only a minimal induction with CD103− DCs (Coombes J L, et al. (2007) A functionally specialized population of mucosal CD103+ DCs induces Foxp3+ regulatory T cells via a TGF-β- and retinoic acid-dependent mechanism. *The Journal of Experimental Medicine* 204(8):1757-1764, incorporated herein by reference in its entirety).

Consistent with the literature, the RA-conditioned DCs enhanced Foxp3+ Treg skew when supplemented with exogenous TGF-β. This supports the notion that both TGF-β and retinoic acid are essential components for Treg induction. Indeed, the inclusion of synthetic RA inhibitors (LE540 and LE135) blocked the ability of CD103+ MLN DCs to skew naïve T cells towards Foxp3+ Tregs (Coomber J L, et al. (2007) A functionally specialized population of mucosal CD103+ DCs induces Foxp3+ regulatory T cells via a TGF-β- and retinoic acid-dependent mechanism. *The Journal of Experimental Medicine* 204(8):1757-1764), emphasizing the necessity of RA in this conversion.

In addition to its role as a co-factor in Treg induction, RA also enhances the expression of chemokine receptor CCR9 and the integrin α4β7 on T cells upon activation. Retinoic acid is a product of the catabolism of dietary vitamin A, formed by intracellular oxidative metabolism of retinol. The major physiological form, all-trans-RA, binds predominantly to members of the nuclear retinoic acid receptor family (types α, β, and γ). The inventors found that in vitro conditioning with RA during development was sufficient for BMDCs to induce CCR9 on naïve T cells, whereas indole-conditioned BMDCs and control BMDCs did not induce CCR9. However, the addition of exogenous RA into the indole-DC co-cultures resulted in a pronounced induction of CCR9, similar to the level observed in RA-DC cultures. This finding suggests that indole conditioning does not confer RA-producing capacity to DCs, which is in agreement with the described unexpected finding in Section I that indole inhibits aldh1a2 expression and does not induce aldehyde dehydrogenase activity. Instead, it is proposed that indole affects DCs through an alternative mechanism that remains to be identified.

Based on the present findings, one hypothesis is that indole primes DCs to exhibit heightened sensitivity to the presence of TGF-β and/or retinoic acid, thus explaining the observed synergistic effects.

The in vivo T cell activation experiments disclosed herein affirm the ex vivo findings that indole-conditioned DCs are capable of preferentially inducing Foxp3+ Tregs. This Treg enhancement was observed in the spleens of recipient mice, both in proportion of Tregs and Foxp3+ mean fluorescence intensity. Using the ex vivo co-culture system, exogenous TGF-β was identified as an essential co-factor to direct indole-mediated Treg skew; however the observation of in vivo Treg skew indicates that any required co-factors were present and biologically available.

III. Pro-Inflammatory Signaling is Down-Regulated in Indole-Conditioned Macrophages Overview In addition to dendritic cells, macrophages are the other prominent mononuclear phagocyte residing within the intestinal environment. While the primary role of DCs is activation of naïve T cells, macrophage functions are focus on clearance of bacteria from the tissue and communicating danger signals to other immune cells. To determine whether indole modulates the function of other antigen-presenting cells in addition to DCs, several of the hallmark observations in bone marrow-derived and primary splenic macrophages were tested. The completion of this study has revealed these findings: 1) indole pre-conditioning suppresses pro-inflammatory cytokine production in macrophages; 2) pro inflammatory signaling pathways are inhibited by indole conditioning in macrophages; and 3) the effects of indole on macrophages appear to be AhR-independent.

Rationale

Macrophages are the most prevalent mononuclear phagocytes in the steady-state lamina propria and play a crucial role in tissue homeostasis. The ontogeny of intestinal macrophages is unique from other tissue-resident macrophages in that these cells display a short half-life, under constant renewal from circulating monocytes. These macrophage precursors might encounter high concentrations of indole upon entering the intestinal environment, thus indole might play a role in shaping their inflammatory functions. Others have previously demonstrated that treatment of macrophages with the microbial metabolite, butyrate, can alter their function, primarily the down-regulation of pro-inflammatory mediators. The findings disclosed in Section I revealed that indole conditioning of DCs robustly dampened their subsequent responses to TLR-mediated inflammatory stimuli. Thus, treating macrophages with indole might result in a similar suppression of pro-inflammatory responses.

Rationale

Figure 23A:
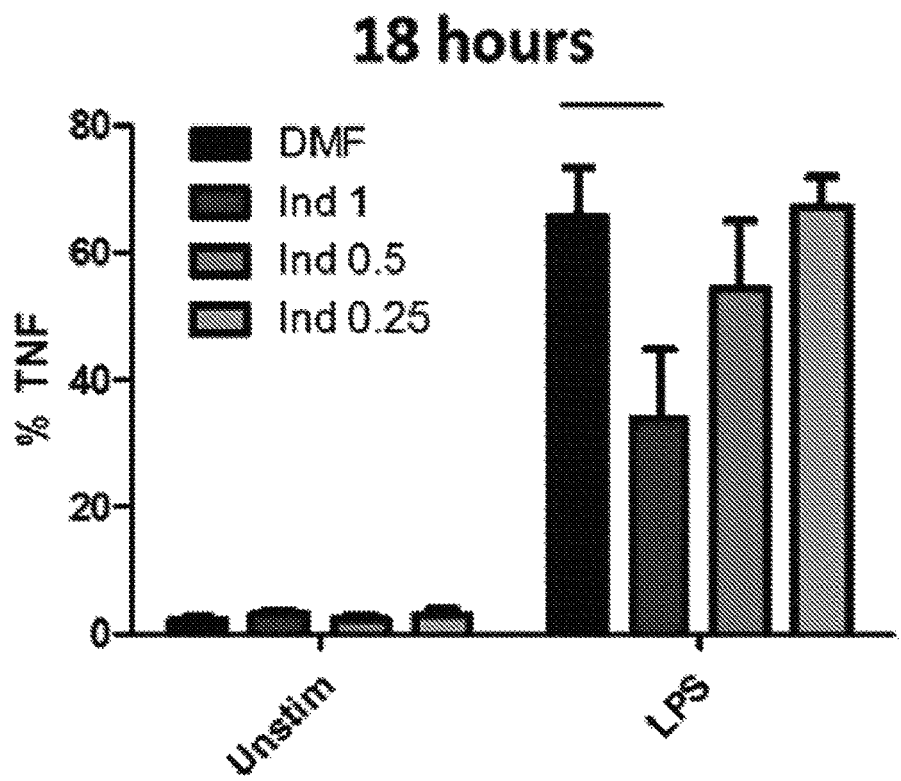
FIGS. 23A and 23B graphically illustrate that treatment for 18 or 4 hours with indole inhibits TNF and IL-12 production in BMDMs. BMDMs were treated with indole or DMF control for 18 hours or 4 hours, followed by stimulation with LPS (2 ug/ml or 250 ng/ml) for 4 hours in the presence of Golgiplug. BMDMs were then stained for intracellular TNF or IL-12 and analyzed by flow cytometry. Aggregate data is shown from 4 experiments with 18 hours indole treatment for TNF production (FIG. 23A) or IL-12 production (FIG. 23B). *$p<0.05$ by Student's t test.

Indole Pre-Conditioning Suppresses Pro-Inflammatory Cytokine Production in Macrophages First, pro-inflammatory cytokine production in macrophages was investigated. Bone marrow-derived macrophages (BMDMs) were cultured to high purity, routinely achieving >96% of cells bearing the hallmark macrophage signature of CD11b and F4/80 expressed on their surface. In the DC study described herein, DCs were typically conditioned with indole during their development from bone marrow precursors in order to mimic the proximity of DC progenitor cells to indole in the intestinal microenvironment during development. However based on the unique nature of intestinal macrophage ontogeny, a shorter treatment with indole would was determined to be more physiologically relevant as these cells are short-lived and continually being replenished from the circulation. BMDMs were treated for 18 hours with indole, followed by a 4 hour stimulation with either a very high (2 ug/ml) or low (250 ng/ml) dose of LPS. Intracellular cytokine staining revealed that production of both TNF and IL-12 were inhibited by nearly 2-fold in macrophages treated with 1 mM indole (FIG. 23A).

Figure 23B:
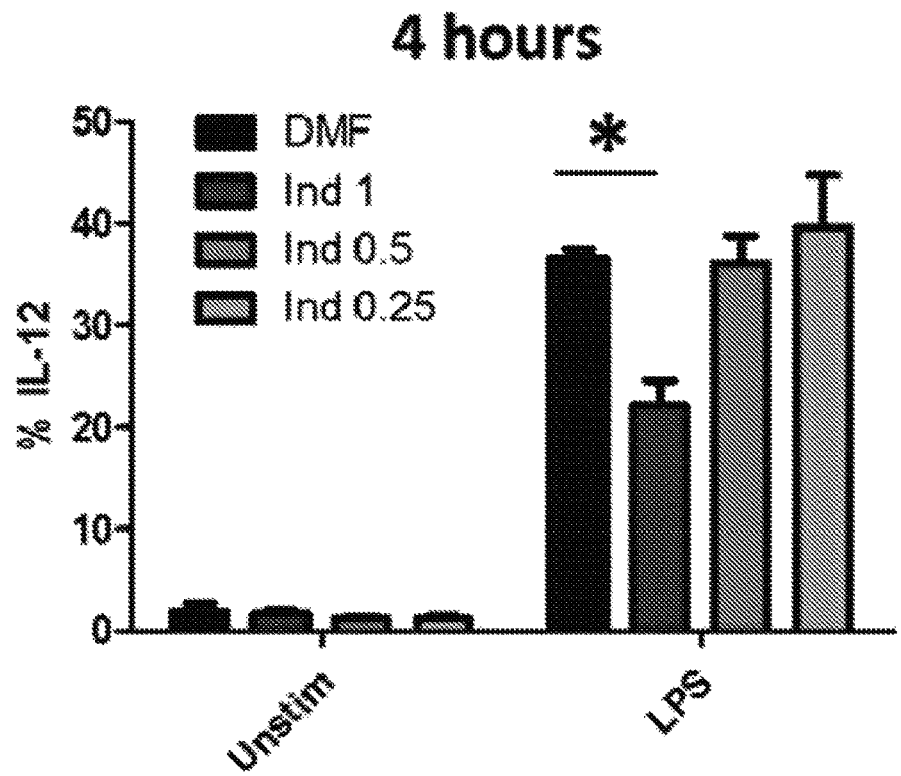

Additionally, to determine if recently arrived macrophage precursors might also be affected, BMDMs were next treated for just 4 hours with indole, followed by a 2 hour stimulation with the same LPS concentrations. Interestingly, a similar inhibition of both cytokines was observed even with this shorter duration of indole conditioning (FIG. 23B). Based on this observation, even a short treatment with indole is sufficient to modify macrophage functions in response to inflammatory stimuli.

Macrophages and monocytes are the predominant source of harmful TNF production in inflammatory diseases (144), so we chose to test indole's effects on primary macrophages ex vivo. Bulk splenocyte cultures were treated with indole overnight, then stimulated with LPS or heat-killed S. typhimurium to induce cytokine production.

Figure 24:
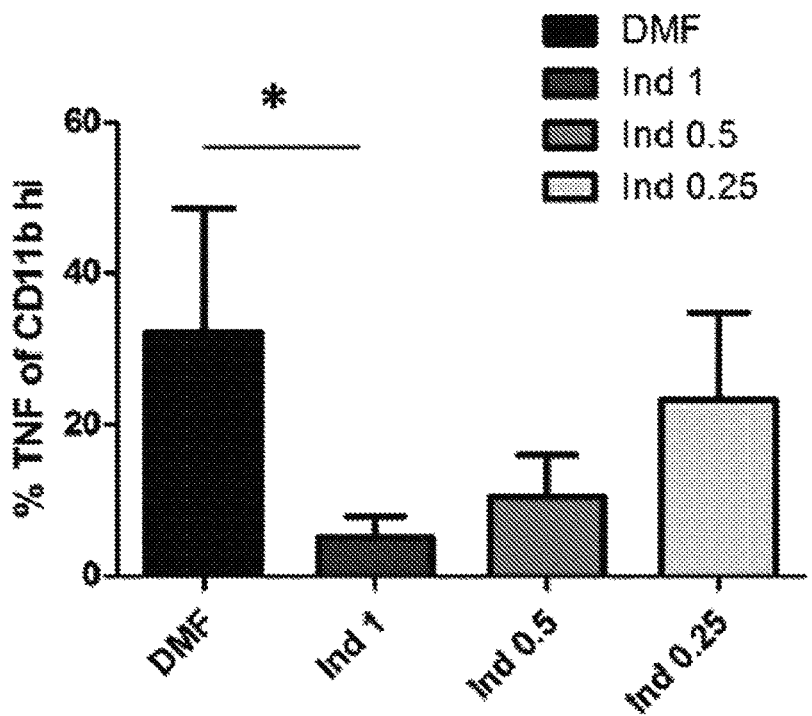
FIG. 24 graphically illustrates that indole conditioning inhibits TNF production in splenic macrophages ex vivo. Splenocytes were cultured for 24 hours with indole or DMF control, then stimulated with LPS (10 ug/ml) or HK-STM ($4\times10^7$ CFU) for 6 hours in the presence of Golgiplug. Cultures were then stained for CD11b and CD11c and intracellular TNF and analyzed by flow cytometry. Analysis was confined to the distinct CD11bhi CD11cneg macrophage population. The mean of three independent experiments is shown. *$p<0.05$ by Student's t test.

Splenic macrophages were distinguished by flow cytometric analysis as those cells negative for lineage markers and expressing very high levels of the integrin CD11b, a population that has been demonstrated to be macrophages derived from conventional hematopoiesis. Here, indole conditioning inhibited TNF production by primary macrophages by an astonishing 75% compared to solvent controls (FIG. 24). When contemplating this result, it is important to consider that these were heterogeneous cultures, thus indole was also in contact with many other immune cells. As such, one explanation is that indole affected other cells in the culture, which then modified macrophage function indirectly. However given the profound effects of indole on purified BMDMs, it is theorized that the effect observed is due to indole's direct action upon the splenic macrophages.

Pro-Inflammatory Signaling Pathways are Inhibited by Indole Conditioning in Macrophages Based on the observation that cytokine production in macrophages is altered by a relatively short treatment with indole, upstream pro-inflammatory signaling pathways might also be affected. Signaling pathways found to be inhibited by indole in DCs were investigated for this context. The transcription factor, Stat3, is a central mediator of numerous physiological processes and has been suggested to be the predominant signal transducer downstream of gp130-like receptors. Contradictory findings have been reported for the role of Stat3 in APC signaling pathways, likely due to the pleiotropic nature of Stat3. Macrophage-specific ablation of Stat3 has been associated with dysregulation and heightened pro-inflammatory cytokine production in response to endotoxin; conversely, hyper-activation of Stat3 in a transgenic mouse model resulted in inflammation and macrophage-specific functional defects. These reports suggest that Stat3 activation is tightly regulated and that the macrophage lineage is sensitive to Stat3 activity.

Figure 25:
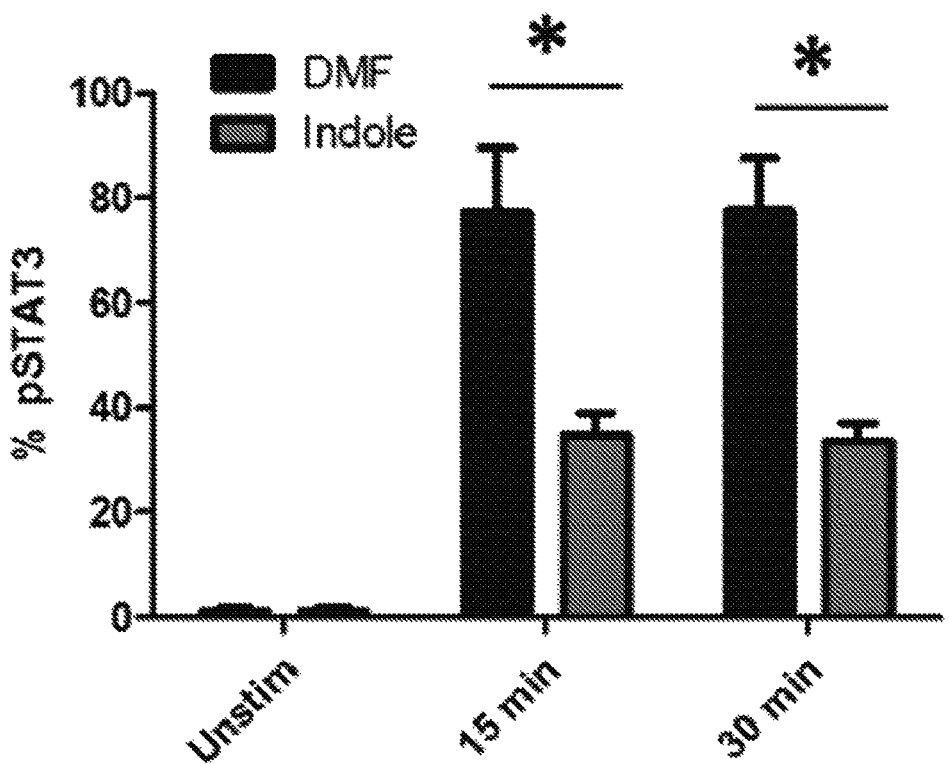
FIG. 25 graphically illustrates that indole inhibits IL-6-induced pStat3 signaling in BMDMs. BMDMs were treated with indole or DMF control for 18 hours, then stimulated with IL-6 (10 ng/ml) for the given times. Cells were stained for phospho-Stat3 and analyzed by flow cytometry. The mean of three independent experiments is shown. * $p<0.05$ by Student's t test.

Stimulation of BMDMs with the canonical Stat3 activator, IL-6, following overnight indole conditioning revealed a robust inhibition of Stat3 phosphorylation. Treatment with indole reduced the number of macrophages undergoing Stat3 phosphorylation by 50% and induced a similar inhibition of mean fluorescent intensity of the activated population (FIG. 25). These data indicate that the Stat3 signaling pathway in macrophages is highly sensitive to indole.

The PI3K/Akt and MAPK/Erk signaling pathways regulate many cellular processes including survival, apoptosis, growth, and cytokine production. It is demonstrated in this study that Akt phosphorylation is inhibited by indole in DCs. Similarly, it was found that indole conditioning dampened pAkt as well as pErk signaling in LPS and CpG-stimulated macrophages by approximately 50% (not shown). Specifically, BMDMs were treated with indole (1 mM) or DMF control for 18 hours, then stimulated with LPS (10 ug/ml) or CpG (5 uM) for 30 minutes. Cells were stained for phospho-Akt or phospho-Erk and analyzed by flow cytometry. Percentage of positive-staining BMDMs indicated on plots. The inhibition of LPS-induced Akt activation has been demonstrated to decrease TNF production in macrophages. As such, indole's upstream inhibition of Akt activation might provide a mechanism for the observed suppression of TNF production.

It has been reported that specific inhibition of Erk in macrophages prior to LPS stimulation resulted in decreased NO production, while TNF and IL-12 expression were unaffected, indicating that Erk signaling is distinct from pro-inflammatory cytokine production. In support of this, butyrate conditioning of colonic lamina propria macrophages inhibited IL-6 and IL-12 expression, while MAP kinases including pErk were unaffected. In contrast, others have reported short chain fatty acid-induced inhibition of Erk1/2 phosphorylation as well as decreased inflammatory mediators (iNOS, TNF, and IL-6) in the RAW264.7 macrophage line, suggesting potential crosstalk. These opposing findings demonstrate that MAP kinase signaling and pro-inflammatory cytokine production can be regulated independently. However, the present observation that signaling pathways downstream of the LPS-detecting TLR4 are inhibited suggests that indole acts at the level of TLR signaling in its suppression of pro-inflammatory cytokine production.

Excessive production of inflammatory mediators in macrophages is associated with numerous inflammatory diseases, including Crohn's disease, metabolic disease, rheumatoid arthritis, and pulmonary fibrosis. The observations described herein suggest that indole is an effective small molecule inhibitor of multiple pro-inflammatory pathways and downstream cytokine responses.

The Effects of Indole on Macrophages Appear to be AhR-Independent

In the current study, it was observed that indole's effects in DCs are independent of the aryl hydrocarbon receptor, whereas concurrent work in the lab has revealed AhR dependence in indole's effects on CD4+T helper cells. To address the question of indole and AhR dependence in macrophages, experiments using BMDMs derived from AhR-knockout mice were run alongside wild-type littermate controls. Specifically, flow cytometric analysis of BMDMs was performed on WT or AhR-KO mice and treated with indole or DMF control for 18 hours. BMDMs were stimulated for 4 hours with LPS (50 ng/ml) in the presence of Golgiplug, then stained for intracellular TNF (left panels) and IL-12 (right panels). Nearly identical effects of indole regardless of AhR status were observed on the production of pro-inflammatory cytokines TNF and IL-12 (not shown). In both cases, cytokine production was reduced by approximately 2-fold subsequent to conditioning of BMDMs with 1 mM indole. Thus, the indole-mediated inhibition of TNF production in BMDMs is AhR-independent.

Similarly, the ex vivo indole conditioning of splenocytes was repeated with tissues from AhR-deficient and wild-type mice and analyzed TNF production. Specifically, splenocytes from WT or AhR-KO (mice were treated with indole or DMF control overnight, followed by stimulation for 6 hours with LPS (10 ug/ml), HK-STM ($4 \times 10^7$ CFU), or CpG (3 uM) in the presence of Golgiplug. Cells were surface stained for CD11b and CD11c followed by intracellular staining for TNF. Flow cytometric analysis was confined to the distinct CD11b$^{hi}$ CD11c$^{neg}$ macrophage population. Percentage of TNF-positive macrophages indicated on plots. Overall TNF production was reduced by 25% or more in AhR-deficient macrophages compared to wild-type controls. However, a marked inhibition of cytokine production was observed with indole treatment in both groups, indicating AhR independence (not shown). Importantly, in this set of experiments splenocytes were stimulated with LPS, heat-killed *S. typhimurium*, and CpG. Indole pre-conditioning dampened TNF production in response to all three stimuli, indicating that the observed effects are not LPS-restricted but can be achieved through the activation of different TLRs. Further, the investigation revealed that indole's robust inhibition of IL-6-mediated Stat3 phosphorylation in BMDMs was entirely AhR-independent (not shown). Specifically, BMDMs were generated from WT or AhR-KO mice and treated with indole (1 mM) or DMF control for 18 hours. BMDMs were then stimulated with IL-6 (10 ng/ml) for the given times and stained for phospho-Stat3, which was detected by flow cytometry. Conditioning with 1 mM indole reduced Stat3 signaling by over 60% regardless of AhR status, confirming that an alternative receptor is responsible for mediating indole's effects in APCs.

Discussion

It is successfully demonstrated herein that the microbiota metabolite, indole, induces profound alterations in macrophage signaling and pro-inflammatory cytokine production. These observations are important for multiple reasons. First, they reveal that indole's effects are common to multiple antigen-presenting cell subsets and are not restricted to DCs. This information helps to guide the search for the mechanism that mediates the effects of indole. Based on similar observations in DCs and macrophages, a logical approach would be to focus on pursuing receptors that are present in both cell types.

Additionally, the results indicate that even a relatively short period of contact with indole is sufficient to induce physiological changes. This suggests that monocytes entering the intestines from circulation likely have the opportunity to be "instructed" by indole to dampen their inflammatory responses to TLR ligands, thus contributing to the tolerogenic landscape of the intestinal environment. This is important because compared to other tissue-resident macrophages, intestinal macrophages have a distinctly short half-life and are under constant renewal and therefore sensitivity to local conditioning factors is likely a key factor in determining their function. As the most abundant mononuclear phagocytes in the lamina propria, macrophages play a key role in promoting a tolerogenic environment and identifying a previously unknown endogenous signal that potentially drives this function would be novel. It has been demonstrated that during colitis, monocytes arriving in the intestines respond to pattern recognition receptor ligands by differentiating into pro-inflammatory macrophages that produce TNF and IL-12 among other inflammatory mediators. Because indole levels are low during colitis, this supports the present model that under steady-state conditions, high levels of indole in the intestines educate antigen-presenting cells to dampen pro-inflammatory responses to TLR stimuli. Under conditions of intestinal inflammation, however, indole levels are significantly depleted and macrophage precursors entering the gut are not exposed to this tolerogenic signal and instead further exacerbate inflammation as a result.

Previously established gut-centric factors that specifically modify macrophage function are few. One such identified factor is intestinal epithelial cells, which produce tolerance-inducing molecules such as thymic stromal lymphopoeitin (TSLP), TGF-β, semaphorin 7A, and prostaglandin E2 to which intestinal macrophages are responsive. The reported HDAC-inhibitory activity of the SCFA, butyrate, was a seminal finding in the pursuit of microbiota components that confer tolerogenic properties upon intestinal macrophages. Here, the current study provides new information as to a novel microbiota signal which directly suppresses pro-inflammatory responses in macrophages. Both primary cultured and splenic macrophages were highly sensitive to indole upon a relatively short treatment period, supporting our hypothesis that indole is a biologically relevant conditioning factor which suppresses inflammatory responses in macrophages upon arrival in the intestinal microenvironment. Based on the present results, it is likely, that indole promotes pathogen clearance and wound healing in intestinal macrophages.

IV. Conclusions

As described herein, subsets of dendritic cells in the GALT can produce retinoic acid from vitamin A and subsequently regulate immunity via mechanisms including imprinting lymphocytes with gut-homing specificity and driving Foxp3+ regulatory T cell development. Indeed, retinoic acid has been previously identified as an essential co-factor in the induction of Foxp3+ Tregs by bona-fide, CD103+ mucosal dendritic cells. The findings described herein reveal that a novel microbiota-derived metabolite, indole, conditions DCs towards a mucosal phenotype in a manner unique from retinoic acid and these indole-conditioned DCs are capable of promoting a regulatory phenotype in naïve T cells.

The disclosed studies also incorporated use of AhR-deficient animals to reveal that indole's effects on APCs are entirely AhR-independent. The small size and freely diffusible nature of indole suggests an intracellular receptor in APCs. In addition, indole seems to affect APCs in a manner similar to TGF-β and retinoic acid, both of which bind intracellular receptors. Further, indole's effects on APCs occur fairly rapidly, as defects were observed in phospho-signaling with as little as four hours indole pre-conditioning.

An intriguing finding in this study was that indole's direct effects on DC phenotype and function occurred in the absence of any exogenous co-factors, whereas indole-conditioned DCs required TGF-β or retinoic acid to affect naïve T cell activation. This might suggest that more than one receptor or pathway mediates indole's effects on APCs.

This work largely focused on dendritic cells, as these antigen-presenting cells act as the predominant activators of naïve T cells in vivo and thus have a crucial role in bridging innate and adaptive immunity. However, macrophages are not only capable of activating naïve T cells, but they play an important role in preventing aberrant mucosal inflammation. The present study indicated that indole affects macrophages in a very similar manner to DCs, and these effects appear AhR-independent in both immune cell subsets.

Ultimately, antigen-presenting cells in the gut provide a crucial function for the host, driving peripheral tolerance towards innocuous antigens and preventing aberrant inflammation. While host-derived factors are known to drive these properties in mucosal APCs, few specific microbiota signals have been identified that modulate mucosal APC characteristics. The experiments described herein uncover a previously unappreciated role for indole in instructing APCs cells towards a mucosal phenotype and function, thus providing evidence for a single metabolite promoting peripheral tolerance (see FIG. 9 for schematic representation). This revelation paves the way for applications for manipulating the microbiota for therapeutic potential in autoimmune and inflammatory disorders of the GI tract.

The following is a brief description of additional studies to determine whether TDMMs other than indole also exhibit regulatory functionality on APCs, such as macrophages and dendritic cells.

Rationale

As described above, the inventors established that indole, a TDMM, was able to condition macrophages and DCs to promote anti-inflammatory phenotypes. Considering that the microbiota have evolved to live commensally in the digestive tract, it was queried whether the microbiota have developed other compositions, such as other TDMMs, that have a similar regulatory effect on APCs.

Results

The inventors performed a series of assays where bone marrow derived macrophages (BMDMs), bone marrow derived dendritic cells (BMDCs), and splenic dendritic cells (splenic DCs), were exposed to a series of TDMMs, including indole, indole-3-acetate (I3AT), 5-hydroxyindole (5HI), and indole-3-pyruvate (I3P), as well as indole-3-carbinol (I3C; a plant derived compound) to be used for a positive control (1 mM for 24 hours). The BMDMs and BMDCs were stimulated with LPS for 4 hours and assayed at day 7 for expression of various pro-inflammatory cytokines. In a similar assay, the BMDMs and BMDCs were stimulated with LPS or CpG, respectively, for 15 minutes and assayed for pAKT and pERK signaling, which is a reflection of pro-inflammatory response.

The data set forth in TABLE 1 show that BMDMs exposed to I3AT exhibited a reduction of IL-12 production, albeit less than with indole exposure. Furthermore, BMDMs exposed to 5HI exhibited reduced pAKT and pERK signaling at levels comparable to indole. This data demonstrates that other TDMMs also exhibit suppressive effects on conditioned BMDMs.

TABLE 1

BMDM production of pro-inflammatory cytokines and signaling pathways after exposure to select TDMMs. Flow cytometric analysis was performed on BMDMs treated with 1 mM of the indicated TDMM for 24 hours. The BMDM were then stimulated with LPS 1 ug/ml for 4 hours for cytokine analysis. Alternatively, the BMDM were stimulated with LPS 1 ug/ml for 15 minutes for pAKT and pERK signaling analysis. Blank cells indicate no assay performed.

|        | TNF       | IL-12     | pAKT      | pERK      |
|--------|-----------|-----------|-----------|-----------|
| Indole | ↓↓↓       | ↓↓↓       | ↓         | ↓         |
| I3C    | ↓↓↓↓      | ↓↓↓↓      | ↓↓        | ↓↓↓↓      |
| I3AT   | No effect | ↓         | No effect | No effect |
| 5HI    |           |           | ↓         | ↓         |
| I3P    |           |           | No effect | No effect |
| I3AD   |           |           | No effect | No effect |

The data set forth in TABLE 2 show that BMDCs exposed to I3AT, 5HI, I3P, and I3 AD, all exhibited a reduction of TNF and IL-12 production. Furthermore, BMDCs exposed to I3AT, 5HI, I3P, and I3AD, all exhibited reduced pAKT and pERK signaling. This data demonstrates that other TDMMs also exhibit suppressive effects on conditioned BMDCs.

TABLE 2

BMDC production of pro-inflammatory cytokines and signaling pathways after exposure to select TDMMs. Flow cytometric analysis was performed on BMDCs treated with 1 mM of the indicated TDMM for 24 hours. BMDCs were then stimulated with LPS (1 ug/ml) for 4 hours for TNF and IL-12 analysis. Alternatively, BMDCs were stimulated with CpG (5 uM) for 15 minutes for pAKT and pERK signaling analysis.

|        | TNF  | IL-12 | pAKT | pERK |
|--------|------|-------|------|------|
| Indole | ↓↓   | ↓↓    | ↓↓   | ↓↓   |
| I3C    | ↓↓↓↓ | ↓↓↓   | ↓↓↓↓ | ↓↓↓↓ |
| I3AT   | ↓    | ↓     | ↓    | ↓    |
| 5HI    | ↓↓   | ↓     | ↓    | ↓    |
| I3P    | ↓    | ↓     | ↓    | ↓    |
| I3AD   | ↓    | ↓     | ↓    | ↓    |

The data set forth in TABLE 3 show that exposure to I3AT, 5HI, I3P, and I3AD inhibits IL-6 induced pSTAT3 signaling in splenic DCs. Briefly, flow cytometric analysis was performed on splenic DCs conditioned with the indicated TDMMs for 24 hours and then subsequently stimulated with 10 ng/ml IL-6 for 30 minutes. All conditioned DCs exhibited a reduction of pSTAT3 signaling after stimulation with IL-6, demonstrating an inhibition of IL-6 induced inflammatory signaling.

TABLE 3

Splenic DC IL-6 induced pSTAT3 expression is inhibited after exposure to select TDMMs. Flow cytometric analysis was performed on Splenic DCs treated with 1 mM of the indicated TDMM for 24 hours. Splenic DCs were then stimulated with IL-6 (10 ng/ml) for 30 minutes for pSTATe signaling.

|       | CD4+ DCs | CD4− DCs |
|-------|----------|----------|
| Indole | ↓↓ | ↓↓ |
| I3C | ↓↓↓↓ | ↓↓↓↓ |
| I3AT | ↓ | ↓ |
| 5HI | ↓ | ↓ |
| I3P | ↓ | ↓ |
| I3AD | ↓ | ↓ |

Conclusion

These data show that the TDMMs other than indole also can condition maturing APCs such as DCs or macrophages to promote an anti-inhibitory phenotype. This illustrates that other TDMMs can be applied to the methods described herein and indicates that the plethora of metabolites produced by the commensal microbiota provide a rich resource for potential therapeutic compositions.

EXAMPLE 1

Mice

C57BL/6 (WT), B6.Cg-Tg(TcraTcrb)$^{425}$Cbn/J (OT-II), and B6.PL-Thy1$^a$/CyJ (B6-Thy1.1) mice were purchased from Jackson Laboratory (Bar Harbor, Me.). C57BL/6-Ahr$^{tm1.2Arte}$ (AhR-KO) mice for initial experiments were a kind gift from Dr. Bhagavatula Moorthy (Baylor College of Medicine, Houston Tex.). Further AhR-KO mice were purchased from Taconic Farms (Rockville, Md.). Mice were maintained in a specific pathogen-free animal facility located at Texas A&M University Health Science Center. All animal procedures were performed in accordance with the Institutional Animal Care and Use Committee guidelines under an approved animal use protocol. Mice were age and gender-matched for each experiment and used between 6 and 13 weeks of age.

Reagents

Indole and all-trans retinoic acid were purchased from Sigma (St. Louis, Mo.). Indole was dissolved in dimethylformamide (DMF) and added to cultures at indicated concentrations. Recombinant murine GM-CSF and TGF-β1 were purchased from R&D Systems (Minneapolis, Minn.). Ultra-pure LPS from Invitrogen (San Diego, Calif.) was used for DC activation. Cell Rox Deep Red reagent for detection of reactive oxygen species (ROS) was obtained from Molecular Probes (Invitrogen, USA). Pacific Blue Succinimidyl Ester (PBSE) was used for discrimination of viable cells (Life Technologies). OVA$_{323-339}$ peptide was purchased from AnaSpec, Inc. (Fremont, Calif.).

Antibodies used for flow cytometry included CD4 (clone RM-5), CD11c (HL3), CD86 (GL1), I-Ab (AF6-120.1), TNF (MP6-XT22), IL12 (c15.6), IL-6 (MP5-20F3), phospho-Stat3 (4/P-STAT3) and LPAM-1/α4β7 (DATK32) purchased from BD Biosciences (San Jose, Calif.). Anti-Foxp3 (FJK-16s), CCR9 (CW-1.2), CD45R/B220 (RA3-6B2) and TLR4/MD-2 (MTS510) were purchased from eBioscience (San Diego, Calif.) and phospho-Akt (193H12) and phospho-NF-kB p65 (93111) were purchased from Cell Signaling Technology (Beverly, Mass.).

Cell Culture

DC Culture and Stimulation

The murine dendritic cell line DC2.4 was kindly provided by Dr. Kenneth Rock, University of Massachusetts Medical Center. DC2.4 cells were maintained in complete DMEM medium (Invitrogen, Grand Island, N.Y.) supplemented with 5% fetal calf serum (FCS). All primary cells were cultured in RPMI 1640 supplemented with 2-mercaptoethanol, gentamicin, penicillin, streptomycin, and 10% FCS (all from Life Technologies). Bone marrow-derived dendritic cells were cultured as previously described (Inaba K, et al. (1992) Generation of large numbers of dendritic cells from mouse bone marrow cultures supplemented with granulocyte/macrophage colony-stimulating factor. *The Journal of Experimental Medicine* 176(6):1693-1702) with slight modifications. Briefly, bone marrow cells were harvested from murine femurs and cultured in complete media supplemented with 10% FCS, 20 ng/ml GM-CSF (Peprotech), and 10 ng/ml IL-4 (Peprotech). Media was replenished at day 2, 4, and 6 of the 7 day culture. Indole, RA, or solvent control were added to the cultures at day 3 where indicated. Stimulation of dendritic cells at the given concentrations of LPS or heat-killed *S. typhimurium* were performed for 4 hours (DC2.4 and BMDCs) or 6 hours (primary splenic DCs) in the presence of GolgiPlug protein transport inhibitor (BD Biosciences) to measure cytokine production, or for 24 hours (co-stimulatory markers).

Macrophage Culture

Bone marrow was harvested as described above and cultured at a density of 1×10$^6$ cells in 10 ml complete media supplemented with 10 ng/ml M-CSF (Peprotech) in 100 mm×15 mm petri dishes. Media with cytokine was replenished on day 3. Adherent and semi-adherent cells were recovered on day 7, plated, and treated with indole prior to downstream experiments.

Assays

NF-kB Activity Assay

The DC2.4-NFkB-GLuc cell line was generated in-house. A reporter plasmid with tandem repeats of NF-kB response element was designed and integrated into the genomic DNA of the DC2.4 cell line via lentiviral transduction. A minimal inducible cytomegalovirus (CMV) promoter was cloned upstream of GLuc (*Gaussia* luciferase, a secreted reporter) to monitor NF-kB activation. The inducible promotor is inactive in the absence of NF-kB binding to DNA. DC2.4-NFkB-GLuc cells were pre-treated with indole and/or TGF-β for 24 hours followed by LPS stimulation (10 ug/ml). Culture supernatants were collected at 8 and 24 hours and assayed for GLuc using Biolux *Gaussia* Luciferase assay kit (New England BioLabs).

Cytotoxicity Assay

The CytoTox96 non-radioactive cytotoxicity assay (Promega) was used to identify cytotoxic effects of indole. Cells were treated with or without indole for various durations and the amount of lactate dehydrogenase (LDH) released into the culture supernatant was measured.

Reactive Oxygen Species (ROS) Production

Reactive oxygen species production was measured using the CellRox Deep Red Reagent (ThermoFisher). Briefly, cells were treated with or without indole for 18 hours, then labeled with CellRox (5 uM) for 30 minutes and washed with PBS followed by LPS stimulation. Presence of ROS oxidizes the CellRox reagent to a fluorescent state that can be subsequently analyzed via flow cytometry.

Nitric Oxide (NO) Production

Nitric oxide concentration was determined by measuring nitrite levels in culture supernatants via the Griess reaction (Granger D L, Taintor R R, Boockvar K S, & Hibbs J B (1996) Measurement of nitrate and nitrite in biological samples using nitrate reductase and Griess reaction. *Methods in Enzymology* 268:142-151). Briefly, cells in the presence or absence of indole were stimulated with LPS for 24 hours. Supernatants were then incubated with Griess reagent for 10 minutes and then absorbance was measured at 550 nm.

Antigen-Uptake Assay

Ovalbumin (OVA)-Alexafluor 488 conjugate (Molecular Probes) was used for measuring antigen uptake by DCs. Subsequent to 24 hour indole conditioning, cells were incubated with 1 µg/ml OVA-A488 at 4° C. or 37° C. for 1 or 4 hours. Cells were then washed 3 times with ice-cold PBS containing 0.5% BSA to terminate uptake. Cells were surface stained for CD11c and fixed with 4% paraformaldehyde. Uptake of OVA-A488 was measured by flow cytometry.

Aldehyde Dehydrogenase Activity

Activity of aldehyde dehydrogenase (ALDH) in individual BMDCs was measured using an Aldefluor staining kit (Stem Cell Technologies) according to the manufacturer's instructions with minor modifications. Briefly, BMDCs were incubated with Aldefluor substrate (150 nm) for 45 minutes at 37° C., with or without ALDH inhibitor 4-(diethylamino) benzaldehyde (DEAB) at (100 µm). Subsequently, cells were stained with CD11c in cold Aldefluor assay buffer and then analyzed by flow cytometry.

Real-Time PCR

Total RNA was extracted from BMDCs using RNeasy Mini Kit (Qiagen) and then retro-transcribed using cDNA Superscript Mastermix (Quanta). Quantitative PCR reactions were carried out in triplicate using Perfecta SYBR Green Fast Mix, Low ROX (Quanta).

Gene expression levels for each individual sample were normalized to 18 s. Mean relative gene expression was determined and differences were calculated using the $2^{-\Delta C(t)}$ method. The following primer sequences (5'-3') were used:

```
Murine aldh1a2
                                     (SEQ ID NO: 1)
F: CATGGTATCCTCCGCAATG (SEQ ID NO: 2)
R: GCGCATTTAAGGCATTGTAAC Murine 18s
                                     (SEQ ID NO: 3)
F: TCAACTTTCGATGGTAGTCGCCGT (SEQ ID NO: 4)
R: TCCTTGGATGTGGTAGCCGTTTCT
```

ELISA

Cytokine concentration in the supernatant of BMDC cultures was assessed using commercially available ELISA kits for IL-10 (Peprotech) and TGF-β (eBioscience) per the manufacturer's instructions.

Chemotaxis Assay 24-well Transwell cell culture plates with 8.0 uM polycarbonate membranes were used for this assay (Corning) along with chemokines CCL25 (CCR9 ligand), CCL19 and CCL21 (CCR7 ligands; all from Peprotech). A volume of 600 ul cell culture media containing 1 ug/ml of either CCL25 or CCL19 and CCL21 was placed in the bottom chamber, followed by the transwell insert. BMDCs conditioned with indole, RA, or DMF from day 3 were harvested and washed on day 7. Exactly 100 ul of cell culture media containing $4.5 \times 10^5$ BMDCs was added to the upper chamber of the transwell.

Controls without the presence of chemoattractants were included. Plates were incubated for 3 hours at 37° C., at which point transwell inserts were removed and migrated cells in the bottom chamber were collected and counted. Migration is expressed as a percentage of the initial cell number.

DC-T Cell Co-Cultures (Polyclonal Stimulation)

Naïve CD4+CD25− T cells from pooled spleen and lymph nodes of C57BL/6 wild-type mice were sorted to high purity (>97%) on a BD FACS Aria II flow cytometer (BD Biosciences). Antibodies used for staining were αCD4 (GK1.5) and αCD25 (PC61.5). BMDCs were previously treated with indole from day 3. On day 7, DCs were washed extensively prior to being co-cultured with the naïve FACS-sorted T cells for 72 hours in a 96-well round-bottom tissue culture plate in the presence of soluble anti-CD3 at 5 ug/ml (BioXcell clone 145-2C11) as well as 2 ng/ml TGF-β (Peprotech) and/or 100 U/ml IL-2 (Roche). Subsequently, cells were stained for flow cytometric analysis using αCD4 (GK1.5) and αFOXP3 (FJK-16s).

DC-T Cell Co-Cultures (Monoclonal Stimulation)

Naïve CD4+CD25− T cells of spleen and lymph nodes from OT-II mice were isolated by negative selection via column purification using the Naïve CD4+ T Cell Isolation Kit (Miltenyi Biotec). Naïve CD4+ T cells (>96% pure) were labeled with Cell Proliferation Dye efluor450 (eBioscience) following manufacturer's instructions then co-cultured with OVA peptide-loaded BMDCs at a ratio of 2:1 for 72 hours in a 96-well round-bottom tissue culture plate. BMDCs were previously treated with indole or RA from day 3. On day 7, DCs were washed extensively prior to being loaded with $OVA_{323-339}$ peptide (10 ug/ml) for 1 hour at 37° C. BMDCs were then washed three times and plated with naïve CD4+ T cells. RA or TGFβ were added to co-cultures as indicated. Following 3 days of culture, cells were stained with antibodies to CD4, CCR9, and LPAM-1 (α4β7). Intracellular staining for Foxp3 was performed using a Foxp3 staining kit (eBioscience). The remaining CD4+ helper T cell lineages Th1, Th2, and Th17 were identified by their cytokine production. For Th2 and Th17 differentiation cultures, lineage skewing cytokines were included for the duration of the co-culture. For Th2 skew, cultures received 0, 10, 50, or 100 ug/ml of each αIFN-γ (BioXCell R4-6A2) and IL-4 (Peprotech). For Th17 skew, cultures received 0, 10, or 50 ng/ml each of TGF-β (Peprotech), IL-6 (Peprotech), and IL-23 (R&D). Production of cytokines was stimulated by the addition of PMA and ionomycin (Sigma-Aldrich) during the last five hours of culture. Cytokines were retained inside the cells by the addition of the protein transport inhibitor, Golgiplug (BD) at the time of stimulation. Cells were fixed and permeabilized using the Foxp3 staining kit (eBioscience). Antibodies used for intracellular cytokines were αIFN-γ-PE (eBioscience XMG1.2), αIL-4-

FITC (eBioscience BVD6-24G2), and αIL-17-efluor660 (eBioscience eBio17B7) to detect Th1, Th2, and Th17 cells, respectively.

DC-T Cell Co-Cultures without Cell Contact

Naïve CD4+CD25− T cells were FACS-sorted and placed in the bottom of a 24-well Transwell cell culture plate with 0.4 uM polycarbonate membranes (Corning) that had been coated with 5 μg/mL αCD3 (BioXcell 145-2C11) and 2 μg/mL αCD28 (BioXcell 37.51). TGF-β was added at the indicated concentrations. The insert was placed in the well and washed, Day 3-treated BMDCs were added to the top chamber such that culture media was shared, but the cell types were kept physically separate. The T cell to DC ratio was 2:1, as in other co-culture experiments.

T Cell Activation in the Presence of BMDC Supernatant

Naïve CD4+CD25− T cells were FACS-sorted as described above and plated in 96-well, αCD3 and αCD28-coated tissue culture plates in a volume of 100 ul cell culture media. An equal volume of spent BMDC supernatant was added, in the presence or absence of exogenous TGF-β, and T cells were cultured for 72 hours. To generate supernatants, day 3-treated BMDCs were collected on day 7, washed extensively and plated in a 48-well cell culture plate at $5 \times 10^5$ cells per well in 500 ul fresh complete media for 24 hours in the presence or absence of 1 ug/ml LPS. Plates were then centrifuged and supernatants were collected, filtered, and stored at −20° C. until use.

In Vivo T Cell Activation by Indole-Treated BMDCs

Naïve CD4+CD25− T cells from spleens and lymph nodes of OT-II mice were isolated by column purification as described above and resuspended in sterile Hanks Balanced Saline Solution (HBSS). Approximately 2 million T cells were transferred via i.v. injection (retro-orbital route) into recipient B6-Thy1.1 mice. Day 7 BMDCs cultured with indole, RA, or DMF from day 3 were washed and loaded with OVA peptide as described above. Two million BMDCs were resuspended in sterile HBSS and transferred i.p. into the same B6-Thy1.1 recipient mice 5 hours subsequent to T cell transfer. After 5 days, tissues were harvested for cellularity analysis as well as ex vivo stimulation for cytokine production.

BMDC Transfer with DSS-Colitis

BMDCs were cultured with indole, RA, or DMF from day 3 as described above. BMDCs were washed, counted, and resuspended in sterile PBS (Ca—Mg—) for transfer to WT C57BL/6 recipients. Two million BMDCs were transferred via i.p. injection on days 0, 6, and 9 of the experiment. Mice received 5% dextran sulfate sodium (DSS, MW=36,000-50,000; MP Biomedicals) ad libitum in their drinking water from day 7 through day 14. Mice were weighed daily to monitor weight loss. Mice were euthanized on day 20 for subsequent tissue harvest and processing.

Statistical Analysis

Data were analyzed using GraphPad Prism Software 5.01. Comparisons between DMF and indole were performed using a Student's t test. One-way ANOVA followed by Dunnett's post test was applied to compare differences in experiments with DMF, indole, and RA treatment groups. P values of less than 0.05 were considered to be statistically significant.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of maturing an antigen presenting cell (APC), comprising contacting an immature APC in vitro with an effective amount of a composition comprising isolated or purified indole, and permitting maturation of the APC.

2. The method of claim 1, wherein the APC is a dendritic cell.

3. The method of claim 2, wherein the APC is a gut-associated lymphoid tissue (GALT) dendritic cell.

4. The method of claim 1, wherein the APC is a macrophage.

5. The method of claim 1, further comprising exposing the immature APC to an antigen to which tolerance is desired.

6. The method of claim 1, wherein the mature APC exhibits an anti-inflammatory phenotype.

7. The method of claim 1, further comprising exposing the mature APC to a naïve T cell in vivo or ex vivo.

8. A method of promoting anti-inflammatory phenotype, comprising contacting an immature antigen presenting cell (APC) in vitro with a composition comprising isolated or purified indole.

9. The method of claim 8, wherein promoting anti-inflammatory phenotype comprises promoting peripheral tolerance of antigens in the gut of a subject.

10. The method of claim 8, wherein the APC is a dendritic cell.

11. The method of claim 10, wherein the APC is a mucosal dendritic cell.

12. The method of claim 10, wherein the APC is a gut-associated lymphoid tissue (GALT) dendritic cell.

13. The method of claim 8, wherein the APC is a macrophage.

14. The method of claim 8, further comprising administering the exposed APC to the subject.

15. The method of claim 8, further comprising exposing the mature APC to a naïve T cell in vivo.

16. A method of promoting development of a T regulatory cell (Treg) from a naive T cell, comprising contacting the naive T cell to an antigen presenting cell (APC) that has been conditioned in vitro or ex vivo with a composition comprising isolated or purified indole.

17. The method of claim 16, wherein the Treg has an increased FoxP3 expression as compared to the naïve T cell.

18. The method of claim 16, wherein the indole-conditioned APC is produced by contacting an immature APC to the composition comprising the isolated or purified indole and permitted to mature.

19. The method of claim 18, wherein the APC is a dendritic cell or macrophage.

20. The method of claim 19, wherein the dendritic cell is a gut-associated lymphoid tissue (GALT) dendritic cell.

21. The method of claim 16, wherein the Treg is produced in vitro and is administered to a subject in need.

* * * * *